(12) United States Patent
Brewer et al.

(10) Patent No.: US 7,438,931 B2
(45) Date of Patent: Oct. 21, 2008

(54) METHODS AND COMPOSITIONS FOR THE TREATMENT OF ANGIOGENIC DISEASES

(75) Inventors: George J. Brewer, Ann Arbor, MI (US); Sofia D. Merajver, Ann Arbor, MI (US); Dimitri Coucouvanis, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 10/796,782

(22) Filed: Mar. 9, 2004

(65) Prior Publication Data

US 2005/0058720 A1    Mar. 17, 2005

Related U.S. Application Data

(63) Continuation of application No. 09/389,435, filed on Sep. 3, 1999, now Pat. No. 6,703,050.

(60) Provisional application No. 60/099,103, filed on Sep. 4, 1998, provisional application No. 60/101,759, filed on Sep. 25, 1998.

(51) Int. Cl.
*A61K 33/34* (2006.01)
*A61K 33/30* (2006.01)

(52) U.S. Cl. .................... 424/641; 424/646; 514/502

(58) Field of Classification Search ................ 424/641, 424/646; 514/53, 503
See application file for complete search history.

(56) References Cited

U.S. PATENT DOCUMENTS

| | | | |
|---|---|---|---|
| 2,909,541 A | 10/1959 | Hugel | |
| 3,845,770 A | 11/1974 | Theeuwes et al. | |
| 3,916,899 A | 11/1975 | Theeuwes et al. | |
| 4,343,746 A | 8/1982 | Anglin et al. | |
| 4,604,278 A | 8/1986 | Reilly et al. | |
| 4,678,667 A | 7/1987 | Meares et al. | 424/85 |
| 4,762,705 A | 8/1988 | Rubin | 424/85 |
| 4,765,539 A | 8/1988 | Noakes et al. | |
| 4,766,226 A | 8/1988 | Hill et al. | 556/18 |
| 4,952,607 A | 8/1990 | Sorenson et al. | 514/589 |
| 5,057,302 A | 10/1991 | Johnson et al. | 424/1.1 |
| 5,100,885 A | 3/1992 | Abrams et al. | 514/184 |
| 5,112,598 A | 5/1992 | Biesalski | |
| 5,169,858 A | 12/1992 | Rubin | 514/365 |
| 5,385,933 A | 1/1995 | Rabinovitz et al. | 514/499 |
| 5,391,547 A | 2/1995 | Cole et al. | 514/184 |
| 5,443,816 A | 8/1995 | Zamora et al. | 424/1.69 |
| 5,512,559 A | 4/1996 | Skalkos et al. | 514/185 |
| 5,527,533 A | 6/1996 | Tso et al. | |
| 5,556,611 A | 9/1996 | Biesalski | |
| 5,563,132 A | 10/1996 | Bodaness | 514/185 |
| 5,565,491 A | 10/1996 | Schieven | 514/492 |
| 5,583,153 A | 12/1996 | Brahn | |
| RE35,458 E | 2/1997 | Azuara | 556/116 |
| 5,639,725 A | 6/1997 | O'Reilly et al. | |
| 5,639,757 A | 6/1997 | Dow et al. | 514/261 |
| 5,697,902 A | 12/1997 | Goldenberg | 604/49 |
| 5,698,155 A | 12/1997 | Grosswald et al. | |
| 5,712,291 A | 1/1998 | D'Amato | 514/323 |
| 5,753,230 A | 5/1998 | Brooks et al. | 424/158.1 |
| 5,950,619 A | 9/1999 | van der Linden et al. | |
| 5,954,047 A | 9/1999 | Armer et al. | |
| 5,970,974 A | 10/1999 | Van Der Linden et al. | |
| 5,972,922 A | 10/1999 | Wilks et al. | 514/178 |
| 6,703,050 B1 | 3/2004 | Brewer et al. | |
| 2004/0009237 A1 | 1/2004 | Brewer | 424/617 |

FOREIGN PATENT DOCUMENTS

| | | |
|---|---|---|
| EP | 1 234 585 A2 | 8/2002 |
| EP | 1 107 795 B1 | 11/2002 |
| WO | WO 00/13712 | 3/2000 |
| WO | WO 2004/009072 | 1/2004 |

OTHER PUBLICATIONS

Brewer, G. "Tetrathiomolybdate anticopper therapy for Wilson's disease . . . " J. Cell. Mol. Med. (2003) vol. 7, No. 1, pp. 11-20.*
Elner, S. et al "Effects of tetrathiomolybdate in a mouse model . . . " Invest. Ophthalmol. Vis. Sci. (2005) vol. 46, No. 1, pp. 299-303.*
Allen and Solomons, "Normal intestinal mechanisms in the absorption of copper," In: *Absorption and Malabsorption of Mineral Nutrients*, Solomons and Rosenberg, Eds., Alan R. Liss, Inc., New York, 12:199-229, 1984.
Alpern-Elran and Brem, "Angiogenesis in human brain tumors: inhibition by copper depletion," *Neurological Surgery*, pp. 498-500, publication date unknown.
Brem et al., "Anticopper treatment inhibits pseudopodial protrusion and the invasive spread of 9L gliosarcoma cells in the rat brain," *Neurosurgery*, 26:391-396, 1990.
Hill et al., "Treatment of Wilson's disease with zinc, I: oral zinc therapy regimens," *Hepatology*, 7:522-528, 1987.
Hourani and Demopoulos, "Inhibition of S-91 mouse melanoma metastases and growth by D-penicillamine," *Laboratory Investigation*, 21(5):434-438, 1969.
Kanatzidis and Coucouvanis, "Structure of Bis(tetraethylammonium) tetrathiomolybdte(VI), $2C_8H_{20}N^+MoS_4^{2-}$," *Acta Cryst.*, C39:835-838, 1983.

(Continued)

*Primary Examiner*—Leigh C Maier
(74) *Attorney, Agent, or Firm*—Marshall, Gerstein & Borun LLP

(57) ABSTRACT

Provided are agents that can bind to copper, and form a tripartite complex with protein, and the use of these agents in the prevention and treatment of diseases with a vascular component, such as solid tumors. Compositions and methods for combination therapy of these diseases, including cancer, as well as therapeutic kits, are also provided.

25 Claims, 4 Drawing Sheets

OTHER PUBLICATIONS

Lee et al., "The Treatment of Wilson's Disease with Zinc VII. Protection of the Liver for Copper Toxicity by Zinc Induced Metallothionein in a Rat Model," *J. Lab. Clin. Med.*, 114:639-645, 1989.

Marshall et al., "Phase I trial of orally administered pentosan polysulfate in patients with advanced cancer," *Clin. Cancer Res.*, 3:2347-2354, 1997.

Merajver et al., "Copper depletion as an anti-angiogenic strategy in HER2-neu transgenic mice," *Proceedings of Special AACR Conference on Angiogenesis and Cancer*, Abstract #B-11, Jan. 22-24, 1998.

Merajver, "Phase I study of tetrathymolybdate in metastatic cancer," NIH Grant No. 5R03CA77122-02.

Mills et al., "Effects of molybdate, sulfide, and tetrathiomolybdate on copper metabolism in rats," *J. Inorg. Biochem.*, 14:189, 1981.

Mills et al., "Copper and molybdenum absorption by rats given ammonium tetrathiomolybdate," *J. Inorg. Biochem.*, 14: 163, 1981.

Parke et al., "Characterization and quantification of copper sulfate-induced vascularization of the rabbit cornea," *Am. J. Pathol.*, 130:173-178, 1988.

Patstone and Maher, "Copper and calcium binding motifs in the extracellular domains of fibroblast growth factor receptors," *J. Biol. Chem.*, 271:3343-3346, 1996.

Brem "Angiogenesis and cancer control: From concept to therapeutic trail," *Cancer Control*, 6(5):436-458, 1999.

Brewer and Merajver, "Treatment of metastatic cancer with the anticopper antiangiogenenic drug tetrathiomolybdate," *J. Invest. Med.*, 47(7):223A, 1999.

Brewer et al., "Treatment of metastatic cancer with tetrathiomolybdate, an anticopper, antiangiogenic agent: Phase I study," *Clin. Canc. Res.*, 6(1):1-10, 2000.

International Search Report dated Jul. 4, 2000 (PCT/US99/20374; 4100.001010).

Merajver, "A Phase I study of oral tetrathiomolybdate (TM) as a decoppering and anti-angiogenesis agent for metastatic cancer," From the Internet at website http://www.cancer.med.umich.edu/cgi-bin/protocol?9708_701, 1998.

Sergeant and Johnson, "Iron and copper requirements for proliferation and differentiation of a human promyelocytic leukemia cell line (HL-60)," *J. Cell. Physiol.*, 163:477-485, 1995.

Shah et al., "Circular dichroism of carbohydrate-molybdate complexes," *Stud. Nat. Prod. Chem.*, 15:423-438, 1995.

Vine, et al. "Tetrathiomolybdate as an Antiangiogenesis Therapy for Subfoveal Choroidal Neovascularization Secondary to Age-Related Macular Degeneration," Trans. Am. Ophthalmol. Soc. vol. 100:73-77 (2002).

Brem et al., "Inhibition of angiogenesis and tumor growth in the brain. Suppression of endothelial cell turnover by penicillamine and the depletion of copper, an angiogenic colactor," *Am. J. Pathol.*, 137(5):1121-1142, 1990.

Brem et al., "Tetrathiomolybdate, a chelator of copper, reduces intracerebral peritumoral edema in rats," *Proceeding of the American Association for Cancer Research*, 33:76, Abstract 455, 1992.

Bremner et al., "Copper metabolism in rats given di-or trithiomolybdates," *J. Inorg. Biochem.*, 16: 109, 1982.

Brewer and Yuzbasiyan-Gurkan, "Wilson Disease," *Medicine*, 71(3):139-164, 1992.

Brewer and Yuzbasiyan-Gurkan, "Wilson's Disease," In: *Textbook of Clinical Neuropharmocology and Therapeutics*, 2nd Edition, Klawans et al., Eds., Raven Press, New York, pp. 191-205, 1992.

Brewer and Yuzbasiyan-Gurkan, "Wilson's disease: an update, with emphasis on new approaches to treatment," *Dig. Dis.*, 7(4):178-193, 1989.

Brewer, "Interactions of zinc and molybdenm with copper in therapy of Wilson's disease," *Nutr.*, 11(1 Suppl):114-116, 1995.

Brewer, "Practical recommendations and new therapies for Wilson's disease," *Drugs*, 50(2):240-249, 1995.

Brewer, "Thiomolybdates in the treatment of Wilson's disease," *Arch. Neurol.*, 49: 132-133, 1992.

Brewer, "Zinc in the Treatment of Wilson's Disease," *Nutrition and the M.D.* 19(12): 1993.

Brewer et al., "Treatment of Wilson's disease with ammonium tetrathiomolybdate. I Initial therapy in 17 neurologically affected patients," *Arch. Neurol.*, 51(6):545-554, 1994.

Brewer et al., "Use of zinc acetate to treat copper toxicosis in dogs," *JAVMA* 201:564-568, 1992.

Brewer et al., "Treatment of Wilson's Disease with zinc XIII: Therapy with zinc in presymptomatic patients from the time of diagnosis," *J. Lab. Clin. Med.*, 123:849-858, 1994.

Brewer et al., "Initial therapy of Wilson's Disease patients with tetrathiomolybdate," *Arch. Neurol.*, 48(1):42-47, 1991.

Brewer et al., "Treatment of Wilson's Disease with zinc III. Prevention of reaccumulation of hepatic copper," *J. Lab. Clin. Med.*, 109:526-531, 1987.

Brewer et al., "Oral zinc therapy for Wilson's disease," *Annals Int. Med.*, 99:314-320, 1983.

Brewer et al., "Treatment of Wilson's Disease with zinc: IV. Efficacy monitoring using urine and plasma copper," *Proc. Soc. Exper. Biol. Med.*, 184:446-455, 1987.

Brewer et al., "Treatment of Wilson's disease with ammonium tetrathiomolybdate II. Initial therapy in 33 neurologically affected patients and follow-up on zinc therapy," *Arch. Neurol.*, 53:1017-1025, 1996.

Brewer et al., "The use of $^{64}$copper measurements to diagnose canine copper toxicosis," *J. Vet. Int. Med.*, 6:41-43, 1992.

Brewer et al., "Worsening of neurological syndrome upon initial treatment of Wilson's Disease patients with penicillamine," *Arch. Neurol.*, 44:490-493, 1987.

Brewer et al., "Development of neurologic symptoms in a patient with asymptomatic Wilson's disease treated with penicillamine," *Arch. Neurol.*, 51:304-305, 1994.

Brewer et al., "Zinc therapy of Wilson's Disease VIII. Dose response studies," *J. Trace Elem. Exp. Med.*, 3:227-234, 1990.

Brewer et al., "Treatment of Wilson's Disease with zinc: IX. Response of serum lipids," *J. Lab. Clin. Med.*, 118:466-470, 1991.

Brewer et al., "Treatment of Wilson's Disease with zinc XI. Interaction with other anticopper agents," *J. Amer. Coll. Nut.*, 12(1):26-30, 1993.

Brewer et al., "Treatment of Wilson's Disease with zinc XII. Dose regimen requirements," *Amer. J. Med. Sci.*, 305: (4):199-202; 1993.

Brewer et al., "Molecular genetics and zinc-copper interactions in human Wilson's Disease and canine copper toxicosis," In: *Essential and Toxic Trace Elements in Human Health and Disease: An Update*, Prasad, Ed., Allan R. Liss, New York, PCBR 380:129-145, 1993.

Brewer et al., "Treatment of Wilson's Disease with zinc VI. Initial treatment studies," *J. Lab. Clin. Med.*, 114: 633-638, 1989.

Brewer et al., "Treatment of Wilson's Disease," *Sem. Neurol.*, 7:209-220, 1987.

Coucouvanis et al., "An inorganic functional group approach to the systematic synthesis and reactivity studies of binuclear Mo/S and Mo/S/O complexes," *Polyhedron*, 8(13/14):1705-1716, 1989.

Coucouvanis et al., "Dinuclear Fe-Mo-S complexes containing the FeS2Mo core. Syntheses, ground-state electronic structures, and crystal and molecular structures of the $[(C_6H_5)_4P]_2[(C_6H_5)_2FeS_2MoS_2]$, $[(C_2H_5)_4N]_2[(C_6H_5)_2FeS_2WS_2]$, and $[(C_6H_5)_4P]_2[(S)_5FeS_2MS_2]$ (M=Mo, W) complexes," *Inorg. Chem.*, 22:293-308, 1983.

Coucouvanis et al., "Heterodinuclear Di-µ-sulfido bridged dimers containing iron and molybdenum or tungsten. Structures of $(PhP)_2(FeMS_9)$ complexes (M=Mo, W)," *J. Am. Chem. Soc.*, 102:1730-1732, 1980.

Coucouvanis et al., "Successful isolation of a reduced tetrathiometallate complex. Synthesis and structural characterization of the $[(MoS^4)_2Fe]^{3-}$ trianion," *J. Am. Chem. Soc.*, 102:6644-6646, 1980.

Coucouvanis et al., "Synthesis and structural characterization of $[(No)^?FeS_2MoS_2]^{2-}$ a dinitrosyl complex containing the $FeS_2MoS_2$ core," *Inorg. Chim. Acta*, 53:L135-L137, 1981.

Coucouvanis et al., "Synthesis of thiomolybdenyl complexes with $[Mo_2(S)_2(O)_2]^{2+}$ cores and substitutionally labile ligands. Crystal and molecular structure of the $[Mo_2O_2S_4(DMF)_3]$ complex," *Inorg. Chem.*, 27:3272-3273, 1988.

Coucouvanis et al., "Trinuclear Fe-M-S complexes containing a linear Fe-M-Fe array and a bridging S2MS2 unit. Electronic structures and crystal and molecular structures of the [(C₆H₅)₄P]₂[Cl₂FeS₂MS₂FeCl₂] (M=Mo, W) complexes," *Inorg. Chem.*, 23:741-749, 1984.

Coucouvanis, "Fe-M-S complexes derived from $MS_4^{2-}$ anions (M=Mo, W) and their possible relevance as analogues for structural features in the Mo site of nitrogenase," *Acc. Chem. Res.*, 14:201-209, 1981.

Coucouvanis, "Syntheses, structures, and reactions of binary and tertiary thiomolybdate complexes containing the (O)Mo(S$x$) and (S)Mo(S$x$) functional groups ($x$=1, 2, 4)," *Adv. Inrog. Chem.*, 45:1-73, 1998.

Engleka and Maciag, "Inactivation of human fibroblast growth factor-1 (FGF-1) activity by interaction with copper ions involves FGF-1 dimer formation induced by copper-catalyzed oxidation," *J. Biol. Chem.*, 267:11307-11315, 1994.

Fell et al., "Gut Pathology of Rats Dosed with Tetrathiomolybdate," *J. Com. Pathol.*, 89:495, 1979.

Folkman, "Angiogenesis," *The Journal of Biological Chemistry*, 267(16):10931-10934, 1992.

Folkman and Klagsburn, "Angiogenic factors," *Science*, 23:442-447, 1987.

Folkman, "Angiogenesis in cancer, vascular, rheumatoid and other disease," *Nature Med.*, 1:27-31, 1995.

Folkman, "The influence of angiogenesis research on management of patients with breast cancer," *Breast Cancer Res. Treat.*, 36(2):109-118, 1995.

Folkman, "Antiangiogenic therapy," In: *Cancer: Principles and Practice of Oncology*, Lippincott-Raven Publishers, pp. 3075-3085, 1997.

Gooneratne et al., "An investigation of the effects of invvenous administration of thiomolybdate on copper metabolism in chronic Cu-poisoned sheep," *Br. J. Nutr.*, 46:469, 1981.

Gooneratne et al., "Intravenous administration of thiomolybdate for the prevention and treatment of chronic copper poisoning in sheep," *Br. J. Nutr.*, 46:457, 1981.

Gross et al., "Inhibition of basic fibroblast growth factor-induced angiogenesis and glioma tumor growth in vivo in copper depleted rats," *Proceedings of the American Association for Cancer Research*, 32:57, Abstract 338, 1991.

Gullino, "Considerations on the mechanism of the angiogenic response," *Anticancer Res.*, 6(2):153-158, 1986.

Hadjikyriacou and Coucouvanis, "New members of the $[Mo^2(S)n(S_2)_{6-n}]^{2-}$ series. Synthesis, structural characterization, and properties of the $[Mo_2S_9]^{2-}$, $[Mo_2S_7]^{2-}$ and $[Mo_2S_6]^{2-}$ thioanions," *Inorg. Chem.*, 26:2400-2408, 1987.

Hill et al., "Treatment of Wilson's Disease with Zinc II. Validation of Oral $^{64}$Copper Uptake with Copper Balance," *Am. J. Med. Sci.*, 12:344, 1986.

Hill et al., "Treatment of Wilson's disease with zinc, I: oral zinc therapy regimens," *Hepatology*, 7:522-528, 1987.

Hourani and Demopoulos, "Inhibition of S-91 mouse melanoma metastases and growth by D-penicillamine," *Laboratory Investigation*, 21(5):434-438, 1969.

Kanatzidis and Coucouvanis, "Structure of Bis(tetraethylammonium) tetrathiomolybdte(VI), $2C_8H_{20}N^+ MoS_4^{2-}$," *Acta Cryst.*, C39:835-838, 1983.

Lee et al., "The Treatment of Wilson's Disease with Zinc VII. Protection of the Liver for Copper Toxicity by Zinc Induced Metallothionein in a Rat Model," *J. Lab. Clin. Med.*, 114:639-645, 1989.

Marshall et al., "Phase I trial of orally administered pentosan polysulfate in patients with advanced cancer," *Clin. Cancer Res.*, 3:2347-2354, 1997.

Merajver et al., "Copper depletion as an anti-angiogenic strategy in HER2-neu transgenic mice," *Proceedings of Special AACR Conference on Angiogenesis and Cancer*, Abstract #B-11, Jan. 22-24, 1998.

Mills et al., "Effects of molybdate, sulfide, and tetrathiomolybdate on copper metabolism in rats," *J. Inorg. Biochem.*, 14:189, 1981.

Mills et al., "Copper and molybdenum absorption by rats given ammonium tetrathiomolybdate," *J. Inorg. Biochem.*, 14: 163, 1981.

Parke et al., "Characterization and quantification of copper sulfate-induced vascularization of the robbit cornea," *Am. J. Pathol.*, 130:173-178, 1988.

Patstone and Maher, "Copper and calcium binding motifs in the extracellular domains of fibroblast growth factor receptors," *J. Biol. Chem.*, 271:3343-3346, 1996.

Raju et al., Ceruloplasmin, copper Ions, and angiogenesis, *J. Natl. Cancer Inst.*, 69:1183-1188, 1982.

Schapira and Schapira, "Use of ceruloplasmin levels to monitor response to therapy and predict recurrence of breast cancer," *Breast Cancer Res Treat.*, 3:223-224, 1983.

Schuschke et al., "Short-term dietary copper deficiency does not inhibit angiogenesis in tumours implanted in striated muscle," *Br. J. Cancer*, 66:1059-1064, 1992.

Shing, "Heparin-copper biaffinity chromatography of fibroblast growth factors," *J. Biol. Chem.*, 263:9059-9062, 1988.

Teo et al., "Mo, W, and Fe EXAFS of the $[Cl_2FeS_2MS_2FeCl_2]^{2-}$ (M=Mo, W) dianions. A comparison with the Mo EXAFS of nitrogenase," *J. Am. Chem. Soc.*, 105:5767-5770, 1983.

Yoshida et al., "Copper chelation inhibits tumor angiogenesis in the experimental 9L gliosarcoma model," *Neurosurgery*, 37(2):287-292, 1995.

Yoshida et al., "Suppression of 9L gliosarcoma growth by copper depletion with copper-deficient diet and D-penicillamine," *J. Neurooncol.*, 17(2):91-97, 1993.

Yuzbasiyan-Gurkan et al., "Treatment of Wilson's Disease with Zinc V. Changes in Serum Levels of Lipase, Amylase and Alkaline Phosphatase in Wilson's Disease Patients," *J. Lab. Clin. Med.*, 114:520-526, 1989.

Yuzbasiyan-Gurkan et al., "The Treatment of Wilson's Disease with Zinc X. Intestinal Metallothionein Induction," *J. Lab. Clin. Med.*, 120:380-386, 1992.

Zagzag, "The effects of copper depletion on intracerebral angiogenesis and growth of experimental brain tumors," *Dissertation Abstracts International*, 53(12B):6160, 1988.

Ziche et al., "Role of Prostaglandin $E_1$ and Copper in Angiogenesis," *J. Natl. Cancer Inst.*, 69:475-482, 1982.

Benjamin et al., "Selective Ablation of Immature Blood Vessels in Established Human Tumors Follows Vascular Endothelial Growth Factor Withdrawal," *J. Clin. Invest.*, 103(2):159-165, 1999.

Borgstrom et al., "Neutralizing Anti-Vascular Endothelial Growth Factor Antibody Completely Inhibits Angiogenesis and Growth of Human Prostate Carcinoma Micro Tumors In Vivo," *The Prostate*, 35:1-10, 1998.

Jeannin et al., "Molecular Architecture of Copper(1) Thiometallate Complexes. Examples of a Cubane with an Extra Face, $(NPr_4)_3[MS_4Cu_4Cl_5]$," *Inorganic. Chimica. Acta.*, 198-200:493-500, 1992.

Malavé et al., "Influence of Inoculation Site on Development of the Lewis Lung Carcinoma and Suppressor Cell Activity in Syngenic Mice," *J. Natl. Cancer Inst.*, 62(1):83-88, 1979.

Passaniti et al., "Methods in Laboratory Investigation," *Laboratory Investigation*, 67(4)519-528, 1992.

Sécheresse et al., "Heterobimetallic Aggregates of Copper(I) with Thio-tungstate and—molybdate. Cation Effect in Aggregation of $Ms_4Cu_4Cl_5$ Units, a Crystallographic Study," *J. Chem. Soc. Dalton Trans.*, 11:2875-2881, 1991.

Sugiura et al., "Studies in a Tumor Spectrum," *Cancer Research*, 15:38-51, 1955.

Takai et al., "Preparation, Structure and Properties of Mixed-Metal Trinuclear Complex: $(Pr_4N)_2[MoO(WS_4)_2]$," *Chemistry Letters*, 8:645-646, 1996.

Bajou et al., "Absence of Host Plasminogen Activator Inhibitor I Prevents Cancer Invasion and Vascularization," *Nat. Med.*, 4:923-928, 1998.

Bamba et al., "Release Mechanisms in Gel Forming Sustained Release Preparations," *Int. J. Pharm.*, 2:307, 1979.

Blood et al., "Tumor Interactions With the Vasculature: Angiogenesis and Tumor Metastasis", *Biochim. Biophys. Acta.*, 1032:89-118, 1990.

Brown, "Metal Toxicity and Therapeutic Intervention," Biochem. Soc. Trans., 30:742-745 2002.

Brown, "Copper and Prion Disease," *Brain Res. Bull.*, 55:165-173, 2001.

Carri et al., "Copper-Dependent Oxidative Stress, Alteration of Signal Transduction and Neurodegeneration in Amyothophic Lateral Sclerosis," *Funct. Neurol.*, 16:181-188, 2001.

Chakravarty et al., "Serum Copper in Malignant Neoplasia with Special Reference to the Cervix Uteri," *J. Cancer Res. Clin. Oncol.*, 108: 312-315, 1984.

Chambers et al., "Macrophage Colony-Stimulating Factor Mediates Invasion of Ovarian Cancer Cells Through Urokinase," *Cancer Research*, 55:1578-1585, 1995.

Chen et al., "TNF-R1 Signaling: A Beautiful Pathway," *Science*, 296: 1634-1635, 2002.

Crowley et al., "Prevention of Metastasis by Inhibition of the Urokinase Receptor," *Proc. Nat'l. Acad. Sci. USA*, 90:5021-5025, 1993.

During et al., "Controlled Release of Dopamine from a Polymeric Brain Implant; In vivo Characterization," *Ann. Neurol.*, 25:351-356, 1989.

Folkman, "Anti-Angiogenesis: New Concept for Therapy of Solid Tumors," *Ann. Surg.*, 175: 409-416, 1972.

Folkman, "Angiogenesis Inhibitors Generated by Tumors," *Mol. Med.*, 1(2):120-122 1995.

Gnjec et al., "Transition Metal Chelator Therapy—A potential Treatment For Alzheimer's Disease?" *Front Biosci.*, 16-23, 2002.

Goodson, "Medical Applications of Controlled Release" 2:115-138, 1984.

Gorelik et al., "Control of Lung Metastasis Progression in Mice: Role of Growth Kinetics of 3LL Lewis Lung Carcinoma and Host Immune Reactivity," *J. Nat'l. Cancer Inst.*, 65: 1257-1264, 1980.

Gorelik, et al., "Host's Immune State and Kinetics of Local Tumor Growth Control-Progression of Postoperative Lung Metastasis," *Rec. Results Cancer Res.*, 75:20-28, 1980.

Hanada et al., "Regulation of Cytokine Signaling and Inflammation," *Cytokine Growth Factor Rev.*, 13:413-421, 2002.

Hanahan et al., "Patterns and Emerging Mechanisms of the Angiogenic Switch During Tumorigenesis," *Cell*, 86(3)35; 364, 1996.

Hilgard et al., "Oral Anticoagulation in the Treatment of a Spontaneously Metastasising Murine Tumour (3LL)," *Br. J. Cancer*, 35;78-86, 1977.

Howard et al., "Intracerebral Drug Delivery in Rats with Lesion-Induced Memory Deficits," *J. Neurosurg.*, 71:105-112, 1989.

Isakov et al., "An Immune Response Against the Alloantigens of the 3LL Lewis Lung Carcinoma Prevents the Growth of Lung Metastases, but Not of Local Allografts," *Invasion Metas.*, 2:12-32, 1982.

Kleinman et al., "Basement Membrane Complexes with Biological Activity," *Biochem.*, 25: 312-318, 1986.

Koch et al., "Interleukin-8 as a Macrophage-Derived Mediator of Angiogenesis," *Science*, 258:1798-1801, 1992.

Kowalik-Jankowska et al., "Possible Involvement of Copper (II) in Alzheimer Disease," *Environ. Health Perspect.*, 5:869-870, 2002.

Langer et al., "Chemical and Physical Structure of Polymers as Carriers for Controlled Release of Bioactive Agents: A Review," *J. Macromol. Sci. Rev. Macromol. Chem.*, 23:61-126, 1983.

Langer, "New Methods of Drug Delivery," *Science*, 249:1527-1533, 1990.

Levy et al., Inhibition of Calcification of Bioprosthetic Heart Valves by Local Controlled-Release Diphosphonate, *Science*, 228:190-192, 1985.

Llanos et al., "The Molecular Basis of Copper Homeostasis and Copper-Related Disorders," *DNA Cell Biol.*, 21:259-270, 2002.

Loskutoff et al., "A Powerful Genetic Model to Study Hemostatic Gene Expression in Obesity/NIDDM," *Ann. N.Y. Acad. Sci.*, 902:272-282, 2000.

Malave et al., "Influence of Inoculation Site on Development of the Lewis Lung Carcinoma and Suppressor Cell Activity in Syngeneic Mice," *J. Nat'l. Cancer Inst.*, 62:83-88, 1979.

Mandinov et al., "Copper Chelation Represses the Vascular Response To Injury" *PNAS*, 100:6700-6705, 2003.

Maynard et al., "Overexpression of Alzheimer's Disease Amyloid-β Opposes the Age-Dependent Elevations of Brain Copper and Iron," *J. Biol. Chem.*, 277(47):44670-44676, 2002.

Millauer et al., "Dominant-Negative Inhibition of Flk-1 Suppresses the Growth of Many Tumor Types In vivo," *Cancer Res.*. 56:1615-1620, 1996.

Min et al., "Urokinase Receptor Antagonists Inhibit Angiogenesis and Primary Tumor Growth in Syngeneic Mice," *Cancer Res.*, 56:2428-2433, 1996.

Miyake et al., "Transforming Growth Factor-β1 Stimulates Contraction of Human Glioblastoma Cell-Mediated Collagen Lattice Through Enhanced α2 Integrin Expression," *J. Neuropathol. Exp. Neurol.*, 59:18-28, 2000.

Nguyen et al., "Quantitation of Angiogenesis and Antiangiogenesis in the Chick Embryo Chorioallantoic Membrane," *Microvascular Res.*, 47:31-40, 1994.

Odedra et al., "Low Molecular Weight Angiogenesis Factors," *Pharmac. Ther.*, 49:111-124, 1991.

Osawa et al., "Tumor Necrosis Factor Alpha-Induced Interleukin-8 Production via NF-kB and Phosphatidylinositol 3-Kinase/Akt Pathways Inhibits Cell Apoptosis in Human Hepatocytes," *Infect. Immun.*, 70:6294-6301, 2002.

Pan et al., "Copper Deficiency Induced by Tetrathiomolybdate Suppresses Tumor Growth and Angiogenesis," *Cancer Res.*, 62: 4854-4859, 2002.

Parish et al., "A Basement-Membrane Permeability Assay Which Correlates with the Metastatic Potential of Tumor Cells," *Int. J. Cancer*, 52:378-383, 1992.

Parke et al., "Characterization and Quantification of Copper Sulfate-Induced Vascularization of the Rabbit Cornea" *Am. J. Pathol.*, 130:173-178, 1988.

Passaniti et al., "A Simple, Quantitative Method for Assessing Angiogenesis and Antiangiogenic Agents Using Reconstituted Basement Membrane, Heparin, and Fibroblast Growth Factor," *Lab. Invest.*, 67:519-528, 1992.

Patstone et al., "Copper and Calcium Binding Motifs in the Extracellular Domains of Fibroblast Growth Factor Receptors," *J. Biol. Chem.*, 271(7):3343-3346, 1996.

Perry et al., "The Role of Iron and Copper in the Aetiology of Neurodegenerative Disorders," *CNS Drugs*, 16:339-352, 2002.

Rabbani et al., "Prevention of Prostate-Cancer Metastasis In Vivo By a Novel Synthetic Inhibitor of Urokinase-Type Plasminogen Activator (uPA)," *Int. J. Cancer*, 63:840-845, 1995.

Redman et al., "Phase II Trial of Tetrathiomolybdate in Patients with Advanced Kidney Cancer," *Clin. Cancer Res.*, 9:1666-1672, 1966.

Rupnick et al., "Adipose Tissue Mass Can Be Regulated Through the Vasculature," *Proc. Natl. Acad. Sci.*, 99:10730-10735, 2002.

Saudek et al., "A Preliminary Trial of the Programmable Implantable Medication System for Insulin Delivery," *N. Engl. J. Med.*, 321:574, 1989.

Schnaper et al., "Plasminogen Activators Augment Endothelial Cell Organization In Vitro by Two Distinct Pathways," *J. Cell. Physiol.*, 165:107-118, 1995.

Sefton, "Implantable Pumps," *CRC Crit. Rev. Biomed. Eng.*, 14(3):201-240, 1987.

Sen et al., "Copper-Induced Vascular Endothelial Growth Factor Expression and Wound Healing," *Am. J. Physiol. Heart Circ. Physiol.*, 282:H1821-H1827, 2002.

Shockley et al., "Penetration of Tumor Tissue by Antibodies and Other Immunoproteins," *Ann. N.Y. Acad. Sci.*, 617:367-382, 1991.

Strausak et al., "Copper in Disorders with Neurological Symptoms: Alzheimer's, Menkes, and Wilson Diseases," *Brain Res. Bull.*, 55:175-185, 2001.

Talmadge et al., "Enhanced Metastatic Potential of Tumor Cells Harvested From Spontaneous Metastases of Heterogeneous Murine Tumors," *J. Nat'l. Cancer Inst.*, 69:975-980, 1982.

Thakur et al., "Indium-III-Labeled Leukocytes for the Localization of Abscesses: Preparation, Analysis, Tissue Distribution, and Comparison with Gallium-67 Citrate in Dogs," *J. Lab. Clin. Med.*, 89:217-228, 1977.

Treat et al., in "Liposomes in the Therapy of Infectious Disease and Cancer," Lopez-Berestein and Fidler (eds.), Liss, New York, 353-365, 1989.

Van Golen et al., "Suppression of Tumor Recurrence and Metastasis by a Combination of the PHSCN Sequence and the Antiangiogenic Compound Tetrathiomolybdate in Prostate Carcinoma," *Neoplasia*, 4(5):373-379, 2002.

Verma et al., "Osmotically Controlled Oral Drug Delivery," *Drug Develop. Indus. Pharm.*, 26(7):695-708, 2000.

Verschoyle et al., "Pharmacokinetics of Isotretinoin (ISO) in Rats Following Oral Dosing or Aerosol Inhalation," *British J. Cancer*, 80, Suppl. 2, 96, 1999.

Volpert et al., "Captopril Inhibits Angiogenesis and Slows the Growth of Experimental Tumors in Rats," *J. Clin. Invest.*, 98:671-679, 1996.

Xing et al., "Overexpression of Urokinase Receptor in Breast Cancer Cells Results in Increased Tumor Invasion, Growth and Metastasis," *Int. J. Cancer*, 67:423-429, 1996.

International Search Report for PCT/US03/003210, mailed Dec. 18, 2003.

International Search Report for PCT/US03/23031, mailed Jun. 29, 2004.

\* cited by examiner

METHODS AND COMPOSITIONS FOR THE TREATMENT OF ANGIOGENIC DISEASES

The present application is a continuation of U.S. patent application Ser. No. 09/389,435, filed Sep. 3, 1999, now U.S. Pat. No. 6,703,050 which claims the priority date of provisional application Ser. No. 60/099,103, filed Sep. 4, 1998, and provisional application Ser. No. 60/101,759, filed Sep. 25, 1998, the entire disclosures of which are incorporated herein by reference without disclaimer.

The government owns rights in the present invention pursuant to grant number FD-U-000505 from the Food and Drug Administration, and grant number RO3-CA77122-01 from the National Institutes of Health.

BACKGROUND OF THE INVENTION

1. Field of the Invention

The present invention relates generally to the fields of disease prophylaxis and therapy. More particularly, it concerns agents that can bind to copper, in certain aspects forming a tripartite complex with protein, and the use of these agents in the prevention and treatment of diseases with a vascular component, such as cancer. Compositions and methods for combination therapy of these diseases, as well as therapeutic kits, are also provided.

2. Description of Related Art

Solid tumors require blood vessel proliferation (angiogenesis) for sustained growth in order to maintain adequate nutrition to other than the most peripheral cell layers (Hayes, 1994; Horak et al., 1993; Parangi et al., 1996). Normal adult human tissues, on the other hand, require little new blood vessel growth, except for wound repair, regeneration following trauma or surgery, and proliferation of the inner lining of the uterus during the menstrual cycle. Thus, dependency on angiogenesis is a fundamental difference between tumor and normal tissue. This difference is quantitatively more striking than the differences in cell replication and cell death rates, on which many cytoreductive chemotherapies depend. As a result of tumor dependency on angiogenesis, the concept of anti-angiogenic therapy for malignancies was developed (Folkman, 1995a; Folkman, 1995b; Hanahan and Folkman, 1996).

Copper is both a requirement and a potent stimulus for angiogenesis, as shown by studies of neovascularization in the rabbit cornea (Parke et al., 1988). During prostaglandin E1 (PGE1)-induced angiogenesis in the rabbit cornea, copper accumulates at the site where angiogenesis occurs (Parke et al., 1988). Conversely, in copper deficient rabbits, angiogenesis in the rabbit cornea in response to PGE1 is greatly reduced. In the rabbit cornea, copper for angiogenesis can be supplied by ceruloplasmin (a copper protein) as well as by dissolved copper sulfate, while apoceruloplasmin (ceruloplasmin without copper) does not support angiogenesis (Gullino, 1986). Additional studies have also shown that copper is an important angiogenic agent (Raju et al., 1982; Ziche et al., 1982). These studies all support the concept that unbound copper is required for angiogenesis.

Several years ago, some animal tumor model studies were carried out using an anti-copper approach (Brem et al., 1990a; 1990b; Yoshida et al., 1995). The chelator penicillamine plus a low-copper diet were used to lower copper levels in rats and rabbits with implanted intracerebral tumors. However, the animals treated with the low-copper regimen, while showing reduction in tumor size, did not show improved survival over untreated controls.

Penicillamine therapy has also been reported to be associated with significant side effects, including nausea and abdominal discomfort, and more serious side effects such as leukopenia and thrombocytopenia, which can lead to aplastic anemia. Nephrotic syndrome has also been reported in certain instances.

There are numerous other examples of diseases characterized by aberrant angiogenesis. One example of such a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

There remains a need in the art for agents that effectively prevent, slow the onset or progression of, reduce or treat diseases characterized by angiogenesis, such as cancer, macular degeneration, and rheumatoid arthritis. The development of successful prophylactic or therapeutic agents that reduce the level of copper in vivo, without the side effects and risks associated with other copper reducing agents, would represent a particularly significant advance.

SUMMARY OF THE INVENTION

The present invention overcomes these and other deficiencies present in the art by providing methods and compositions that, in certain aspects of the invention, slow the onset or progression of or even prevent diseases characterized by aberrant vascularization or angiogenesis, such as cancer, and in other aspects of the invention, reduce or treat such diseases. This is accomplished by the provision of agents that reduce the level of copper in vivo, in preferred aspects through the formation of a tripartite agent-copper-protein complex. The compositions and methods of the present invention accomplish this without the side effects and risks associated with other copper reducing agents.

As used herein, the term "aberrant vascularization" or "aberrant angiogenesis" will be understood to include abnormal neovascularization, including the formation of new blood vessels, larger blood vessels, more branched blood vessels (intussusception), and any and all mechanisms that lead to inappropriate or increased blood carrying capacity to a diseased tissue or site. The agents of the present invention will be understood to counteract "aberrant vascularization" or "aberrant angiogenesis", irrespective of the actual mechanism of action.

The present invention provides a method of delaying the onset of or preventing cancer in an animal, comprising administering to an animal at risk for developing cancer a biologically effective amount of at least a first pharmaceutical composition comprising at least a first prophylactic agent that binds copper and forms an agent-copper-protein complex upon administration to the animal. The protein in the agent-copper-protein complex can be a food protein, or a serum protein, such as serum albumin. The present invention also provides a method of delaying the onset of or preventing cancer in a human subject, comprising administering to a human subject at risk for developing cancer a biologically effective amount of at least a first pharmaceutical composition comprising at least a first prophylactic agent that binds copper and forms an agent-copper-protein complex upon administration to the human subject.

The present invention also provides a method of delaying the onset of or preventing cancer in an animal or human subject, comprising selecting an animal or human subject at risk for developing cancer, and administering to the animal or human subject at risk for developing cancer a therapeutically effective amount of at least a first pharmaceutical composition comprising at least a first prophylactic agent that binds copper and forms an agent-copper-protein complex upon administration to the animal or human subject. The "selecting" step may be accomplished, e.g., by identifying relatives of cancer patients and/or identifying susceptible subjects by genetic testing.

In certain aspects of the invention, the at least a first agent is a thiomolybdate compound. Preferred thiomolybdate compounds for use in the present invention include, but are not limited to, dodecathiodimolybdate, tetrathiomolybdate, iron octathiodimolybdate, trithiomolybdate, dithiomolybdate or monothiomolybdate. In particularly preferred aspects of the invention, the at least a first agent is tetrathiomolybdate. In other embodiments of the invention, the thiomolybdate compound comprises at least a first iron atom and/or at least a first oxygen atom. It will be understood that complete oxidation of the thiomolybdate compound should preferably be avoided.

In other aspects of the invention, the thiomolybdate compound is associated with at least a first agent effective to form a stabilized thiomolybdate compound. Exemplary stabilizing agents are carbohydrate molecules, such as a monosaccharide, a disaccharide, a trisaccharide, an oligosaccharide or a polysaccharide. In preferred embodiments, the thiomolybdate compound is associated with at least a first sucrose molecule, such as forming a thiomolybdate compound associated with between about 5 and about 200 sucrose molecules, and in other preferred embodiments of the invention, the thiomolybdate compound is associated with about 30 sucrose molecules.

Thus, the present invention provides a method of delaying the onset of or preventing cancer in an animal, or in a human subject, comprising administering to the animal or subject a biologically effective amount of at least a first pharmaceutical composition comprising dodecathiodimolybdate, tetrathiomolybdate, iron octathiodimolybdate, trithiomolybdate, dithiomolybdate, monothiomolybdate or a carbohydrate-associated complex thereof. The invention also provides a method of delaying the onset of or preventing cancer in an animal, or in a human subject, comprising administering to the animal or subject a biologically effective amount of a pharmaceutical composition comprising tetrathiomolybdate.

The agents for use in the present invention, such as tetrathiomolybdate, lower copper levels by forming a "tripartite agent-copper-protein complex" that is subsequently cleared from the body. The copper bound in these "tripartite agent-copper-protein complexes" is not reversibly released from these complexes, and are thus distinguished from reversible bipartite copper chelation.

As used herein, the term "biologically effective amount" will be understood to mean an amount of an agent that binds copper and forms an agent-copper-protein complex effective to delay the onset of or prevent diseases associated with aberrant vascularization, preferably cancer, upon administration to selected animals or patients. Thus in the preventative aspects of the present invention, the term "prophylactically effective amount" can also be used to describe the amount of the instant compositions effective to delay the onset of or prevent diseases and/or cancer upon administration to selected animals or patients.

Alternatively, in the therapeutic aspects of the present invention, the term "therapeutically effective amount" can also be used to describe the amount of the instant compositions effective to delay the onset of or prevent cancer. In terms of cancer treatment, amounts are effective to slow the growth of a tumor; to stop the growth of a tumor; to specifically induce necrosis in at least a portion of a tumor; and/or to induce tumor regression or remission upon administration to selected animals or patients. Such effects are achieved while exhibiting negligible or manageable adverse side effects on normal, healthy tissues of the animal or patient. Thus, the "therapeutically effective amount" can vary from animal to animal or patient to patient, depending on a number of factors including, but not limited to, the extent of disease and the size of patient. All such dosing issues can be routinely addressed by the attending physician in light of the present disclosure.

The present invention further provides a method of treating an animal having at least a first tumor, comprising administering to the animal a biologically effective amount of at least a first pharmaceutical composition comprising at least a first agent that binds copper and forms an agent-copper-protein complex upon administration to the animal. Additionally, the present invention provides a method of treating a human patient having at least a first tumor, comprising administering to the patient a therapeutically effective amount of at least a first pharmaceutical composition comprising at least a first therapeutic agent that binds copper and forms an agent-copper-protein complex upon administration to the patient. In certain aspects of the invention, the at least a first agent is a thiomolybdate compound, such as dodecathiodimolybdate, tetrathiomolybdate, iron octathiodimolybdate, trithiomolybdate, dithiomolybdate, monothiomolybdate or a carbohydrate-associated complex thereof. In particularly preferred embodiments of the invention, the at least a first agent is tetrathiomolybdate. Thus, the present invention provides a method of treating an animal or a human patient having at least a first tumor, comprising administering to the patient a therapeutically effective amount of dodecathiodimolybdate, tetrathiomolybdate, iron octathiodimolybdate, trithiomolybdate, dithiomolybdate or monothiomolybdate. The present invention also provides a method of treating an animal or a human patient having at least a first tumor, comprising administering to the patient a therapeutically effective amount of tetrathiomolybdate. In various therapeutic embodiments of the present invention, the preferred at least a first agent is thus tetrathiomolybdate.

Thus, the present invention provides a method of prophylactic or therapeutic intervention in a human subject having or at risk for developing a tumor, comprising administering to the subject a prophylactically or therapeutically effective amount of at least a first agent that binds copper and forms an agent-copper-protein complex. The present invention further provides a method of prophylactic or therapeutic intervention in a human subject having or at risk for developing a tumor, comprising administering to the subject a prophylactically or therapeutically effective amount of dodecathiodimolybdate, tetrathiomolybdate, iron octathiodimolybdate, trithiomolybdate, dithiomolybdate or monothiomolybdate. The present invention additionally provides a method of prophylactic or therapeutic intervention in a human subject having or at risk for developing a tumor, comprising administering to the subject a prophylactically or therapeutically effective amount of tetrathiomolybdate. The present invention also provides a method of treating a human patient having a tumor, preferably a vascularized tumor, comprising selecting a patient that would benefit from copper-protein complexation, and administering a therapeutically effective amount of at least a first copper-complexing agent effective to form agent-copper-protein complexes in the patient.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore "an agent that binds copper and forms an agent-copper-protein complex" means "at least a first agent that binds copper and forms an agent-copper-protein complex". The operable limits and parameters of combinations, as with the amounts of any single agent, will be known to those of ordinary skill in the art in light of the present disclosure.

In certain aspects of the invention, the biologically effective amount of the at least a first agent is between about 20 mg and about 200 mg per patient. In certain aspects of the invention, the therapeutically effective amount of the at least a first agent is between about 20 mg and about 200 mg per patient over a therapeutically effective time or period. In general, the agent is administered to the patient daily, and thus in these embodiments of the invention, the biologically or therapeutically effective amount of the at least a first agent is between about 20 mg and about 200 mg per patient per day. "Between about 20 mg and about 200 mg" includes all values in this range, and thus includes amounts of about 25 mg, about 30 mg, about 40 mg, about 50 mg, about 60 mg, about 70 mg, about 75 mg, about 80 mg, about 90 mg, about 100 mg, about 100 mg, about 120 mg, about 125 mg, about 130 mg, about 140 mg, about 150 mg, about 160 mg, about 170 mg, about 180 mg, about 190 mg or about 195 mg. "About" will be understood to include values above and below the given number. Thus, "about 20 mg" will be understood to include about 18 mg, about 19 mg, about 21 mg and about 22 mg or so, and "about 200 mg" will be understood to include about 201 mg, about 202 mg, about 203 mg and about 204 mg or so.

In other embodiments of the invention, the biologically or therapeutically effective amount of the at least a first agent is between about 20 mg and about 190 mg, between about 20 mg and about 180 mg, between about 20 mg and about 170 mg, between about 20 mg and about 160 mg, between about 20 mg and about 150 mg, between about 20 mg and about 140 mg, between about 20 mg and about 130 mg, between about 20 mg and about 120 mg, between about 20 mg and about 110 mg, between about 20 mg and about 100 mg, between about 20 mg and about 90 mg, between about 20 mg and about 80 mg, between about 20 mg and about 70 mg, between about 20 mg and about 60 mg, between about 20 mg and about 50 mg, between about 20 mg and about 40 mg, between about 20 mg and about 30 mg, between about 30 mg and about 200 mg, between about 40 mg and about 200 mg, between about 50 mg and about 200 mg, between about 60 mg and about 200 mg, between about 70 mg and about 200 mg, between about 80 mg and about 200 mg, between about 90 mg and about 200 mg, between about 100 mg and about 200 mg, between about 110 mg and about 200 mg, between about 120 mg and about 200 mg, between about 130 mg and about 200 mg, between about 140 mg and about 200 mg, between about 150 mg and about 200 mg, between about 160 mg and about 200 mg, between about 170 mg and about 200 mg, between about 180 mg and about 200 mg, between about 190 mg and about 200 mg, between about 30 mg and about 190 mg, between about 40 mg and about 180 mg, between about 50 mg and about 170 mg, between about 60 mg and about 160 mg, between about 70 mg and about 150 mg, between about 80 mg and about 140 mg, between about 90 mg and about 130 mg, between about 100 mg and about 120 mg, between about 125 mg and about 200 mg or between about 150 mg and about 180 mg per patient per day.

These values can also be expressed in terms of mg/kg of body weight. As described above, the biologically or therapeutically effective amount can vary depending on the size of the animal or human patient. However, taking the average weight of a human male as about 70 kg, the biologically or therapeutically effective amount of the agent that binds copper and forms an agent-copper-protein complex for an average human male would be between about 0.3 mg/kg and about 3 mg/kg or so.

The compositions and methods of the present invention can be used to treat all forms of solid tumors having a vascular component, in particular those that are extensively vascularized, although this is not required in all aspects of the invention. Solid tumors, such as carcinomas and sarcomas, are exemplary of the types of tumors amenable to treatment with the instant compositions and methods. Particular examples of the types of tumors that may be prevented or treated using the present invention include, but are not limited to, renal, lung, breast, colon, prostate, stomach, liver, pancreas, esophagus, brain and larynx tumors, as well as angiosarcomas and chondrosarcomas.

Tumors of various sizes may also be treated using the present invention. Thus, small tumors, including metastatic tumors, exemplified by tumors that are about 1 cm in diameter or less, medium or moderate tumors, exemplified by tumors that are between about 1 cm and about 5 cm in diameter, and large tumors, exemplified by tumors that are about 5 cm in diameter or greater are contemplated for treatment using the present invention. In the context of the present invention, the term "a vascularized tumor" most preferably means a vascularized, malignant tumor, solid tumor or "cancer".

Since, as discussed above, the instant compositions and methods are not completely specific to any particular tumor type, patients having more than one type of tumor may also be treated by the present invention. Thus, patients having at least a first and at least a second distinct type of tumor, exemplified by, but not limited to, a breast tumor and a chondrosarcoma or a renal tumor and a lung tumor, at least three distinct types of tumors, at least four distinct types of tumors, at least five distinct types of tumors or more are contemplated for treatment using the present invention.

In certain preferred aspects of the present invention, the at least a first agent is administered to the patient orally. However, other routes of administration are contemplated, including, but not limited to, intravenous, intramuscular and subcutaneous injections, slow release formulations and the like.

In certain embodiments of the invention, the methods further comprise administering to the human subject a therapeutically effective amount of at least a second anti-cancer agent. Exemplary of the additional anti-cancer agents contemplated for use are chemotherapeutic agents, radiotherapeutic agents, distinct copper chelating agents, anti-angiogenic agents, apoptosis-inducing agents or zinc compounds. In further aspects of the present invention, the methods further comprise subjecting the patient to surgery or radiotherapy.

The at least a first anti-cancer agent may be a "chemotherapeutic agent". As used herein, the term "chemotherapeutic agent" is used to refer to a classical chemotherapeutic agent or drug used in the treatment of malignancies. This term is used for simplicity notwithstanding the fact that other compounds, including immunotoxins, may be technically described as a chemotherapeutic agent in that they exert an anti-cancer effect. However, "chemotherapeutic" has come to have a distinct meaning in the art and is being used according to this standard meaning. "Chemotherapeutics" in the context of the present application therefore do not generally refer to immunotoxins, radiotherapeutic agents and such like, despite their operational overlap.

A number of exemplary chemotherapeutic agents are listed in Table 1. Those of ordinary skill in the art will readily understand the uses and appropriate doses of chemotherapeutic agents, although the doses may well be reduced when used in combination with the present invention. A new class of drugs that may also be termed "chemotherapeutic agents" are agents that induce apoptosis. Any one or more of such drugs, including genes, vectors and antisense constructs, as appropriate, may also be used in conjunction with the present invention.

In certain aspects of the present invention, the methods comprise administering a therapeutically effective amount of a zinc compound to the animal or human subject. In preferred embodiments, the methods comprise administering the at least a first agent to the animal or human subject in an amount and for a time effective to reduce the level of copper in the animal or human subject to about 20% of the level of copper in the animal or human subject prior to administration of the at least a first agent, and administering to the animal or human subject a therapeutically effective amount of a zinc compound, such as zinc acetate. In yet other preferred aspects, the therapeutically effective amount of a zinc compound is administered to the animal or human subject for a period of time effective to maintain the level of copper in the animal or human subject at about 20% of the level of copper in the animal or human subject prior to administration of the at least a first agent.

The present invention also provides methods of treating cancer in a human subject, comprising administering a pharmaceutical composition comprising tetrathiomolybdate to a human subject having cancer in an amount and for a time effective to reduce the level of copper in the human subject to about 20% of the level of copper in the human subject prior to administration of tetrathiomolybdate, and administering to the human subject a pharmaceutical composition comprising a therapeutically effective amount of a zinc compound.

The present invention also provides methods of treating or preventing a disease characterized by aberrant vascularization in an animal or a human patient, comprising administering to an animal or a human patient having or at risk for developing a disease characterized by aberrant vascularization a therapeutically effective amount of at least a first pharmaceutical composition comprising at least a first agent that binds copper and forms an agent-copper-protein complex. In preferred embodiments of the invention, the disease is cancer, wet type macular degeneration or rheumatoid arthritis.

Further provided by the present invention are methods of treating or preventing wet type macular degeneration in an animal or human patient, comprising administering to an animal or human patient having or at risk for developing wet type macular degeneration a therapeutically effective amount of at least a first pharmaceutical composition comprising at least a first agent that binds copper and forms an agent-copper-protein complex. In certain aspects of the invention, the at least a first agent is a thiomolybdate compound, such as dodecathiodimolybdate, tetrathiomolybdate, iron octathiodimolybdate, trithiomolybdate, dithiomolybdate, monothiomolybdate, or a carbohydrate-associated complex of any of the foregoing.

Additionally, the present invention provides methods of treating or preventing rheumatoid arthritis in an animal or human patient, comprising administering to an animal or human patient having or at risk for developing rheumatoid arthritis a therapeutically effective amount of at least a first pharmaceutical composition comprising at least a first agent that binds copper and forms an agent-copper-protein complex. In preferred aspects of the invention, the at least a first agent is a thiomolybdate compound, such as dodecathiodimolybdate, tetrathiomolybdate, iron octathiodimolybdate, trithiomolybdate, dithiomolybdate, monothiomolybdate, or a carbohydrate-associated complex of any of the foregoing.

The present invention also provides a composition, or a pharmaceutical composition, comprising a combined therapeutic amount of at least a first agent that binds copper and forms an agent-copper-protein complex and at least a second anti-cancer agent. In certain aspects of the invention, the at least a first agent is a thiomolybdate compound, such as dodecathiodimolybdate, tetrathiomolybdate, iron octathiodimolybdate, trithiomolybdate, dithiomolybdate, monothiomolybdate, or a carbohydrate-associated complex thereof. In preferred aspects of the invention, the at least a first agent that binds copper and forms an agent-copper-protein complex is tetrathiomolybdate. In further preferred embodiments, the at least a second anti-cancer agent is a chemotherapeutic agent, a radiotherapeutic agent, a distinct copper chelating agent, an anti-angiogenic agent, an apoptosis-inducing agent or a zinc compound. Thus, the present invention also provides a composition comprising a combined therapeutic amount of dodecathiodimolybdate, tetrathiomolybdate, iron octathiodimolybdate, trithiomolybdate, dithiomolybdate or monothiomolybdate and at least a second anti-cancer agent. The present invention additionally provides a composition comprising a combined therapeutic amount of tetrathiomolybdate and at least a second anti-cancer agent. Pharmaceutical compositions comprising a thiomolybdate compound associated with at least a first carbohydrate molecule are also provided.

Also provided is a therapeutic kit comprising, in at least a first suitable container, a therapeutically effective combined amount of at least a first agent that binds copper and forms an agent-copper-protein complex, and at least a second anti-cancer agent. In certain aspects of the invention, the at least a first agent is a thiomolybdate compound, such as dodecathiodimolybdate, tetrathiomolybdate, iron octathiodimolybdate, trithiomolybdate, dithiomolybdate or monothiomolybdate. In a preferred embodiment of the therapeutic kits of the present invention, the at least a first agent that binds copper and forms an agent-copper-protein complex is tetrathiomolybdate. In other aspects of the invention, the thiomolybdate compound is associated with at least a first carbohydrate molecule. In additional aspects of the therapeutic kits of the invention, the at least a second anti-cancer agent is a chemotherapeutic agent, a radiotherapeutic agent, a distinct copper chelating agent, an anti-angiogenic agent, an apoptosis-inducing agent or a zinc compound. In particular embodiments of the present invention, the at least a first agent that binds copper and forms an agent-copper-protein complex and the at least a second anti-cancer agent are comprised in at least a first and at least a second separate containers.

The present invention also provides therapeutic kits comprising, in at least a first suitable container, a therapeutically effective combined amount of dodecathiodimolybdate, tetrathiomolybdate, iron octathiodimolybdate, trithiomolybdate, dithiomolybdate, monothiomolybdate, or a carbohydrate-associated complex thereof, and at least a second anti-cancer agent. Further provided are therapeutic kits comprising, in at least a first suitable container, a therapeutically effective combined amount of tetrathiomolybdate and at least a second anti-cancer agent.

The present invention additionally provides compositions comprising a thiomolybdate compound associated with at least a first stabilizing molecule, such as a carbohydrate molecule, or a "thiomolybdate-carbohydrate complex". In certain aspects of the invention, the thiomolybdate compound comprises at least a first iron residue and/or at least a first oxygen residue. In other aspects, the ratio of carbohydrate molecules, or sugar units, to the thiomolybdate compound is between about 200 to 1 and about 5 to 1. It will be understood that all ratios within this range are also included, such as ratios of about 190 to 1, about 180 to 1, about 175 to 1, about 170 to 1, about 160 to 1, about 150 to 1, about 140 to 1, about 130 to 1, about 125 to 1, about 120 to 1, about 110 to 1, about 100 to 1, about 90 to 1, about 80 to 1, about 75 to 1, about 70 to 1, about 60 to 1, about 50 to 1, about 40 to 1, about 30 to 1, about 25 to 1, about 20 to 1, about 15 to 1 and about 10 to 1. In preferred aspects of the invention, the ratio of carbohydrate molecules to the thiomolybdate compound is about 30 to 1.

In further embodiments of the present invention, the at least a first carbohydrate molecule is a monosaccharide. In other aspects, the at least a first carbohydrate molecule is a disaccharide, such as sucrose. In yet other aspects, the at least a first carbohydrate molecule is an oligosaccharide. In certain embodiments, the thiomolybdate compound is associated with at least a first and at least a second distinct carbohydrate molecule.

The thiomolybdate compound may be non-covalently bonded to the at least a first stabilizing agent, e.g., carbohydrate molecule, such as by hydrogen bonding. In other aspects of the invention, the thiomolybdate compound is covalently bonded to at least a first stabilizing agent, e.g., carbohydrate molecule. In still other aspects, the thiomolybdate compound is complexed with the at least a first carbohydrate molecule. In preferred aspects, the thiomolybdate compound is dodecathiodimolybdate, tetrathiomolybdate, iron octathiodimolybdate, trithiomolybdate, dithiomolybdate or monothiomolybdate. In particularly preferred aspects, the thiomolybdate compound is tetrathiomolybdate. In further aspects, the compositions comprises a zinc compound. In other preferred aspects, the composition is dispersed in a pharmaceutically acceptable excipient. The present invention thus provides stabilized tetrathiomolybdate compositions comprising tetrathiomolybdate associated with about 30 sucrose molecules.

The agents that bind copper and form an agent-copper-protein complex, as described herein, can be used in treating or preventing a disease characterized by aberrant vascularization, including, but not limited to, cancer, wet type macular degeneration or rheumatoid arthritis. Use of the agents that binds copper and forms an agent-copper-protein complex in the manufacture of medicaments for treating or preventing a disease characterized by aberrant vascularization, including, but not limited to, cancer, wet type macular degeneration or rheumatoid arthritis, are thus also provided.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5A. Patient required decrease in dose at 2 time points 60 days apart. In order to prevent the Cp from falling below 5 mg/d, this patient will likely require a decrease in TM dose in the future. FIG. 5B. TM dose was increased after day 100 to prevent a drifting of the Cp above target range. Heterogeneity of diet and tumor behavior (such as tumor cell lysis) may account for the individual variability in dose adjustment needs.

DESCRIPTION OF ILLUSTRATIVE EMBODIMENTS

Figure 1:
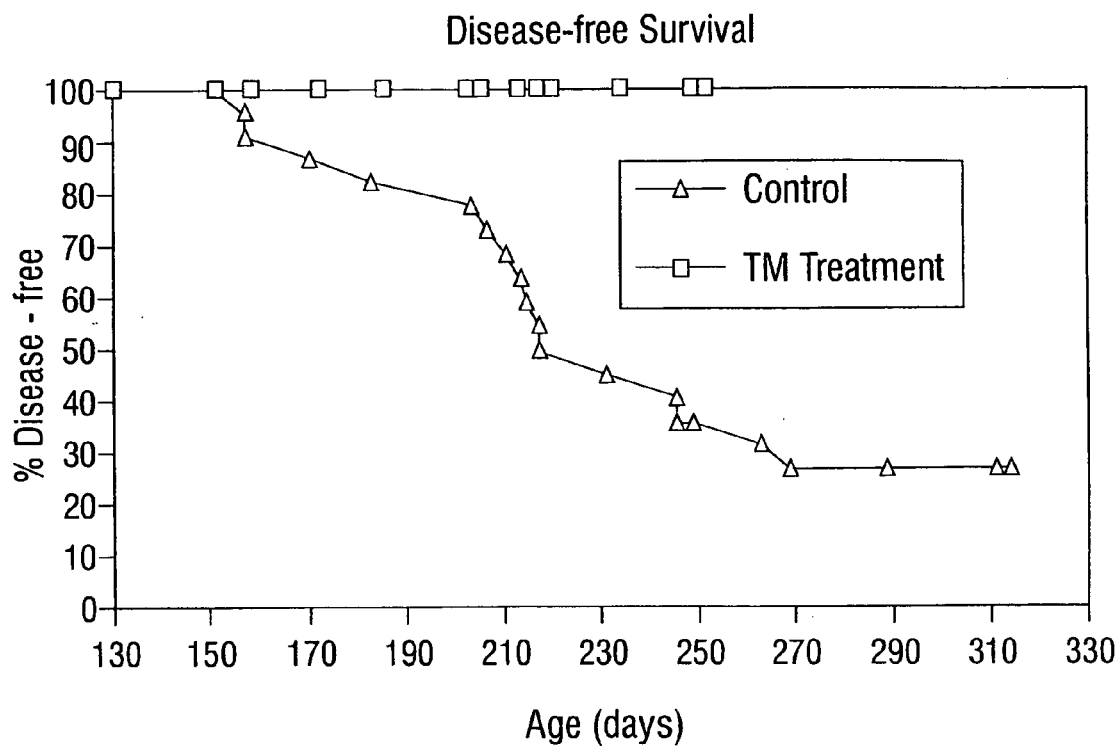
FIG. 1. Disease-free survival of TM-treated and control animals as a function of age. Daily TM treatments begun for each animal at approximately 100 days of age. Treatment (□) and control (Δ) groups are genetically identical cancer prone HER2-neu transgenic mice. Percentage of animals that are disease free is shown on the vertical axis, age in days is shown on the horizontal axis.

Solid tumors account for more than 90% of all cancers in man (Shockley et al., 1991). The therapeutic uses of monoclonal antibodies and immunotoxins have been investigated in the therapy of lymphomas and leukemias (Lowder et al., 1987; Vitetta et al., 1991), but have been disappointingly ineffective in clinical trials against solid tumors (Byers and Baldwin, 1988; Abrams and Oldham, 1985).

A principal reason for the ineffectiveness of antibody-based treatments is that macromolecules are not readily transported into solid tumors (Sands, 1988; Epenetos et al., 1986). Even when these molecules get into the tumor mass, they fail to distribute evenly due to the presence of tight junctions between tumor cells (Dvorak et al., 1991), fibrous stroma (Baxter et al., 1991), interstitial pressure gradients (Jain, 1990) and binding site barriers (Juweid et al., 1992).

All too often in cancer control, a high-functioning individual is coping with the high likelihood of a clinical cancer diagnosis or the inexorable progression of largely asymptomatic cancer to a lethal stage. At the cellular level, in spite of the diversity of the clinical settings, the incipient and existing tumors will all require new blood vessel growth or angiogenesis to affect the quality of life of their hosts. Therefore, the development of successful anti-angiogenic therapies may have the effect of preventing an emerging tumor from becoming clinically relevant, or may allow a prolonged asymptomatic state with stable metastatic disease. In addition, such therapy may also have the effect of down-staging overt tumors.

It has been known since the 1970's that copper is a co-factor in angiogenesis. Many key angiogenic mediators such as FGF, angiogenin, and SPARC bind or interact with copper in their pro-angiogenic state. The concept of anti-angiogenic treatment for solid tumors (Folkman, 1972; 1995c; 1997), has a firm rationale and shows efficacy in animal tumor models (Volpert et al., 1996; Millauer et al., 1996; Warren et al., 1995; Borgstom et al., 1996; 1998; Yuan et al., 1996; O'Reilly et al., 1997; Benjamin et al., 1999 and Merajver et al., 1998). Compounds that interfere with critical steps in the angiogenesis cascade are reaching the clinic (Marshall et al., 1997). The steps required for successful tumor angiogenesis at the primary and metastatic sites are diverse, and they depend on an imbalance between angiogenesis activators (Iruela-Arispe and Dvorak, 1997; Hanahan and Folkman, 1996) such as VEGF and bFGF, and inhibitors such as thrombospondin-1 (TSP-1) (Volpert et al., 1995; Salnikow et al., 1997; Guo et al., 1997; Schapira and Schapira, 1983; Qian et al., 1997), angiostatin, (O'Reilly et al., 1994; Lannutti et al., 1997; Sim et al., 1997) and endostatin (O'Reilly et al., 1997). The relative importance of the different angiogenesis modulating molecules in different tissues may determine the relative potency of anti-angiogenic compounds to elicit a response both at the primary and metastatic sites.

It has been amply demonstrated that copper is required for angiogenesis (Parke et al., 1988; Raju et al., 1982; Ziche et al., 1982). Brem et al. (1990a, b), and more recently Yoshida et al. (1995) attempted to use an anti-copper approach in the treatment of tumors in animal studies. They have used a copper deficient diet combined with penicillamine therapy, called CDPT. The studies showed relative inhibition of growth of rabbit VX2 carcinoma in the rabbit brain (Brem et al., 1990b) and rat 9L gliosarcoma in the rat brain (Brem et al., 1990a, Yoshida et al., 1995) as a result of such treatment, but, significantly, reported no improvement in overall survival. The animals in Yoshida et al. were sacrificed before overall survival could be assessed. In the Brem et al. studies, death was due to accompanying intracerebral edema, which was severe enough in treated animals to cause death at the same rate as the untreated tumor did in control animals. Furthermore, in contrast to the rabbit brain model, CDPT failed to inhibit tumor growth and vascularization of the VX2 carcinoma in the thigh muscle and in metastases to lung. The lack of improvement in survival in brain tumor implant models and the lack of effect in non-brain tumors seems to have discouraged further work in this area.

The inventors reasoned that it would be very desirable to develop an anti-angiogenic strategy that would affect multiple activators of angiogenesis, in order for it to be generally applicable to human tumors. Many anti-angiogenic proposals are directed against a single target. Since copper is a required co-factor for the function of many key mediators of angiogenesis, such as bFGF (Watanabe et al., 1990; Engleka and Maciag, 1994; Shing, 1988; Patstone and Maher, 1996), VEGF, and angiogenin (Badet et al., 1989), the inventors developed an anti-angiogenic strategy for the treatment of cancer and other diseases characterized by aberrant angiogenesis based on the modulation of total-body copper status. The underlying basis of this work is that a window of copper deficiency exists in which angiogenesis is impaired, but other copper dependent cellular processes are not affected enough to cause clinical toxicity. The inventors have succeeded in their clinical objectives, despite the documented failures of others using animal models.

The development of safe and effective prophylactic or therapeutic agents that reduce the level of copper in vivo has been an ongoing problem in the art. The inventors hypothesis of an anti-copper, anti-angiogenic approach to cancer therapy is that the level of copper required for angiogenesis is higher relative to that required for essential copper dependent cellular functions, such as heme synthesis, cytochrome function, and incorporation of copper into enzymes and other proteins. The inventors reasoned that the unique and favorable characteristics of tetrathiomolybdate (TM) as an anti-copper agent, compared to other anti-copper drugs, could make TM a non-toxic, efficacious new weapon in an anti-copper, anti-angiogenic therapy.

As described in detail below, for the past 20 years the inventors have developed new anti-copper therapies for Wilson's disease, an autosomal recessive disease of copper transport that results in abnormal copper accumulation and toxicity. One of the drugs currently being used is TM, which shows unique and desirable properties of fast action, copper-specificity, and low toxicity (Brewer et al., 1991a; 1994b; 1996), as well as a unique mechanism of action. TM forms a stable tripartite complex with copper and protein. If given with food, it complexes food copper with food protein and prevents absorption of copper from the gastrointestinal tract. There is endogenous secretion of copper in saliva and gastric secretions associated with food intake, and this copper is also complexed by TM when it is taken with meals, thereby preventing copper re-absorption. Thus, patients are placed in a negative copper balance immediately when TM is given with food. If TM is given between meals, it is absorbed into the blood stream, where it complexes either free or loosely bound copper with serum albumin. This TM-bound copper fraction is no longer available for cellular uptake and has no known biological activity.

The studies of the present invention indeed show TM to be a safe and effective anti-cancer agent. TM showed efficacy in impairing the development of de novo mammary tumors in Her2-neu transgenic mice (Example 2), and showed no clinically overt toxicity as copper levels were decreased to 10% of baseline. The present disclosure also details the first human trial of an anti-copper approach to anti-angiogenesis therapy based on the use of tetrathiomolybdate in patients with metastatic cancer (Examples 3 and 4). The phase I trial of TM, yielding information on dose, dose response, evaluation of copper status in patients, toxicity and efficacy, is surprisingly beneficial, particularly in light of the disappointing animal studies conducted by others (Brem et al., 1990a, b; Yoshida et al., 1995). Novel approaches to following disease status in trials of anti-angiogenric compounds are also disclosed.

I. Agents that Form a Tripartite Complex with Copper and Protein

A. Tetrathiomolybdate

1. Characterization and Mechanism of Action

Tetrathiomolybdate (TM) is a compound made up of molybdenum atom surrounded by four sulfido groups. Discovery of the biological effects of TM began with observations on cattle and sheep, in which they developed copper deficiency when grazing on pasturages with high molybdenum (Mo) content (Ferguson et al., 1943; Dick and Bull, 1945; Miller and Engel, 1960). It was established that administration of supplementary Mo impaired copper metabolism in ruminants (Macilese Ammerman et al., 1969); however, Mo had little effect on non-ruminant animals such as rats (Mills et al., 1958; Cox et al., 1960). The answer to this puzzle came from observations which suggested that the Mo was converted to thiomolybdates in the rumen as a result of the high sulfide metabolism there, and that thiomolybdates were the active anti-copper agents (Dick et al., 1975). This theory was confirmed when thiomolybdate compounds were given to rats and produced anti-copper effects (Mills et al., 1981a, b; Bremner et al., 1982). The tetrathio-substituted compound, TM, is the most potent of these.

The anti-copper mechanism of action of TM is two fold (Mills et al., 1981a, b; Bremner et al., 1982; Gooneratne et al., 1981b). One mechanism operates in the GI tract, the second in the blood. In the GI tract, TM forms complexes with copper and food proteins (or other proteins), that are not absorbed. This absorption block involves not only food copper, but also the rather considerable amount of endogenously secreted copper in saliva, gastric juice and other GI tract secretions (Allen and Solomons, 1984). TM is a more effective blocker of copper absorption than zinc, since zinc acts only in those areas. of the small intestine where metallothionein can be induced (Yuzbasiyan-Gurkan et al., 1992). In contrast, TM works all up and down the GI tract. The other advantage of TM over zinc in this setting is that TM acts immediately. It does not have a lag period required for the induction of metallothionein.

The second effect of TM is on the blood. TM given at times away from meals is relatively well absorbed into the blood. There it forms complexes with copper and albumin, rendering the complexed copper unavailable for cellular uptake (Gooneratne et al., 1981b). The normal plasma copper is in two primary pools. Most of the plasma copper in normal persons is part of the ceruloplasmin molecule. This copper is essentially unavailable for ready exchange with cells and is considered non-toxic. The other pool of copper is more loosely bound to albumin and small molecules, such as amino acids. This pool of copper is greatly expanded during acute copper toxicity in diseases such as Wilson's disease, and is readily available for cellular uptake and is, therefore, potentially toxic (Scheinberg and Sternlieb, 1984). When TM enters the blood it complexes with this latter copper and renders it, like the ceruloplasmin copper, unavailable for cellular uptake and for further toxicity.

Very good evidence exists that TM-complexed copper is unavailable for cellular uptake. The most direct evidence is that in sheep levels of copper in the plasma which would normally be high enough to produce hemolytic anemia do not do so in the presence of TM (Gooneratne et al., 1981b). It was shown that the TM bound copper does not permeate the erythrocyte. This is direct evidence that TM-complexed copper does not permeate cells.

TM and salts of TM are available; one of the preferred salts of TM is the ammonium salt. TM as purchased from Aldrich Chemical Company (catalog number W180-0; Milwaukee, Wis.), is a black powder that is moderately water soluble, yielding a bright red solution. TM purchased from Aldrich Chemical Company (available in one kilogram bulk lots) is certified pure for human use. The bulk drug should be stored in the absence of oxygen, or the oxygen will gradually exchange with the sulfur, rendering the drug ineffective over time. The bulk drug is therefore stored under argon. Stability assays developed by the inventors indicate that the drug is stable for several years under argon (Brewer et al., 1991a). Capsules can be filled by hand, and the drug is stable in capsules for several months at room temperature.

TM acts by forming a tripartite complex with copper and protein (Mills et al., 1981a, b; Bremner et al., 1982). TM has two mechanisms of action. Given with meals, it complexes copper in food and endogenously secreted copper with itself and food protein, and prevents the absorption of copper. Patients can be put into an immediate negative copper balance with TM by administering it with meals. Given between meals, the TM is absorbed into the bloodstream, and complexes serum copper with itself and albumin, rapidly rendering the copper unavailable for cellular uptake. Since free copper in organs is in equilibrium with free copper of blood, free copper in the organs, and in tumor tissue, will quickly be reduced to very low levels, if the blood copper is bound. This complex is cleared through the kidney and the liver. TM is the most potent and most rapidly acting anti-copper agent known.

2. TM Toxicity and Efficacy

Tetrathiomolybdate (TM) is a drug that the inventors have developed as an orphan therapy for Wilson's disease. The drug does an excellent job of gaining quick control over copper toxicity and preventing the neurological worsening that occurs 50% of the time during initial treatment with a commonly used drug for Wilson's disease, penicillamine (Brewer et al., 1991a; Brewer et al., 1994b; Brewer et al., 1996). So far, the inventors have treated 55 Wilson's disease patients with TM, generally for an eight week period. TM thus fills a very important niche in the initial treatment of Wilson's disease. The Wilson's disease work has provided extensive experience with TM in the human, and has helped to document TM's extremely low level of toxicity in humans.

In human Wilson's disease studies, the one side effect occasionally observed is a reversible anemia, due to TM's anti-copper effects. Given in too high a dose, TM renders the bone marrow severely or totally copper deficient. Since copper is required for erythropoiesis, an anemia develops. That anemia is rapidly reversible by simply stopping TM. In the Wilson's disease studies, the overtreatment effect of TM has been diminished by simply reducing the dose to 20 mg six times per day. In humans without Wilson's disease, such as cancer patients, a level of mild copper deficiency at a pre-anemia state can be established simply by carefully monitoring ceruloplasmin (Cp) levels during TM therapy.

TM is eventually metabolized to thiomolybdates, molybdates and molybdenum oxides, so the potential toxicity of these compounds have to be considered. However, it turns out that these molybdenum compounds are quite innocuous at the levels produced from breakdown of TM used in the clinical situations described herein. About 37% of TM by weight is Mo, so in the studies described herein, up to 50 mg of Mo/day is administered for two weeks then no more than about 25 mg/day for maintenance. High doses of 350 to 1400 mg/day of Mo were previously used for 4-11 months in patients with Wilson's disease, without toxicity (Bickel et al., 1957). Thus, the dose range of 25-50 mg/day poses no predictable problems, and should be entirely safe.

Considerable work on the potential toxicity of TM has been carried out in rats (Mills et al., 1981a; Bremner et al., 1982). At approximately 6 mg of TM per kilogram of diet rats show substantial effects on copper, including a reduction of plasma ceruloplasmin and a reduction in liver and kidney copper. At approximately 12 mg of TM all of these changes were increased and, in addition, liver Mo was increased. Mild anemia was present, and skeletal lesions were present in one of six animals. At 18 mg of TM the anemia was severe. Melanogenesis of hair was impaired, diarrhea was present, growth rate was markedly impaired, and all animals had skeletal lesions characterized by dysplasia in the epiphyseal cartilage cells of long bones, resorption of trabecular bone, and structural changes in ligaments.

It was later shown that all of the toxic effects of TM, up to 36 mg of TM per kilogram of diet, could be prevented by oral supplementation with copper, or with intraperitoneal injection of copper (Mills et al., 1981b). Thus, it appears that all the toxic lesions induced by TM are due to copper deficiency induced by the TM. In support of this, almost all of the above lesions are induced by dietary copper deficiency, the two exceptions being the skeletal lesions and the enterocyte mitochondrial damage which leads to diarrhea. The reason that these last two lesions are seen with TM administration, but may not be seen in dietary copper deficiency, could be related to the severity and the rapidity of the copper deficiency induced by TM. With dietary copper deficiency there is always some contaminating copper available, and rapidly dividing cells such as the enterocyte and epiphyseal cells may obtain enough copper to prevent the lesions. The prevention of these two lesions as well as all of the other TM induced lesions by copper supplementation indicates that the lesions are probably due to copper deficiency.

Another group has examined gut pathology in rats receiving approximately 18 mg of TM per kilogram of diet (Fell et al., 1979). These rats also received approximately 3 mg of copper per kilogram of diet. These scientist found gut pathology involving cell apoptosis, edema, and necrosis which they did not attribute to hypocuprosis, although this was not proven. It is probable that a higher copper supplement was required for protection, in view of the finding that all such problems were prevented by adequate copper supplementation (Mills et al., 1981b).

Wilson's disease patients have a huge store of excess copper, so none of the TM toxicities due to copper deficiency are a risk in these patients. Even in the case of the skeletal and enterocyte lesions, since copper administration protected, the Wilson's disease patient with excessive stores of copper should also be protected. Other workers have studied the effect of TM on copper loaded sheep (Gooneratne et al., 1981a). It is well known that sheep are quite susceptible to copper toxicity, usually developing hepatic failure and hemolytic anemia. The studies involved loading sheep dietarily with copper to the point of initiation of hepatic damage, then TM was given intravenously in doses of 50 or 100 mg 2× weekly for up to 11 weeks.

Five of the 26 sheep died during the study. All deaths were attributed to copper toxicosis based on autopsy results. 3 of the 5 deaths occurred in controls that received copper but not TM. One death occurred after an animal had received only one dose of TM, and another in a animal that had received only 4 doses. It is clear that these 2 animals died from copper toxicity prior to the ability of TM to rescue them. If animals survived the initial onset of copper toxicosis, they were protected from further copper toxicity by TM, even though in some cases copper administration was continued. These animals tolerated up to 22 injections of TM without clinical problems.

Support for the beneficial effect of either IV (Humphries et al., 1986) or subcutaneous (Humphries et al., 1988) TM in protecting sheep against severe hepatic copper toxicity has also been shown. TM not only reduced the amount of hepatic copper, but the actual liver damage. TM was also used prophylactically to prevent copper toxicity in commercial sheep flocks. Over 400 animals have been treated with TM with no adverse side effects (Humphries et al., 1988).

Preliminary work also indicated that TM may be dramatically effective against copper toxicity in the LEC rat model (Suzuki et al., 1993). The genetic defect on these rats has been recently shown to be due to a defect in the Wilson's disease gene (Wu et al., 1994). The rats develop severe liver disease and usually die. TM has been very effective in treating these animals in the late stages of their liver disease.

Mo metabolism in sheep has been studied after the IV injection of $^{99}$Mo labeled TM (Mason et al., 1983). There was a rapid plasma disappearance over 15 minutes and then a slow disappearance with a $t_{1/2}$ of about 40 h. The TM was transformed step wise to molybdate and over 90% was excreted in urine compared to 5% in feces. The same group published subsequently on $^{99}$Mo and $^{35}$S metabolism after IV injection of double labeled TM in sheep (Hynes et al., 1984). Most of the $^{99}$Mo and $^{35}$S were associated initially with albumin. Displaced or unbound TM was rapidly hydrolyzed to molybdate and sulfate. There was no evidence of an irreversible interaction of either $^{35}$S or $^{99}$Mo with copper and plasma despite the appearance of a TCA insoluble copper fraction.

It is clear that in the presence of high levels of copper, TM administration results in the accumulation of copper complexed with TM in both the liver and kidneys (Jones et al., 1984; Bremner and Young, 1978). However, there is no evidence of a storage disease associated with this complex. Current theory holds that the complex is disassociated and that the TM is metabolized to oxymolybdates and excreted (Mason et al., 1983). The copper then enters other pathways in the liver. In the presence of high levels of metallothionein it would most likely be taken up by metallothionein. In the kidneys the evidence is that the copper is simply excreted.

Two cases of reversible bone marrow depression have been reported in patients receiving TM for maintenance therapy (Harper and Walshe, 1986). The inventors have seen reversible anemia in seven patients. These patients had a strong response to therapy, and likely ended up with localized, bone marrow, copper deficiency. Since copper is required for heme synthesis, this appears to be a manifestation of over-treatment, at least as far as the bone marrow is concerned. Since TM is such an effective anti-copper agent, during maintenance therapy with TM as in the cases of Harper and Walshe (Harper and Walshe, 1986), it would not be unexpected for over-treatment to occur.

3. Molybdenum (Mo) Toxicity

About 37% of TM is Mo. The normal intake of Mo is about 350 μg/day (Seelig, 1972), or the equivalent amount of Mo that would be in about 1.0 mg of TM. Molybdenum seems to be quite well tolerated by the human. Relatively high doses of 5-20 mg/kg/day of Mo (equivalent to the Mo in 1-4 g of TM) were used for 4-11 months in patients with Wilson's disease in a 1957 study, without known toxicity (Bickel et al., 1957). However, it was not effective, because as pointed out earlier, TM is the active metabolite, and that is formed efficiently from Mo only in ruminants.

B. Other Thiomolybdate Compounds

Other thiomolybdate compounds that have a similar mode of action in free copper reduction include dodecathiodimolybdate, trithiomolybdate, dithiomolybdate and monothiomolybdate. These compounds, like tetrathiomolybdate, form a tripartite complex with copper and protein that renders the copper unavailable, and eventually leads to clearance of the copper-complex.

The synthesis and characterization of a number of thiomolybdate complexes, oxo/thiomolybdate complexes and heterometallic complexes containing iron, molybdenum and sulfur, with or without oxygen, have been described (Coucouvanis, 1998; Coucouvanis et al., 1989; Coucouvanis et al., 1988; Hadjikyriacou and Coucouvanis, 1987; Coucouvanis et al., 1984; Teo et al., 1983; Coucouvanis et al., 1983; Kanatzidis and Coucouvanis, 1983; Coucouvanis et al., 1981; Coucouvanis, 1981; Coucouvanis et al., 1980a, b). These complexes have been shown to bind to copper, and are thus contemplated for use in certain embodiments of the invention.

Among the preferred thiomolybdate compounds or complexes are those comprising one, two or three molybdenum atom(s), one molybdenum atom and one iron atom, two molybdenum atoms and one iron atom, and one molybdenum atom and two iron atoms. The structures of three general classes of thiomolybdate compounds, and two of the preferred thiomolybdate compounds, are shown below:

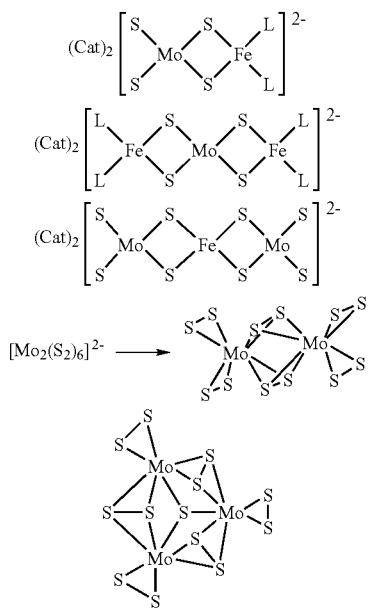

where Cat is a cation that makes the complex water soluble, for example $NH_4^+$, L is a ligand such as $Cl^-$ or R-Ph-S, where R is a functional group that makes the complex water soluble, such as a sulfonate, and Ph is a phenyl group.

Examples of the thiomolybdate complexes contemplated for use in the present invention include, but are not limited to, nonathiomolybdate ($[MoS_9]^{2-}$), hexathiodimolybdate ($[Mo_2S_6]^{2-}$), heptathiodimolybdate ($[Mo_2S_7]^{2-}$), octathiodimolybdate ($[Mo_2S_8]^{2-}$), nonathiodimolybdate ($[Mo_2S_9]^{2-}$), decathiodimolybdate ($[Mo_2S_{12}]^{2-}$), undecathiodimolybdate ($[Mo_2S_{11}]^{2-}$), dodecathiodimolybdate ($[Mo_2S_{12}]^{2-}$), the ammonium salt of dodecathiodimolybdate (($NH_4)_2[Mo_2(S_2)_6]$; Muller et al., 1980; Muller and Krickemeyer, 1990), the ammonium salt of tridecathiotrimolybdate (($NH_4)_2[Mo_3(S)(S_2)_6]$; Muller and Krickemeyer, 1990), and those thiomolybdates with an $[FeCl_2S_2MoS_2FeCl_2]^{2-}$, $[S_2MoS_2FeS_2MoS_2]^{3-}$, and $[S_2MoS_2FeCl_2]^{2-}$ core structures.

Additionally, the inventors have discovered that iron gluconate is a source of iron that does not contain halide ions. Its reaction with tetrathiomolybdate in the presence of ammonium hydroxide produces another preferred thiomolybdate compound, the novel ammonium salt of iron octathiodimolybdate (($NH_4)_3[S_2MoS_2FeS_2MoS_2]$), which is very water soluble.

While certain of these compounds may be less potent in reducing copper levels in the body than tetrathiomolybdate, they will nonetheless find utility, and in particular instances be preferred, in certain aspects of the present invention.

C. Stabilized Thiomolybdate Complexes

Thiomolybdate complexes are sensitive to oxidation when exposed to air. The inventors have discovered that by forming a complex between thiomolybdate compounds and carbohydrates, such as sucrose, that a stabilized form of the thiomolybdate compounds are produced. In these thiomolybdate-carbohydrate complexes, layers of carbohydrate molecules assemble around the thiomolybdate compound in arrays stabilized by hydrogen bonding. These layers serve to protect the thiomolybdate core against oxidation and hydrolysis. Other molecules, such as amino acids, that are capable of hydrogen bonding to the thiomolybdate compounds, are also contemplated for use in certain aspects of the invention.

The term "carbohydrate" embraces a wide variety of chemical compounds having the general formula $(CH_2O)_n$, and encompasses such compounds as monosaccharides, disaccharides, trisaccharides, oligosaccharides, polysaccharides and their aminated, sulfated, acetylated and other derivatized forms. Oligosaccharides are chains composed of sugar units, which are also known as monosaccharides. Sugar units can be arranged in any order and linked by their sugar units in any number of different ways. Therefore, the number of different stereoisomeric oligosaccharide chains possible is quite large.

As known in the art, a monosaccharide is a sugar molecule that contains one sugar unit. As used herein, the term "sugar unit" means a monosaccharide. As also known in the art, a disaccharide is a sugar molecule that contains 2 sugar units, a trisaccharide is a sugar molecule that contains 3 sugar units, an oligosaccharide is a sugar molecule that generally contains between about 2 and about 10 sugar units, and a polysaccharide is a sugar molecule that contains greater than 10 sugar units. The sugar units in a di-, tri- and oligosaccharide are all connected by glycosidic linkages. Nonetheless, as used in the present invention, the term "oligosaccharide" means a sugar molecule that contains at least two sugar units.

Within the scope of the present invention, "monosaccharides" will be understood as including, but not being limited to, either the D- or L-isomers of trioses, aldopentoses, aldohexoses, aldotetroses, ketopentoses and ketohexoses. The mentioned compounds may also be in the form of lactones. Examples of an aldopentose include, but are not limited to, ribose, arabinose, xylose and lyose; examples of an aldohexose are allose, altrose, glucose, mannose, gulose, idose, galactose, talose, fucose and rhamnose. Examples of a ketopentose include, but are not limited to, ribulose and xylulose, examples of a tetrose include, but are not limited to, erythrose and threose, and examples of a ketohexose include, but are not limited to, psicose, fructose, sorbose or tagatose.

Examples of a disaccharide are trehalose, maltose, isomaltose, cellobiose, gentiobiose, saccharose, lactose, chitobiose, N,N-diacetylchitobiose, palatinose or sucrose. Examples of trisaccharides are raffinose, panose, melezitose or maltotriose. Examples of oligosaccharides are maltotetraose, maltohexaose or chitoheptaose. The term "carbohydrate" as used herein is also intended to embrace sugar alcohols, e.g., alditols such as mannitol, lactitol, xylitol, glycerol or sorbitol. Examples of polysaccharides include, but are not limited to, polydextrose and maltodextrin.

This stabilization is contemplated to be effective using any carbohydrate as defined herein, at ratios of between about 5 sugar units to about 100 or 200 sugar units or so per thiomolybdate metal center. This range will be understood to include all values within this range, such as ratios of about 10 sugar units per thiomolybdate metal center, about 20 sugar units per thiomolybdate metal center, about 25 sugar units per thiomolybdate metal center, about 30 sugar units per thiomolybdate metal center, about 40 sugar units per thiomolybdate metal center, about 50 sugar units per thiomolybdate metal center, about 60 sugar units per thiomolybdate metal center, about 70 sugar units per thiomolybdate metal center, about 75 sugar units per thiomolybdate metal center, about 80 sugar units per thiomolybdate metal center, about 90 sugar units per thiomolybdate metal center, about 110 sugar units per thiomolybdate metal center, about 125 sugar units per thiomolybdate metal center, about 150 sugar units per thiomolybdate metal center, about 175 sugar units per thiomolybdate metal center or about 190 sugar units per thiomolybdate metal center.

An example of such a stabilized thiomolybdate compound is tetrathiomolybdate stabilized by sucrose. To prepare the sucrose-ammonium tetrathiomolybdate complex, 25 grams of sucrose is dissolved in 20 ml of distilled water. 1 gram of ammonium tetrathiomolybdate (TM) is added and the mixture stirred under argon until the TM is solution. The water is then removed from the mixture by flash evaporation under high vacuum.

The resulting powder appears to be much more stable in open air than the pure TM. After 3 months of storage in an open dish, the sucrose powder retained 61% of the original drug as measured by the $OD_{467}$, while the TM stored under the same conditions retained only 5% of its original $OD_{467}$.

D. Monitoring Copper Levels

The serum ceruloplasmin, which is directly dependent upon liver copper status, is an accurate indicator of copper status. The dose of TM used in previous studies in rodents would average about 0.5 mg/day in rats of average weight. The inventors' studies in mice and rats, and the inventors' extensive experience in humans with Wilson's disease and in humans with cancer, indicate that 4 times that dose is required in rats to reduce serum ceruloplasmin to about 10% of normal which is the optimal criterion for low copper status in rodents. These concepts of optimal monitoring of Cu status and TM dosing were subsequently incorporated in the animal studies of TM described in Example 2.

Based on the studies herein, and the inventors experience with TM, reduction in the level of ceruloplasmin (Cp) to between about 40% and about 10% of the baseline value prior to treatment will result in at least some level of beneficial clinical anti-angiogenic effect. However, a reduction of Cp to a level of about 20% of the baseline value prior to treatment is preferred in most clinical indications.

II. Other Copper Chelating Agents

In certain aspects of the present invention, the inventors contemplate the use of zinc to achieve a low-copper status in cancer patients. The inventors have developed zinc as an anti-copper agent for Wilson's disease, and it was approved for this purpose in January 1997 by the United States Food and Drug Administration (FDA). Zinc acts by inducing metallothionein in the intestinal mucosal cell, thereby blocking copper absorption (Brewer and Yuzbasiyan-Gurkan, 1992a). Zinc too, is extremely safe. In studies now reaching 200 Wilson's disease patients, zinc in doses of 150 mg daily has produced no toxicity at all (Brewer and Yuzbasiyan-Gurkan, 1992a).

In general, zinc lowers copper levels more slowly than tetrathiomolybdate and other thiomolybdate compounds. However, due to the fact that zinc compounds are relatively inexpensive and easy to prepare, and their widespread availability, the use of zinc compounds is preferred in certain aspects of the present invention, both in achieving initial low-copper status, and in maintenance therapy once low-copper status has been achieved using other agents (discussed in greater detail below).

III. Combination Therapy

The methods of the present invention may be combined with any other methods generally employed in the treatment of the particular disease or disorder that the patient exhibits. For example, in connection with the treatment of solid tumors, the methods of the present invention may be used in combination with classical approaches, such as surgery, radiotherapy and the like. So long as a particular therapeutic approach is not known to be detrimental in itself, or counteracts the effectiveness of the TM therapy, its combination with the present invention is contemplated. When one or more agents are used in combination with the TM therapy, there is no requirement for the combined results to be additive of the effects observed when each treatment is conducted separately, although this is evidently desirable, and there is no particular requirement for the combined treatment to exhibit synergistic effects, although this is certainly possible and advantageous.

In terms of surgery, concurrent surgery during copper deficiency is not preferred since blood vessel growth is required for wound healing. However, as copper can be repleted within about 24 hours of discontinuing TM therapy, any surgical intervention may be practiced after copper repletion. TM therapy can then be reinstated after wound healing has been established, typically about 1-2 weeks following surgery. In connection with radiotherapy, any mechanism for inducing DNA damage locally within tumor cells is contemplated, such as γ-irradiation, X-rays, UV-irradiation, microwaves and even electronic emissions and the like. The directed delivery of radioisotopes to tumor cells is also contemplated, and this may be used in connection with a targeting antibody or other targeting means.

Cytokine therapy also has proven to be an effective partner for combined therapeutic regimens. Various cytokines may be employed in such combined approaches. Examples of cytokines include IL-1α, IL1β, IL-2, IL-3, IL-4, IL-5, IL-6, IL-7, IL-8, IL-9, IL-10, IL-11, IL-12, IL-13, TGF-β, GM-CSF, M-CSF, G-CSF, TNFα, TNFβ, LAF, TCGF, BCGF, TRF, BAF, BDG, MP, LIF, OSM, TMF, PDGF, IFN-α, IFN-β, IFN-γ. Cytokines are administered according to standard regimens, consistent with clinical indications such as the condition of the patient and relative toxicity of the cytokine.

A. Copper Chelating Agents

The inventors contemplate the use of zinc following achievement of a low-copper status in cancer patients in order to maintain a moderate copper-deficient state for the long-term. As discussed above, the inventors have developed zinc as an anti-copper agent for Wilson's disease, and it was approved for this purpose in January 1997 by the United States Food and Drug Administration (FDA). Zinc acts by inducing metallothionein in the intestinal mucosal cell, thereby blocking copper absorption (Brewer and Yuzbasiyan-Gurkan, 1992a). Zinc too, is extremely safe. In studies now reaching 200 Wilson's disease patients, zinc in doses of 150 mg daily has produced no toxicity at all (Brewer and Yuzbasiyan-Gurkan, 1992a).

1. Zinc

Zinc compounds, such as zinc acetate, are being used for the comprehensive treatment of Wilson's disease including initial treatment (Hoogenraad et al., 1978; Hoogenraad et al., 1979; Hoogenraad et al., 1987). However, zinc is not ideal for initial therapy (by itself) because it is rather slow acting. Thus, it takes approximately two weeks to achieve intestinal metallothionein induction and a negative copper balance (Yuzbasiyan-Gurkan et al., 1992). At the two week point, zinc immediately reverses the +0.54 mg daily (positive) copper balance these patients average, but the negative copper balance induced is rather modest, averaging −0.35 mg daily (negative) copper balance (Brewer et al., 1990; Brewer et al., 1993b). Due to this low rate of copper removal, it takes as long as six months of zinc therapy to bring urine copper and nonceruloplasmin plasma copper (the potentially toxic copper measured in the blood), down to subtoxic levels.

2. Penicillamine

Penicillamine is the drug that has been used the most, and is the best known. However, it should be the last choice for initial treatment of neurological patients because of the very high risk of making them neurologically worse (Brewer et al., 1987a; Glass et al., 1990; Brewer et al., 1994a). Another problem with penicillamine is that about a quarter to a third of patients develop an initial hypersensitivity syndrome, requiring significant interventions, such as temporarily stopping the drug and restarting it at a lower dose, usually with concurrent cortico-steroid administration. This is a somewhat frightening experience for patients who are already ill, and prevents the attending physician in the inventors' study from being blinded. Finally, there is a long list of other side effects that can occur with penicillamine during the first few weeks of therapy. These include bone marrow depression, proteinuria, and auto-immune disorders.

3. Trientine

Trientine acts by chelation and urinary excretion of copper (Walshe, 1982). A therapeutic dose (1,000-2,000 mg/day) usually produces only about half as much cupruresis as a similar dose of penicillamine. Nonetheless, trientine is capable of an initial production of a several mg negative copper balance, much greater than zinc. Typically, this 4-5 mg cupruresis decreases during the first few weeks of therapy to a more modest, but still substantial, 2-3 mg. Ingestion of copper is about 1 mg/day, with obligatory, non-urine losses of about 0.5 mg. Thus a cupruresis of 2-3 mg produces a negative copper balance of 1.5 to 2.5 mg/day.

Trientine is officially approved for use in patients intolerant of penicillamine therapy. Because of this, and because it was introduced much later than penicillamine, it has not been used and reported on very extensively. It has not had a formal toxicity study. It appears to have substantially less risk of side effects then penicillamine. An initial hypersensitivity problem has not been reported. It does cause proteinuria, after several weeks of use in about 20% of patients. It can also occasionally produce bone marrow depression and autoimmune abnormalities, although the latter is usually after prolonged use.

So far, trientine has not been reported to cause initial worsening in neurological patients, but its sole use in this type of patient is probably very limited. Anecdotally, the inventors have received patients in transfer who worsened on penicillamine, were switched briefly to trientine, and when they became worse (or failed to improve) were transferred to the inventors for TM therapy. In these kinds of patients it is impossible to know if trientine played any role in worsening. Theoretically, it could, because as with penicillamine, it mobilizes copper, producing a higher blood level to achieve urinary excretion. But whether this increased level of blood copper translates into increased brain levels, and increased neurotoxicity, is unknown.

B. Chemotherapeutic Combinations and Treatment

Irrespective of the mechanisms by which enhanced tumor destruction is achieved, the combined treatment aspects of the present invention have evident utility in the effective treatment of disease. To use the present invention in combination with the administration of a chemotherapeutic agent, one would simply administer to an animal an agent that binds copper and forms a tripartite agent-copper-protein complex in combination with the chemotherapeutic agent in a manner effective to result in their combined anti-tumor actions within the animal. These agents would therefore be provided in an amount effective and for a period of time effective to result in their combined presence within the tumor vasculature and their combined actions in the tumor environment. To achieve this goal, the agent that binds copper and forms a tripartite agent-copper-protein complex and chemotherapeutic agent may be administered to the animal simultaneously, either in a single composition or as two distinct compositions using different administration routes.

Alternatively, treatment with an agent that binds copper and forms a tripartite agent-copper-protein complex may precede or follow the chemotherapeutic agent treatment by intervals ranging from minutes to weeks. In embodiments where the chemotherapeutic factor and agent that binds copper and forms a tripartite agent-copper-protein complex are applied separately to the animal, one would generally ensure that a significant period of time did not expire between the time of each delivery, such that the chemotherapeutic agent and agent that binds copper and forms a tripartite agent-copper-protein complex would still be able to exert an advantageously combined effect on the tumor. In such instances, it is contemplated that one would contact the tumor with both agents within about 5 minutes to about one week of each other and, more preferably, within about 12-72 hours of each other, with a delay time of only about 12-48 hours being most preferred.

However, in some situations, it may be desirable to extend the time period for treatment significantly, where several days (2, 3, 4, 5, 6 or 7) or even several weeks (1, 2, 3, 4, 5, 6, 7 or 8) lapse between the respective administrations. Additionally, as described above, a preferred embodiment of the present invention is to administer the agent that binds copper and forms a tripartite agent-copper-protein complex between rounds of chemotherapy, or in a maintenance regimen after chemotherapy. Thus, it also is conceivable that more than one administration of either the agent that binds copper and forms a tripartite agent-copper-protein complex and/or the chemotherapeutic agent will be desired. To achieve tumor regression, both agents are delivered in a combined amount effective to inhibit its growth, irrespective of the times for administration.

A variety of chemotherapeutic agents are intended to be of use in the combined treatment methods disclosed herein. Chemotherapeutic agents contemplated as exemplary include, e.g., etoposide (VP-16), adriamycin, 5-fluorouracil (5FU), camptothecin, actinomycin-D, mitomycin C, carbaplatin, paclitaxel, docetaxel and even hydrogen peroxide. As will be understood by those of ordinary skill in the art, the appropriate doses of chemotherapeutic agents will be generally around those already employed in clinical therapies wherein the chemotherapeutics are administered alone or in combination with other chemotherapeutics.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Exemplary chemotherapeutic agents that are useful in connection with combined therapy are listed in Table 1. Each of the agents listed therein are exemplary and by no means limiting. The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

TABLE 1

Chemotherapeutic Agents Useful In Neoplastic Disease

| CLASS | TYPE OF AGENT | NONPROPRIETARY NAMES (OTHER NAMES) | DISEASE |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (L-sarcolysin) | Multiple myeloma, breast, ovary |
| | | Chlorambucil | Chronic lymphocytic leukemia, primary macroglobulinemia, Hodgkin's disease, non-Hodgkin's lymphomas |
| | Ethylenimenes and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; dimethyltriazenoimidazolecarboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU) | Breast, colon, stomach, pancreas, ovary, head and neck, urinary bladder, premalignant skin lesions (topical) |
| | | Floxuridine (fluorodeoxyuridine; FUdR) | |
| | | Cytarabine (cytosine arabinoside) | Acute granulocytic and acute lymphocytic leukemias |
| | Purine Analogs and Related Inhibitors | Mercaptopurine (6-mercaptopurine; 6-MP) | Acute lymphocytic, acute granulocytic and chronic granulocytic leukemias |
| | | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide Tertiposide | Testis, small-cell lung and other lung, breast, Hodgkin's disease, non-Hodgkin's lymphomas, acute granulocytic leukemia, Kaposi's sarcoma |
| | Antibiotics | Dactinomycin (actinomycin D) | Choriocarcinoma, Wilms' tumor, rhabdomyosarcoma, testis, Kaposi's sarcoma |
| | | Daunorubicin | Acute granulocytic and acute |

TABLE 1-continued

Chemotherapeutic Agents Useful In Neoplastic Disease

| CLASS | TYPE OF AGENT | NONPROPRIETARY NAMES (OTHER NAMES) | DISEASE |
|---|---|---|---|
| | | (daunomycin; rubidomycin) | lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia., Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essental thrombocytosis, malignant melanoma |
| | Methyl Hydrazine Derivative | Procarbazine (N-methylhydrazine, MIH) | Hodgkin's disease |
| | Adrenocortical Suppressant | Mitotane (o,p'-DDD) Aminoglutethimide | Adrenal cortex Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstilbestrol Ethinyl estradiol (other preparations available) | Breast, prostate |
| | Antiestrogen | Tamoxifen | Breast |
| | Androgens | Testosterone propionate Fluoxymesterone (other preparations available) | Breast |
| | Antiandrogen | Flutamide | Prostate |
| | Gonadotropin-releasing hormone analog | Leuprolide | Prostate |

C. Anti-Angiogenics

The term "angiogenesis" refers to the generation of new blood vessels, generally into a tissue or organ. Under normal physiological conditions, humans or animals undergo angiogenesis only in very specific restricted situations. For example, angiogenesis is normally observed in wound healing, fetal and embryonic development and formation of the corpus luteum, endometrium and placenta.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs during tumor metastasis. The agents of the invention that bind copper and form a tripartite agent-copper-protein complex may thus be used in combination with additional "anti-angiogenic" therapies. A preferred component for use in inhibiting angiogenesis is a protein named "angiostatin". This component is disclosed in U.S. Pat. Nos. 5,776,704; 5,639,725 and 5,733,876, each incorporated herein by reference. Angiostatin is a protein having a molecular weight of between about 38 kDa and about 45 kDa, as determined by reducing polyacrylamide gel electrophoresis, which contains approximately Kringle regions 1 through 4 of a plasminogen molecule. Angiostatin generally has an amino acid sequence substantially similar to that of a fragment of murine plasminogen beginning at amino acid number 98 of an intact murine plasminogen molecule.

The amino acid sequence of angiostatin varies slightly between species. For example, in human angiostatin, the amino acid sequence is substantially similar to the sequence of the above described murine plasminogen fragment, although an active human angiostatin sequence may start at either amino acid number 97 or 99 of an intact human plasminogen amino acid sequence. Further, human plasminogen may be used, as it has similar anti-angiogenic activity, as shown in a mouse tumor model.

Specific angiogenesis inhibitors, including, but not limited to, Anti-Invasive Factor, retinoic acids and paclitaxel (U.S. Pat. No. 5,716,981; incorporated herein by reference); AGM-1470 (Ingber et al., 1990; incorporated herein by reference); shark cartilage extract (U.S. Pat. No. 5,618,925; incorporated herein by reference); anionic polyamide or polyurea oligomers (U.S. Pat. No. 5,593,664; incorporated herein by reference); oxindole derivatives (U.S. Pat. No. 5,576,330; incorporated herein by reference); estradiol derivatives (U.S. Pat. No. 5,504,074; incorporated herein by reference); and thiazolopyrimidine derivatives (U.S. Pat. No. 5,599,813; incorporated herein by reference) are also contemplated for use as anti-angiogenic compositions for the combined uses of the present invention.

D. Apoptosis-Inducing Agents

The agents of the present invention that bind copper and form a tripartite agent-copper-protein complex may also be combined with treatment methods that induce apoptosis in any cells within the tumor, including tumor cells and tumor vascular endothelial cells. Although many anti-cancer agents may have, as part of their mechanism of action, an apoptosis-inducing effect, certain agents have been discovered, designed or selected with this as a primary mechanism, as described below.

A number of oncogenes have been described that inhibit apoptosis, or programmed cell death. Exemplary oncogenes in this category include, but are not limited to, bcr-abl , bcl-2 (distinct from bcl-1, cyclin D1 ; GenBank accession numbers M14745, X06487; U.S. Pat. Nos. 5,650,491; and 5,539,094; each incorporated herein by reference) and family members including Bcl-x1, Mcl-1, Bak, A1, A20. Overexpression of bcl-2 was first discovered in T cell lymphomas. bcl-2 functions as an oncogene by binding and inactivating Bax, a protein in the apoptotic pathway. Inhibition of bcl-2 function prevents inactivation of Bax, and allows the apoptotic pathway to proceed. Thus, inhibition of this class of oncogenes, e.g., using antisense nucleotide sequences, is contemplated for use in the present invention in aspects wherein enhancement of apoptosis is desired (U.S. Pat. Nos. 5,650,491; 5,539, 094; and 5,583,034; each incorporated herein by reference).

Many forms of cancer have reports of mutations in tumor suppressor genes, such as p53. Inactivation of p53 results in a failure to promote apoptosis. With this failure, cancer cells progress in tumorigenesis, rather than become destined for cell death. Thus, provision of tumor suppressors are also contemplated for use in the present invention to stimulate cell death. Exemplary tumor suppressors include, but are not limited to, p53, Retinoblastoma gene (Rb), Wilm's tumor (WT1), bax alpha, interleukin-1b-converting enzyme and family, MEN-1 gene, neurofibromatosis, type 1 (NF1), cdk inhibitor p16, colorectal cancer gene (DCC), familial adenomatosis polyposis gene (FAP), multiple tumor suppressor gene (MTS-1), BRCA1 and BRCA2.

Preferred for use are the p53 (U.S. Pat. Nos. 5,747,469; 5,677,178; and 5,756,455; each incorporated herein by reference), Retinoblastoma, BRCA1 (U.S. Pat. Nos. 5,750,400; 5,654,155; 5,710,001; 5,756,294; 5,709,999; 5,693,473; 5,753,441; 5,622,829; and 5,747,282; each incorporated herein by reference), MEN-1 (GenBank accession number U93236) and adenovirus E1A (U.S. Pat. No. 5,776,743; incorporated herein by reference) genes.

Other compositions that may be used include genes encoding the tumor necrosis factor related apoptosis inducing ligand termed TRAIL, and the TRAIL polypeptide (U.S. Pat. No. 5,763,223; incorporated herein by reference); the 24 kDa apoptosis-associated protease of U.S. Pat. No. 5,605,826 (incorporated herein by reference); Fas-associated factor 1, FAF1 (U.S. Pat. No. 5,750,653; incorporated herein by reference). Also contemplated for use in these aspects of the present invention is the provision of interleukin-1β-converting enzyme and family members, which are also reported to stimulate apoptosis.

Compounds such as carbostyril derivatives (U.S. Pat. Nos. 5,672,603; and 5,464,833; each incorporated herein by reference); branched apogenic peptides (U.S. Pat. No. 5,591,717; incorporated herein by reference); phosphotyrosine inhibitors and non-hydrolyzable phosphotyrosine analogs (U.S. Pat. Nos. 5,565,491; and 5,693,627; each incorporated herein by reference); agonists of RXR retinoid receptors (U.S. Pat. No. 5,399,586; incorporated herein by reference); and even antioxidants (U.S. Pat. No. 5,571,523; incorporated herein by reference) may also be used. Tyrosine kinase inhibitors, such as genistein, may also be linked to ligands that target a cell surface receptor (U.S. Pat. No. 5,587,459; incorporated herein by reference).

IV. Pharmaceutical Compositions and Kits

Pharmaceutical compositions of the present invention will generally comprise an effective amount of an agent that binds copper and forms a tripartite agent-copper-protein complex, such as tetrathiomolybdate, dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

A. Parenteral Formulations

The agents of the present invention that bind copper and form a tripartite agent-copper-protein complex, such as tetrathiomolybdate, will often be formulated for parenteral administration, e.g., formulated for injection via the intravenous, intramuscular, sub-cutaneous or other such routes, including direct instillation into a tumor or disease site. The preparation of an aqueous composition that contains one or more agents that bind copper and form a tripartite agent-copper-protein complex as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Compositions comprising the agents of the present invention that bind copper and form a tripartite agent-copper-protein complex, such as tetrathiomolybdate, can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. Formulations are easily administered in a variety of dosage forms, such as the type of injectable solutions described above, but drug release capsules and the like can also be employed.

Suitable pharmaceutical compositions in accordance with the invention will generally include an amount of one or more of the agents of the present invention that bind copper and form a tripartite agent-copper-protein complex, such as tetrathiomolybdate, admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

The therapeutically effective doses are readily determinable using an animal model, as shown in the studies detailed herein. Experimental animals bearing solid tumors are frequently used to optimize appropriate therapeutic doses prior to translating to a clinical environment. Such models are known to be very reliable in predicting effective anti-cancer strategies. For example, mice bearing solid tumors, such as used in Example 2, are widely used in pre-clinical testing. The inventors have used such art-accepted mouse models to determine working ranges of agents such as tetrathiomolybdate that give beneficial anti-tumor effects with minimal toxicity.

In addition to the compounds formulated for parenteral administration, such as intravenous or intramuscular injection, other pharmaceutically acceptable forms are also contemplated, e.g., tablets or other solids for oral administration, time release capsules, liposomal forms and the like. Other pharmaceutical formulations may also be used, dependent on the condition to be treated. For example, topical formulations may be appropriate for treating pathological conditions such as dermatitis and psoriasis; and ophthalmic formulations may be appropriate for conditions such as diabetic retinopathy. Of course, methods for the determination of optimal dosages for conditions such as these would be evident to those of skill in the art in light of the dosage optimization methodology disclosed in the instant specification, and the knowledge of the skilled artisan.

As described in detail herein, it is contemplated that certain benefits will result from the manipulation of the agents of the present invention that bind copper and form a tripartite agent-copper-protein complex, such as tetrathiomolybdate, to provide them with a longer in vivo half-life. Slow release formulations are generally designed to give a constant drug level over an extended period. Increasing the half-life of a drug, such as agents of the present invention that bind copper and form a tripartite agent-copper-protein complex, for example tetrathiomolybdate, is intended to result in high plasma levels upon administration, which levels are maintained for a longer time, but which levels generally decay depending on the pharmacokinetics of the construct. Although currently not preferred, slow release formulations of the instant compositions and combinations thereof are by no means excluded from use in the present invention.

B. Therapeutic Kits

The present invention also provides therapeutic kits comprising the agents of the present invention that bind copper and form a tripartite agent-copper-protein complex, such as tetrathiomolybdate, described herein. Such kits will generally contain, in suitable container means, a pharmaceutically acceptable formulation of at least one agent that binds copper and forms a tripartite agent-copper-protein complex, such as tetrathiomolybdate, in accordance with the invention. The kits may also contain other pharmaceutically acceptable formulations, such as any one or more of a range of chemotherapeutic drugs.

The kits may have a single container means that contains the agent that binds copper and forms a tripartite agent-copper-protein complex, such as tetrathiomolybdate, with or without any additional components, or they may have distinct container means for each desired agent. Certain preferred kits of the present invention include an agent that binds copper and forms a tripartite agent-copper-protein complex, such as tetrathiomolybdate, packaged in a kit for use in combination with the co-administration of a second anti-cancer agent, such as a chemotherapeutic agent, a radiotherapeutic agent, a distinct copper chelating agent, an anti-angiogenic agent or an apoptosis-inducing agent. In such kits, the components may be pre-complexed, either in a molar equivalent combination, or with one component in excess of the other; or each of the components of the kit may be maintained separately within distinct containers prior to administration to a patient.

When the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container means. One of the components of the kit may be provided in capsules for oral administration.

The container means of the kit will generally include at least one vial, test tube, flask, bottle, syringe or other container means, into which the agent that binds copper and forms a tripartite agent-copper-protein complex, such as tetrathiomolybdate, and any other desired agent, may be placed and, preferably, suitably aliquoted. Where additional components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the agent that binds copper and forms a tripartite agent-copper-protein complex, such as tetrathiomolybdate, to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

V. Cancer and Treatment

The compositions and methods provided by this invention are broadly applicable to the treatment of any malignant tumor having a vascular component. Typical vascularized tumors are the solid tumors, particularly carcinomas and sarcomas, which require a vascular component for the provision of oxygen and nutrients. Hematologic malignancies also appear to require angiogenesis for progression, and thus are also potentially amenable to treatment with the instant copper lowering agents. Exemplary solid tumors that may be treated using the invention include, but are not limited to, primary carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, sarcomas, such as angiosarcomas and chondrosarcomas, and the like. Metastatic tumors may also be treated using the methods and compositions of the present invention.

The present invention is contemplated for use in the treatment of any patient that presents with a solid tumor. However, in that the present invention is particularly successful in the treatment of solid tumors of moderate or large sizes, patients in these categories are likely to receive more significant benefits from treatments in accordance with the methods and compositions provided herein. In general, the invention can be used to treat tumors of about 0.3-0.5 cm and upwards, although tumors up to and including the largest tumors found in humans may also be treated.

In certain aspects of the present invention, the agents such as tetrathiomolybdate are intended as a preventative or prophylactic treatment and as a maintenance agent. There are many reasons underlying this aspect of the breadth of the invention. For example, a patient presenting with a primary tumor of moderate size or above may also have various other metastatic tumors that are considered to be small-sized or even in the earlier stages of metastatic tumor seeding. Given that TM and combinations of the invention are generally administered orally or into the systemic circulation of a patient, they will naturally have effects on the secondary, smaller and metastatic tumors, although this may not be the primary intent of the treatment. Furthermore, even in situations where the tumor mass as a whole is a single small tumor, certain beneficial anti-tumor effects will result from the use of the present treatments.

The guidance provided herein regarding the most suitable patients for use in connection with the present invention is intended as teaching that certain patient's profiles may assist with the selection of patients that may be treated by the present invention, or that may, perhaps, be better treated using other anti-cancer treatment strategies. Nonetheless, the fact that a preferred or otherwise more effective treatment is perceived to exist in connection with a certain category of patients, does not in any way negate the basic utility of the present invention in connection with the treatments of all patients having a vascularized tumor. A further consideration is the fact that the initial assault on a tumor, as provided by the therapy of the present invention, may be small in any measurable and immediate effects, but may sensitize or potentiate the tumor to further therapeutic treatments such that the subsequent treatment results in an overall synergistic effect or even leads to total remission or cure.

It is not believed that any particular type of tumor should be excluded from treatments using the present invention. It will be understood that the present methodology is widely or entirely applicable to the treatment of all solid tumors, irrespective of the particular phenotype or genotype of the tumor cells themselves. However, the type of tumor cells may be relevant to the use of the invention in combination with secondary therapeutic agents.

Those of ordinary skill in the art will understand that certain types of tumors may be more amenable to the induction of tumor stasis, regression, and even necrosis using the present invention. The phenomena is observed in experimental animals, and may occur in human treatments. Such considerations will be taken into account in conducting both the pre-clinical studies in experimental animals and in optimizing the doses for use in treating any particular patient or group of patients.

As detailed herein, there are realistic objectives that may be used as a guideline in connection with pre-clinical testing before proceeding to clinical treatment. However, this is more a matter of cost-effectiveness than overall usefulness, and is a mechanism for selecting the most advantageous compounds and doses. In regard to their basic utility, any construct or combination thereof that results in any consistent anti-tumor effects will still define a useful invention. It will also be understood that even in such circumstances where the anti-tumor effects of the instant compositions and combinations thereof are towards the low end of the range, it may be that this therapy is still equally or even more effective than all other known therapies in the context of the particular tumor targets. It is unfortunately evident to a clinician that certain tumors cannot be effectively treated in the intermediate or long term, but that does not negate the usefulness of the present therapy, particularly where it is about as effective as the other strategies generally proposed, or it may be effective after all other conventional strategies have failed. It is not predicted that resistance to this therapy can develop.

In designing appropriate doses of the agents that bind copper and form a tripartite agent-copper-protein complex, and combinations therewith, one may readily extrapolate from the animal studies described herein in order to arrive at appropriate doses for clinical administration. To achieve this conversion, one would account for the mass of the agents administered per unit mass of the experimental animal, and yet account for the differences in the body surface area between the experimental animal and the human patient. All such calculations are well known and routine to those of ordinary skill in the art. Accordingly, using the information provided herein, the inventors contemplate that useful daily doses of the agents that bind copper and form a tripartite agent-copper-protein complex, such as tetrathiomolybdate, for use in human administration would be between about 20 milligrams and about 200 milligrams per patient per day. Notwithstanding this stated range, it will be understood that, given the parameters and detailed guidance presented above, further variations in the active or optimal ranges would still be encompassed within the present invention.

The daily doses contemplated will therefore generally be between about 20 mg and about 180 milligrams; between about 130 mg and about 200 milligrams; between 25 and about 160 milligrams; between 50 and about 150 milligrams; between about 150 mg and about 180 milligrams; between about 30 and about 125 milligrams; between about 40 and about 100 milligrams; between about 35 and about 80 milligrams; between about 140 mg and about 190 milligrams; between about 20 and about 65 milligrams; between about 125 mg and about 195 milligrams; between about 30 and about 50 milligrams; between about 150 mg and about 200 milligrams; or in any particular range using any of the foregoing recited exemplary doses or any value intermediate between the particular stated ranges.

Although doses in and around about 60-120 mg are currently preferred in certain embodiments of the present invention, and doses in and around about 125-200 mg are currently preferred in other embodiments of the present invention, it will be understood that lower doses may be more appropriate in combination with other agents, or under conditions of maintenance, and that high doses can still be tolerated, particularly given the fact that the agents that bind copper and form a tripartite agent-copper-protein complex for use in the invention are not themselves cytotoxic and even if certain adverse side effects do occur, this should not necessarily result in toxicity that cannot be counteracted by normal homeostatic mechanisms, which is believed to lessen the chances of significant toxicity to healthy tissues.

In certain preferred embodiments of the present invention, daily loading dosages of between about 130 mg or about 150 mg or so to about 180 mg or about 200 mg or so are administered to patients for about 2 weeks, followed by daily maintenance dosages of between about 30 mg or about 40 mg or so and about 60 mg or about 70 mg or so, or any values intermediate between the particular stated ranges. Thus, in particular aspects of the invention, loading dosages of greater than about 125 mg, greater than about 130 mg, greater than about 140 mg, greater than about 150 mg, greater than about 155 mg, greater than about 160 mg, greater than about 170 mg, greater than about 175 mg, greater than about 180 mg, greater than about 190 mg, or greater than about 200 mg or so up to the maximum dosages described herein are contemplated by the inventors as exemplary daily loading dosages for about 1 week, about 2 weeks, about 3 weeks or about 4 weeks or so, followed by daily maintenance dosages of about 20 mg, about 25 mg, about 35 mg, about 40 mg, about 50 mg, about 55 mg, about 65 mg, about 75 mg, about 80 mg or about 90 mg or so.

The intention of the therapeutic regimens of the present invention is generally to produce the maximum anti-tumor effects whilst still keeping the dose below the levels associated with unacceptable toxicity. In addition to varying the dose itself, the administration regimen can also be adapted to optimize the treatment strategy. A currently preferred treatment strategy is to administer between about 20 milligrams and about 200 milligrams of the agents that bind copper and form a tripartite agent-copper-protein complex or combination thereof about 3, about 4, about 5 to about 6 or more times a day, approximately half of the time with meals, and approximately half of the time between meals. In administering the particular doses themselves, one would preferably provide a pharmaceutically acceptable composition to the patient systemically. Oral administration is generally preferred.

VI. Other Diseases Characterized by Aberrant Angiogenesis

In addition to the prevention or treatment of cancer and solid tumors, the thiomolybdate compositions disclosed herein can also be used in preventing or treating other diseases associated with aberrant vascularization, including, but not limited to, arthritis, diabetes, arteriosclerosis, arteriovenous malformations, corneal graft neovascularization, delayed wound healing, diabetic retinopathy, age related macular degeneration, granulations, burns, hemophilic joints, rheumatoid arthritis, hypertrophic scars, neovascular glaucoma, nonunion fractures, Osier-Weber Syndrome, psoriasis, pyogenic granuloma, retrolental fibroplasia, pterygium, scleroderma, trachoma, vascular adhesions, ocular neovascularization, parasitic diseases, hypertrophy following surgery, and inhibition of hair growth.

Macular degeneration is the common name for the age-related disease where macular retinal pigment epithelium cells function less well than normal. As a result, waste removal and nutrition of the cones suffers, causing central vision loss. Macular degeneration can be further classified into two varieties: a "dry type" and a "wet type". Dry type macular degeneration occurs when the outer segments of the light sensing cones, which are continuously being shed, are unable to be digested by the pigment epithelium layer of the macula. Consequently the pigment epithelium layer swells and eventually dies after accumulating too much undigested material from the cones. Yellowish deposits of this waste material gradually develop under the retina between the choroid and pigment epithelium. In this "dry type" macular degeneration, the vision loss is characterized by gradual blurring or partial obscuration of central vision as a result of parts of the macula having begun to die, creating areas where the cones are no longer functional. Clinically, the person suffering from this type of the disease may experience relatively mild central visual distortion with straight lines appearing bent or wavy.

In the second or "wet" type of this disorder, more severe and sudden vision loss may occur. This occurs when abnormal new blood vessels or "neovascular membranes" grow from the choroid through the damaged pigment epithelium and under the macula. These neovascular membranes are fragile and are prone to hemorrhage, which results in severe distortion of the macular tissue. As a result, the light sensing cells (cones) become separated from their source of nutrients and suffer further damage due to scarring as the hemorrhage occurs over time. With this type of disorder, dark or "missing" spots in the central vision may occur rapidly and with little warning due to these hemorrhagic changes. Fortunately, intervention with laser therapy early in this process may prevent additional vision loss.

Age-related macular degeneration (AMD) is the leading cause of visual loss among adults aged 65 years or older in Western countries. Although neovascular AMD accounts for only 10% of all cases, it is responsible for 80% to 90% of legal blindness due to this disease and is the most common cause of choroidal neovascularization (CNV) in this age population. The pathological changes leading to CNV involve the complex of tissues in the choriocapilaris, Bruch's membrane, and the retinal pigment epithelium (RPE) with secondary involvement of the neurosensory retina. Essentially anything that alters the retinal pigment epithelium and Bruch's membrane can cause CNV.

A variety of conditions other than AMD have been associated with CNV, including ocular histoplasmosis syndrome (POHS), pathologic myopia, angioid streaks, and idiopathic causes. Most histopathological studies have been performed in eyes with AMD. The histopathological feature common to many eyes that develop CNV is a break in Bruch's membrane. The capillary-like neovascularization originates from choroidal vessels and extends through these breaks. Age-related macular degeneration accounts for the largest group of patients with CNV. Most symptomatic CNV's are subfoveal and demonstrate an extremely poor natural history. Subfoveal neovascularization is defined as lesions lying under the geometric center of the foveal avascular zone (FAZ). Of untreated eyes followed for 2 years in a Macular Photocoagulation Study (MPS), only 5% had a final visual acuity better than 20/100, whereas 88% had a final visual acuity of 20/200 or worse.

Laser photocoagulation has been the mainstay of therapy for choroidal neovascularization. Through a series of well-executed randomized, prospective clinical trials, the MPS established the superiority of photocoagulation over observation for CNV in a variety of settings. Specifically, photocoagulation treatment of extrafoveal and juxtafoveal neovascular membranes in AMD and other disorders was found to be beneficial compared to the no treatment group. However, in order to treat the entire area of CNV, the ophthalmologist has to be able to identify the boundaries of the choroidal neovascular membrane. Therefore, treatment is indicated only when the boundaries of the CNV are well demarcated. Unfortunately, occult or ill-defined new vessels are the most common pattern at presentation for exudative macular lesions in AMD. In one study, visible or classic neovascular membranes involved only 23% of eyes referred for treatment. The MPS recently reported results of photocoagulation for subfoveal neovascular lesions in AMD showed benefit of laser treatment, but the difference between the treatment and observation groups was small and was seen only after two and five years. Also, as the laser energy destroys both the retina and subretinal membrane, there was a precipitous drop in visual acuity associated with treatment. These results underline both the poor natural history of the condition and the limitations of photocoagulation as a treatment modality.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Another disease in which angiogenesis is believed to be involved is rheumatoid arthritis. Rheumatoid arthritis is characterized by diffuse and nodular mononuclear cell infiltration and massive hyperplasia of the stromal connective tissues, comprised of fibroblast-like cells and new blood vessels. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

VII. Wilson's Disease

A. Background

Wilson's disease is an autosomal recessive disorder of copper metabolism. In this disorder, the excretion of copper into the bile appears to be defective, and there is reduced hepatic incorporation of copper into ceruloplasmin, leading to an accumulation of copper in plasma and most body tissues. Wilson's disease usually leads to hepatic and/or neurologic dysfunction.

The therapy of Wilson's disease can be divided into two broad categories (Brewer and Yuzbasiyan-Gurkan, 1992a). These are initial therapy in acutely ill patients, and maintenance therapy. Initial therapy is that period of time during which a newly presenting patient is still suffering from acute copper toxicity, generally the first few weeks to months of therapy. Maintenance therapy is essentially the rest of the patient's life, or that period of time after the copper levels have been brought down to a subtoxic threshold, and the patient is on therapy simply to prevent the recurrence of copper accumulation and copper toxicity.

For the maintenance therapy of Wilson's disease three drugs are currently available. These include the oldest available drug, penicillamine (Walshe, 1956), a drug called trien or trientine which was developed for patients who are intolerant of penicillamine (Walshe, 1982), and zinc acetate (Brewer and Yuzbasiyan-Gurkan, 1992a, b; Brewer et al., 1983; Hill et al., 1987; Hill et al., 1986; Brewer et al., 1987b, c, d; Yuzbasiyan-Gurkan et al., 1989; Brewer et al., 1989; Lee et al., 1989; Brewer et al., 1990; Brewer et al., 1991b; Brewer and Yuzbasiyan-Gurkan, 1989; Brewer et al., 1992a, b; Yuzbasiyan-Gurkan et al., 1992; Brewer et al., 1993a, b, c, d; Brewer, 1993; Hoogenraad et al., 1978; Hoogenraad et al., 1979; Hoogenraad et al., 1987). Zinc provides an effective maintenance therapy with a very low level of toxicity.

About ⅔ of patients who present with Wilson's disease present with symptoms referable to the brain (Brewer et al., 1992a; Scheinberg and Sternlieb, 1984; Danks, 1989). These can be neurologic symptoms or symptoms of psychiatric nature in the beginning, with neurologic symptoms later. Therapy for these patients is not nearly as straightforward as it is for maintenance phase patients. The inventors have found that approximately 50% of these patients who are treated with penicillamine become worse rather than better (Brewer et al., 1987a). Half of these patients who worsen, or about 25% of the original sample, never recover to their pre-penicillamine baseline. In other words, penicillamine has induced additional irreversible damage.

The mechanisms of this worsening are not known with certainty although it is likely that the mobilization of hepatic copper by the drug further elevates brain copper. The inventors have shown that this can occur in a rat model. Regardless of the mechanism, neurologically-presenting patients very often end up much worse off after being treated initially with penicillamine. In fact, even presymptomatic patients can develop neurologic disease after being initiated on penicillamine (Glass et al., 1990; Brewer et al., 1994a). It is not known whether trientine exhibits the phenomenon of neurological worsening when used as initial therapy, because it has not been used very much in this kind of situation. It would not be surprising if it exhibited this problem to some degree because of it's similar mechanism of action to that of penicillamine, but it might be much less, because its effects on copper seem to be somewhat gentler.

Zinc is not an ideal agent for the initial treatment for this type of patient. Zinc has a relatively slow onset of action, and produces only a modest negative copper balance. Thus, during the several months required for zinc to bring copper down to a subtoxic threshold, patients may be at risk for further copper toxicity and worsening of their disease.

B. Results of TM Therapy

The inventors have carried out an open label study of the use of TM for initial treatment of neurologically presenting Wilson's disease patients for the past several years. The inventors have developed both a spectrophotometric and bioassay for the activity of the drug, to evaluate stability, and assure potency of the drug being administered (Brewer et al., 1991a; Brewer et al., 1994b). The drug slowly loses potency when exposed to air. Oxygen molecules exchange with the sulfur molecules, rendering the drug inactive.

The results in the first patient studied can be used to illustrate several points. For the first seven days, the patient received TM only with meals (tid with meals). This produced the immediate negative copper balance one would expect from the first mechanism of action (blockade of copper absorption when given with meals). After the first seven days, TM was given between meals as well (tid with meals, and tid between meals). This led to the immediate rise in plasma copper expected from absorption of TM into the blood, and formation of a complex of copper, TM, and albumin. The copper complexed with TM and albumin is unavailable for cellular uptake, and this copper is therefore non-toxic (Gooneratne et al., 1981b). There is a 1:1 stoichiometric relationship between molybdenum and copper in this complex. Knowing the molybdenum level in the blood, and the ceruloplasmin level (ceruloplasmin also contains copper that is non-toxic), one can calculate how much of the plasma copper is not bound to one or the other. This so-called "free copper" (non-ceruloplasmin plasma copper) is the potentially toxic copper. When reduced to zero, the plasma copper-molybdenum "gap" is closed. This took 16 days in the first patient (9 days after adding the between meal doses). Since the brain (and the other organ) free copper is in equilibrium with the blood, bringing the blood free copper down to a low level begins the process of lowering the brain level of free (toxic) copper.

The inventors have now treated a total of 51 Wilson's disease patients with TM, all of whom presented with neurological or psychiatric disease, in an open label study. These patients were all diagnosed by standard criteria. These patients had a diagnostically elevated hepatic or urine copper, usually both. Some of them were treated briefly with other agents prior to this trial. Two patients had psychiatric but not neurological symptoms.

With three exceptions in the earliest part of the study, all patients received a dose of 20 mg tid with meals, or qid with three meals and a snack. Thus, the only difference between a patient receiving 120 mg and 140 mg total dose is that the former was receiving 20 mg tid, or 60 mg, with meals, and the latter was receiving 20 mg qid, or 80 mg with meals plus a snack. The rest of the total daily dose was divided up into three equal doses and given between meals.

The total daily dose was varied considerably among the patients, from a high of 410 mg to a low of 120 mg. In the end, the inventors could discern no dose-related correlation with copper variables, nor with functional variables measured either during the study or at the one and two year time point.

Zinc administration was also used in these patients. The starting time of zinc administration was varied widely and did not correlate with copper variables, outcome variables or toxicity. Early zinc therapy should theoretically help preserve liver function. In these patients, liver function returned to normal by year 1, but since these tests don't measure the extent of tissue preservation, it seems likely that zinc was somewhat beneficial.

Measuring trichloracetic acid (TCA) soluble copper of the plasma is somewhat useful in assessing the impact of TM therapy on copper metabolism in Wilson's disease. Generally, a high proportion of plasma copper in these patients is TCA soluble (it averaged 56% in patients—which is 27 µg/dl). All of the non-ceruloplasmin plasma copper is TCA soluble, and a somewhat variable portion of the ceruloplasmin copper is also TCA soluble. Because the ceruloplasmin levels are usually rather low in Wilson's disease, most of the plasma copper is TCA soluble. The copper in the TM/albumin/copper complex in the blood is TCA insoluble. Thus, as therapy proceeds, the fraction of the plasma copper which is TCA soluble becomes smaller. During the late stages of TM therapy, the TCA soluble fraction of plasma copper of the patients averaged 15 µg/dl, a significant reduction from the starting value of 27. The TCA solubility fraction cannot be used as an absolute endpoint, for example attempting to reduce it to zero, because a small and somewhat variable soluble fraction is usually present due to plasma ceruloplasmin. However, the significant mean reduction from 27 to 15 µg/dl illustrates the beneficial effect TM therapy has on the status of the potentially toxic plasma copper in these patients. Further evidence of the desirable impact of TM therapy on copper metabolism is shown by reduction of mean urine copper values during the latter part of TM therapy, compared to baseline values.

TM impacts quickly and favorably on copper metabolism, reducing the potentially toxic copper of the blood and theoretically, the rest of the body. The primary clinical objective is to gain control over copper toxicity while not allowing clinical worsening. In other words, the prime objective is to protect all neurological function that is present at the time therapy is started. This was evaluated weekly by quantitative neurological and speech exams. Methodology and the neurology rating scale system have been published (Young et al., 1986). During the weeks of TM administration, during which copper metabolism is being controlled, neurological function as evaluated by quantitative neurological exam, is protected. Only two patients (4% of the sample) showed a change of more than 5 units, the criterion for significant worsening.

During the following years, while the patients are on maintenance therapy, the brain damage previously induced by copper is at least partially repaired. This is exemplified by the partial recovery in neurological scores seen at yearly timepoints in follow-up. It is clear that with the initial TM approach, long term recovery is excellent, most patients showing substantial neurological recovery. These excellent results are to be contrasted with penicillamine therapy. As pointed out earlier, about 50% of patients initially deteriorate on penicillamine, and that half of these, or 25% of the original sample, never recover to their pre-penicillamine baseline.

The results during the initial 8 weeks of TM therapy on quantitative speech exams are performed as described (Brewer et al. 1996). During the weeks of TM administration, during which copper metabolism is being controlled, neurological function as measured by quantitative speech exams is being controlled. No patient shows significant (more than 2.0 units) reduction in scores. During the following years, while the patients are on maintenance therapy, the brain damage previously induced by copper is partially repaired. This is exemplified by the partial recovery in speech scores over years of follow-up. Long term recovery is excellent. No patient shows significantly (more than 2.0 units) less long term function than at the time of initiation of therapy, and most show marked improvement.

Two undesirable effects from TM therapy were observed in these patients. One is a reversible anemia/bone marrow depression, which was exhibited by seven patients. The fall in hemoglobin in all of these patients was significant, averaging 3.4 g %. Three of the patients showed a reduction in platelet count and four of the patients showed a reduction in white blood cell count that may have been significant. TM was stopped in all seven cases. Except for two of the patients, stoppage was late in the 56 day course of TM.

At the time of the anemia, these patients all had zero non-ceruloplasmin plasma copper and an extremely low TCA soluble copper. The latter averaged 2.7 in these patients, and the average value for this variable in the entire group of patients was 27 at the beginning and 15 at the height of therapy. The cause of the anemia/bone marrow depression was concluded to be bone marrow depletion of copper. Since copper is required for heme synthesis and other steps in cell proliferation, it could be expected that anemia and bone marrow effect would be the first signs of copper depletion. This result from copper depletion is a well-known phenomenon.

Thus, this undesirable response to TM is not a side effect but is, rather, due to overtreatment. It is perhaps surprising that it is possible to produce even localized bone marrow copper depletion within such a short period of time in Wilson's disease, a disease in which the body is overloaded with copper. This response to TM is unique. None of the other anti-copper drugs are able to produce this effect in early therapy. Thus, this speaks to the potency of TM and the rapidity with which it can control copper levels. Its also likely that the bone marrow is especially dependent on plasma copper, and that it is the first pool that it is reduced to very low levels. At a dose of 180 mg/day or over, overtreatment occurred in 6 of 37 patients. At a dose of 150 or lower, only 1 of 13 patients exhibited overtreatment, and that was very late (53 days in the 56 day program).

The second undesirable effect of TM therapy in these patients is an elevation of transaminase values in four of the patients. The serum AST and ALT values were elevated. TM therapy was discontinued in one patient because of these elevations. During these elevations, the urine copper increases, contrary to the general trend in other patients, where it is decreasing. These data support the concept that a hepatitis is occurring, with release of copper from damaged hepatocytes. It is not clear why this hepatitis is occurring. However, untreated Wilson's disease patients have a episodic hepatitis as part of their history. Since there is little in the way of observation of untreated patients after diagnosis, no good information exists on how often episodes of transaminase elevations occur as part of the natural history of the disease.

Alternatively, the TM in some cases may be mobilizing hepatic copper at a faster rate than it can be disposed of, in which case these patients would be classified as showing a side effect of treatment. Against this is the observation in copper-poisoned sheep, in which the acute hepatitis, liver necrosis, and hemolytic anemia are rapidly corrected with high doses of TM. All four of these patients were treated with 150 mg TM/day or higher. None of the patients treated with 150 mg or lower exhibited this response. No other negative effects of TM have been observed.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Effect of TM on Cellular Toxicity

Normal and neoplastic cells in culture derive their nutrients from transport and utilization of molecules from the media to the interior of the cell. This process is not dependent on blood vessel growth, and therefore TM should have no effect on cell growth rates and cell viability over a wide range of concentration, until a level of TM which is toxic to most cells is reached. One mechanism of toxicity is the depletion of free copper levels below those required for basic cell function. For concentrations of TM beyond this toxic level, both normal and neoplastic cells will be unable to survive, due to cellular toxicity of TM.

This was confirmed in a cytotoxicity assay of MML cells (prostate cancer) and breast cancer cells. After plating cells in equal numbers in media containing various concentrations of TM ranging from 0.001 μM to 1 mM, no toxicity was observed in the range of concentrations used in vivo. The fraction of viable cells decreased precipitously from 100% to 15% when the concentration of TM increased from 1 μg/ml to 10 μg/ml. TM is therefore not contemplated for use a direct cytotoxic agent, as it is clear that, at the very high doses required for a cytotoxic effect, both tumor and normal cell death would occur. The serum TM concentrations needed to achieve an effective decoppering level are 100-500-fold lower than the threshold lethal level for cells. When used at efficacious decoppering doses in mice and humans with Wilson's disease, TM has not resulted in any clinically apparent direct cell toxicity.

EXAMPLE 2

Use of TM in Murine Pre-Clinical Anti-Cancer Studies

The inventors reasoned that a greater degree of copper deficiency than previously achieved is necessary to significantly inhibit angiogenesis and arrest tumor growth. This means that, in addition to decreased tumor mass, prolonged survival or tumor regression would also be observed. The studies described below, which used anti-copper approaches for tumor growth inhibition in rodents, did not fully incorporate guidelines derived from human and animal trace element studies in general, and copper studies in particular (Dick and Bull, 1945; Miller and Engel, 1960; Macilese Ammerman et al., 1969; Mills et al., 1958; Cox et al., 1960; Dick et al., 1975; Mason, 1990; McQuaid and Mason, 1991; Mills et al., 1981a; Mills et al., 1981b; Bremner et al., 1982; Gooneratne et al., 1981a, b; Jacob et al., 1981).

In contrast, the present invention uses TM, the most potent anti-copper agent known. The inventors' extensive experience using zinc as a treatment in sickle cell anemia (where the inventors described the first human cases of zinc induced copper deficiency; Brewer et al., 1983), zinc as an anti-copper treatment in Wilson's disease (Brewer et al., 1989; Brewer, 1995a), and TM for the initial anti-copper treatment in Wilson's disease (Brewer et al., 1983; Brewer, 1992; Brewer et al., 1994b; Brewer et al., 1995b) was employed in the development of algorithms to achieve effective copper deficiency. As the developers of TM for clinical use, the inventors have acquired significant experience with TM in both animals and humans.

A. Injection of Tumor Cells into C567B1/C6 Mice

Under these guidelines, anti-angiogenesis therapeutic studies were conducted using TM in a mouse tumor model. This study involved subcutaneous or intramuscular injection of tumor cells into young adult C57B1/6J mice. Two tumors were used, a mouse sarcoma, MCA205, and a mouse melanoma, B16B16. The MCA 205 tumor cell suspension was injected subcutaneously into C57B16 mice. After the tumors were palpable, copper deficiency was induced by use of TM in half the animals, using Cp levels to monitor copper status. The other half were sham treated. Tumor growth was compared between the untreated control group and mice treated with sufficient TM to reduce Cp to about 10% of normal controls.

A significant effect on reducing the growth rate of tumors, and on reducing final tumor size and weight, was obtained with TM. Tumor growth was slowed by the treatment, although not halted, in the relatively brief period of observation (16 days). The tumors in TM-treated mice weighed significantly less than the tumors in control mice, normalized to the total weight of the animal. The results were similar in both tumor types. Thus TM reduced tumor growth and mass, presumably via its anti-angiogenesis mechanism, as there are no cytotoxic effect at the doses employed.

However, this experimental design can be improved further to evaluate the potential efficacy of TM as an anti-tumor agent for the following reasons: 1) In the mouse, tumors over 1 cm can become a life-threatening burden, and often ulcerate. However, in both mice and humans, it is tumors of this size and larger which are most dependent upon angiogenesis for sustained growth; and 2) The period between detecting the tumor at 2-3 mm and at 1.5 cm is relatively brief in the mouse, consisting of only a few days. As it takes time to deplete the tumor mass of copper (especially since most tumors sequester high levels of copper), the tumor may support significant angiogenesis from its own stores, prior to the achievement of near complete copper depletion.

B. HER2-neu Transgenic Mice

Therefore, an animal protocol was designed to test the effectiveness of TM in retarding or preventing clinically evident tumors in cancer prone female HER2-neu transgenic mice (Guy et al., 1992; Muller et al., 1988). These mice are normal at birth and in infancy, but because of the transgene, one hundred percent of these mice develop mammary tumors between 4-8 months of age (median 205 days) (Guy et al., 1992). A major additional reason for choosing this model is that the natural history of these murine mammary tumors is remarkably akin to the clinical behavior of untreated breast cancer in humans. The HER2-neu mouse tumors develop after a long latency (now known to be likely due to mutagenesis of the transgene and not to over expression) and they remain primarily local-regional until they achieve a large size (often >2.5 cm) before metastasizing mostly to lung. The time of onset of tumors and the quality and quantity of tumor vessels between the treatment and control groups were compared.

After breeding 3 founder transgenic females with 3 transgenic males, the female progeny was segregated into 2 groups: one group had 15 treatment and the other 22 control animals. The percentage of disease-free mice in the untreated control group was compared to a group of the same transgenic mice treated with 0.5-1.0 mg TM by gavage daily, starting at 100 days of age. Treatment with TM was initiated approximately 80-100 days before the tumors would have become clinically evident, so that the treated animals are rendered copper deficient throughout the key period of tumor development when angiogenesis may begin to be required. This prevents tumors from sequestering large amounts of copper from which they could sustain angiogenesis, even in the face of falling total body copper.

With a median follow-up of 260 days, none of the TM-treated mice developed clinically overt tumors, whereas 70% of the controls had shown tumors in the same follow-up period (FIG. 1). Fifty percent of control mice had developed clinically apparent tumors by age 218 days (p<0.02). Whereas the controls started exhibiting tumors beginning at age 153 days, the TM-treated animals showed no tumors until TM-therapy was discontinued and copper levels were allowed to drift upwards (p<0.0146).

Figure 2:
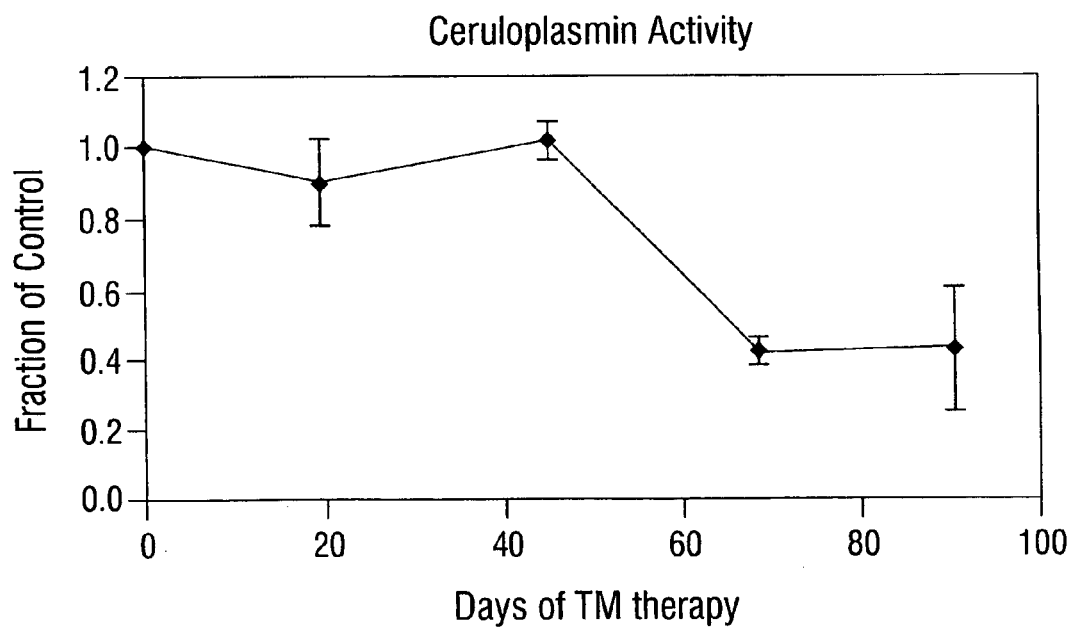
FIG. 2. Ceruloplasmin activity as a function of time in TM-treated mice. A spectrophotometric assay of activity was used for the serum of treatment and control mice at regular intervals during treatment. Fraction of control ceruloplasmin is shown on the vertical axis, days of TM therapy is shown on the horizontal axis.

Monitoring of blood copper levels in the treatment group by use of a surrogate indicator, ceruloplasmin (Cp), revealed that Cp had decreased to below 40% of baseline (FIG. 2). In this strain of mice, there was no anemia observed when the copper decreased to this level. A separate group of 4 treatment animals was given higher doses of TM between 1.0-1.5 mg over 2-4 weeks. The animals who received 1.25-1.5 mg died after 1-3 weeks of therapy. Autopsies revealed that one animal died of aspiration pneumonia (ascribed to gavage accident) whereas 2 animals died of renal tubular necrosis and pulmonary hemorrhages, with clear evidence of vascular injury to these tissues on necropsy. These studies suggest that 1.0 mg/day is the maximum tolerated dose (MTD) for TM in adult mice (average weight 32 grams), when prolonged treatment is planned.

In order to test whether mammary tumors in the control mice could be decreased in size with TM, 3 of the control animals were treated after the tumors were well established (>1.5 cm largest dimension). In 2/3 cases, the tumors were shrunk significantly by 25% and 50%.

Next, the possibility that prolonged TM therapy had somehow damaged the breast tissue so tumors could not possibly arise in the treatment animals due to lack of a target was determined. After 80% of the control animals and none of the treatment animals had developed tumors, the control animals were released from treatment. Clinically overt mammary tumors began to develop in this cross-over group of mice (which had been previously disease-free), within 18 days, suggesting that indeed the tumor initiation event in the target tissue had taken place but expansion of the tumor to a clinically detectable mass was not possible in the copper deficient state.

Microscopic analyses of the mammary glands of the TM-treated mice revealed a number (1-8) of small "micro-tumors" approximately 3-10 cell-layers thick which failed to vascularize. However, upon release from TM therapy, these micro tumors grew very rapidly into palpable masses that were briskly vascularized. Although not all the cellular and molecular details have yet been elucidated, it is clear that in this important carcinogenesis model, copper deficiency inhibited the angiogenic switch, or a step closely downstream from it, as none of the micro-tumors of the treated mice were vascularized.

In summary, decreasing copper availability decreases and eventually arrests solid tumor growth, including growth of metastases. The decrease in copper availability needed to decrease tumor growth in humans without Wilson's disease was ascertained as described herein below. The success of TM as an anti-tumor agent is based at least in part on the relationship between the degree of copper deficiency required to obtain efficacy, and the toxicity of that degree of copper deficiency. As tumor angiogenesis is abrogated when mild copper deficiency ensues, TM is a remarkably effective agent for several different oncologic applications. Other settings contemplated for TM therapy include, but are not limited to, maintenance therapy following chemotherapy or bone marrow transplantation, in patients who are elderly or otherwise ineligible to receive chemotherapy, or as a cytostatic agent in high-risk individuals (inflammatory cancer, multiple positive nodes).

C. Nude Mice with Transplanted Tumors

In this study, the ability of tetrathiomolybdate (TM) to abrogate or retard the growth of tumors in the mammary pads of nude mice after orthotropic injection of human breast cancer cells was studied. The highly angiogenic inflammatory breast cancer cell line called SUM149 was selected for this study. Given its high propensity to form palpable tumors within 2 weeks of injection into the mammary of 80-100% of the nude mice injected, this cell line posed a stringent test of the ability of TM to impair tumor progression.

Three groups of 5 nude mice each were set up in separate cages. Groups 2 and 3 received TM in the drinking water to average an intake of 1.2 mg/day/mouse, starting at day −7. Groups 1, 2, and 3 were injected on day 0 with $10^6$ SUM149 breast cancer cells in the second thoracic mammary fat pad. On day 34, as no palpable tumors were noticeable in any of the mice in the treatment groups, TM was skipped on groups 2 and 3, and then TM was restarted on group 2 at a dose of 0.6 mg/day/mouse, while TM was resumed at full dose (1.2 mg/mouse/day) in group 3.

Figure 3:
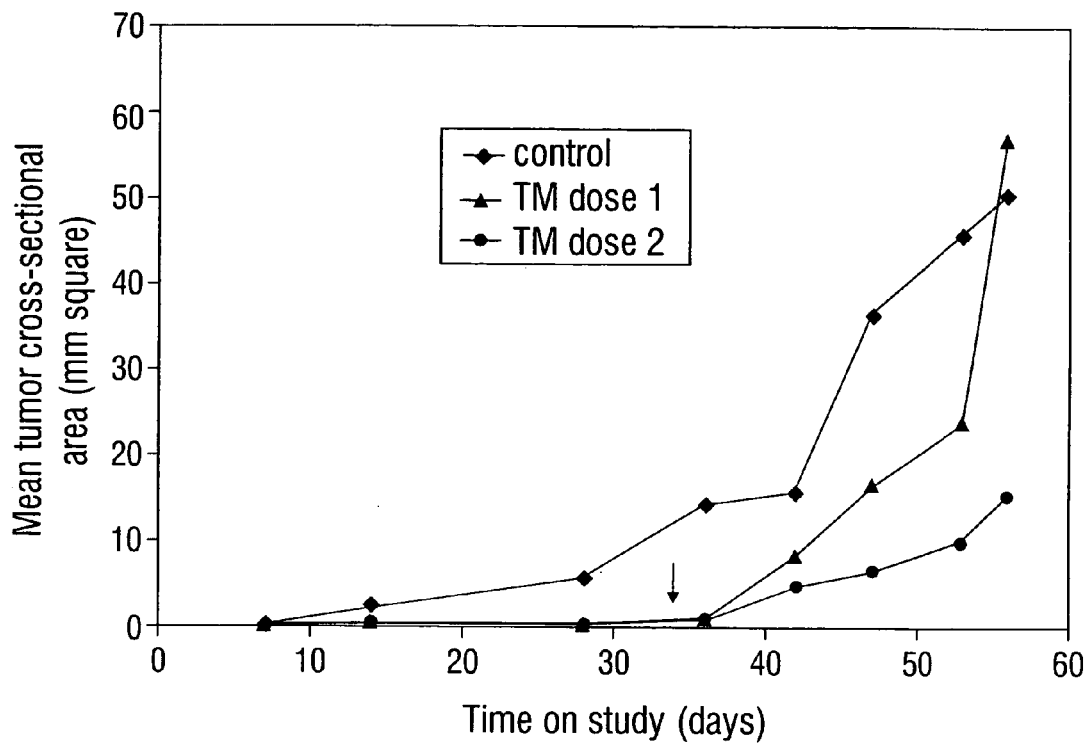
FIG. 3. Tumor size over time in nude mice injected with SUM149 breast cancer cell line cells. Three groups of five mice were injected with $10^6$ SUM149 breast cancer cells, and two of the groups were given 1.2 mg/day/mouse of TM via drinking water, starting at day −7. After 34 days, the TM was skipped in these two groups of mice, and then restarted at half of the previous dose (0.6 mg/day/mouse; Δ) or the full dose (1.2 mg/day/mouse; ○). Control mice (◇) received no TM. The mean tumor cross-sectional area ($mm^2$) is shown on the vertical axis, and time (days) is shown on the horizontal axis.

The developing tumors were measured approximately twice weekly, and the average of the product of the bi-dimensional perpendicular diameters for each group versus time is plotted in FIG. 3. The tumors in the control group grew relatively rapidly and all animals developed tumors. In contrast, for the treatment groups, no tumors were palpable until TM was skipped on day 34. Thereafter, the tumors grew more rapidly in the group that received ½ dose of TM, which is known to only decrease the copper levels by 50%. In contrast, only very small tumors have grown in the group treated with TM at fill dose, which is defined as 1.2 mg/day/mouse. This dose decreases copper to approximately 10-20% of baseline levels. It is this degree of copper deficiency, well tolerated in both mice and humans, which appears to be required to inhibit tumor angiogenesis.

This study supports the idea that TM probably inhibits angiogenesis at least in 2 ways: one is by inhibition of the "angiogenic switch", and the other is by inhibition of bulk tumor angiogenesis. Skipping TM on day 34 enabled the angiogenic switch to activate and begin to bring a vessel to the tumor cluster which had been injected in copper deficient nude mice. This activation of the switch enables some tumor growth, although it is clear that the group treated with TM has much slower tumor growth, and appears to be reaching a plateau. This study also validates oral administration of TM in the drinking water of the nude mice.

EXAMPLE 3

Phase I/II Clinical Trial of TM as Anti-Cancer Therapy

A. Introduction

Patients with metastatic solid tumors often have very limited treatment options due to the cumulative toxicity of cytoreductive chemotherapy and drug resistance. Following the pre-clinical work detailed above, which showed efficacy for the anti-copper approach in mouse tumor models, a Phase I clinical trial was conducted in 18 patients with metastatic cancer who were enrolled at 3 dose levels of oral tetrathiomolybdate (TM; 90, 105, and 120 mg/day) administered in 6 divided doses with and in-between meals. Serum ceruloplasmin (Cp) was used as a surrogate marker for total-body copper. As anemia is the first clinical sign of copper deficiency, the goal of the study was to reduce Cp to 20% of baseline value, without reducing hematocrit by more than 80% of baseline. Cp is a reliable and sensitive measure of copper status, and TM was non-toxic when Cp was reduced to 15-20% of baseline. The level III dose of TM of 120 mg/day was effective in reaching the target Cp, without added toxicity. TM-induced mild copper deficiency achieved stable disease in 5 out of 6 patients who were copper deficient at the target range for at least 90 days.

1. Toxicity

The pharmacological effects of TM are completely specific to copper. As it has no detectable effects on other minerals, its toxicity is then directly related to copper deficiency. Other than copper deficiency, at the doses employed, there is no toxicity described in animals. In humans, there are two reports of reversible anemia in Wilson's disease patients taking TM for maintenance therapy at doses of 30-40 mg 6 times per day. In treating 45 patients with Wilson's disease for eight weeks with TM as initial therapy for Wilson's disease, five cases of reversible anemia (11.1%) were observed. The anemia is due to decreased heme synthesis as a result of copper depletion in the bone marrow. The patients whose blood showed the most severe reduction in Cu levels exhibit this anemia.

As mentioned above, the copper status of an animal or human undergoing TM therapy cannot be followed by serum copper alone, because the complex of TM, copper, and albumin, is cleared more slowly from the blood than it accumulates, until a high copper steady state is reached. This complexed copper is however not available for cellular uptake, and is gradually cleared from the body via the urine and the bile, without participating in any cellular copper-dependent processes, such as angiogenesis. The inventors have developed guidelines for monitoring the copper balance in humans during TM therapy, according to the recognized three stages of copper deficiency (Brewer, 1992; Brewer et al., 1991a), as follows.

First Stage—Chemical Copper Deficiency

During this stage, the serum ceruloplasmin (Cp) activity is decreased up to approximately 5-10% of baseline. Cp, a copper containing protein, is synthesized in the liver and Cp synthesis is decreased during copper depletion. This stage of copper deficiency, although measurable in the laboratory, has no clinical signs or symptoms. The Cp must be below a few percent of normal before early clinical copper deficiency ensues.

Second Stage—Mild Clinical Copper Deficiency

After the Cp is held at 0-5% for a period of 5-10 days, the first clinical signs of copper deficiency may appear. These are mild neutropenia and hypochromic microcytic red cell changes. Both the white blood count and hematocrit fall to approximately 75-85% of baseline. Copper is required for heme synthesis, so the morphological changes seen in the peripheral smear are similar to those characteristic of iron deficiency. The anisocytosis and poikilocytosis exacerbate as copper deficiency becomes more severe. The onset of this mild anemia and neutropenia is gradual and often entirely asymptomatic.

Third Stage—Moderate to Severe Clinical Copper Deficiency

Typically when Hct<70% of baseline, more severe clinical signs and symptoms resulting from inadequate hematopoesis ensue. These are loss of appetite, weight loss, diarrhea, impaired melanogenesis with subsequent loss of hair color, rarely cardiac arrhythmias.

The inventors reasoned that mild chemical copper deficiency, (a condition which is extremely well tolerated by humans for seemingly long periods of time) has efficacy as a strategy to inhibit solid tumor angiogenesis. Modulation and careful monitoring of the degree of copper deficiency to establish surrogate end-points of efficacy of TM is therefore an important element of this approach.

The inventors have very good evidence-based knowledge about the various stages of relative copper deficiency, the dividing line between chemical and clinical copper deficiency, and appropriate protocols on what to measure to assess copper status. Since the patients are closely monitored, the Phase I study has so far proven to be quite safe. The major therapeutic issue to be discerned is whether the tumor angiogenic requirements for copper are significantly higher than essential cellular housekeeping needs for copper.

2. Pharmacodynamics

TM is administered orally with and without meals, and is well absorbed under the latter condition. TM forms a tripartite complex with copper and protein, thereby binding copper in food when administered with meals, preventing copper absorption, or in the bloodstream (TM-Cu-albumin) after absorption, preventing cellular copper uptake. In patients with normal copper metabolism, a stoichiometric 1:1 relationship between non-ceruloplasmin plasma copper (potentially available for angiogenesis) and plasma molybdenum is expected, with 6 daily doses of 10-20 mg each. The dose level of TM which will result in a steady state of mild copper deficiency varies within the range of 40-90 mg daily for most individuals. The complex of TM-Cu-protein is slowly excreted predominantly in bile, with a small amount excreted also in the urine. Twenty-four hour urine measurements of Mo and Cu will help determine the rate of elimination of the tripartite complex.

B. Methods

1. Patients

Eighteen adults with metastatic solid tumors, exhibiting measurable disease, life expectancy of 3 or more months, and at least 60% Karnofsky performance status (Table 2), were enrolled. Patients with effusions or bone marrow involvement as the only manifestations of disease, and those who had severe intercurrent illness requiring intensive management or were transfusion dependent, were excluded. Patients had to have recovered from previous toxicities, and had the following requirements for laboratory parameters: WBC≧3,000/mm$^3$, ANC≧1,200/mm$^3$, Hct≧27%, Hgb≧8.0 gm/dl, platelet count≧80,000/mm$^3$, bilirubin<2.0 mg/dl, AST/ALT<4 times the upper limit of institutional norm, serum creatinine<1.8 mg/dl or calculated creatinine clearance>55 ml/min, calcium≧11.0, albumin≧2.5 gm/dl, PT<13 sec., and PTT<35 sec. Other requirements were demonstrable progression of disease in the previous 3 months, after standard treatments such as surgery, chemotherapy, radiotherapy, and/or immunotherapy, or progressive disease after declining conventional treatment modalities.

TABLE 2

Karnofsky And Criteria ECOG Performance

| KARNOFSKY | | ECOG | |
|---|---|---|---|
| ACTIVITY | SCORE % | GRADE | ACTIVITY |
| Normal, no complaints | 100 | 0 | Fully active, able to carry on all predisease activities without restrictions |
| Normal, only minor signs/symptoms | 90 | | |
| Normal activity, but requires effort | 80 | 1 | No physically strenuous activity, but ambulatory and able to carry out light or sedentary work (e g., office work, light house work) |
| Unable to do active work, but able to care for self | 70 | | |
| Able to care for most needs, requires occasional help | 60 | 2 | Ambulatory/capable of all self-care, unable to perform any work activities. Up and about more than 50% of waking hours |
| Requires frequent medical help and considerable assistance | 50 | | |
| Disabled, needs special care and assistance | 40 | 3 | Capable of only limited self-care, confined to bed or chair more than 50% of waking hours |
| Severely disabled, needs hospitalization, death not imminent | 30 | | |
| Very sick, hospitalized, active support needed | 20 | 4 | Completely disabled, totally confined to bed or chair. Cannot carry on any self-care. |
| Moribund | 10 | | |
| Dead | 0 | 5 | Dead |

2. Treatment Schema: Doses and Escalation

Three dose regimens were evaluated. All dose levels consisted of TM 20 mg given 3 times daily with meals plus an escalating (levels I, II, and III) in-between meal dosing, given 3 times daily, for a total of 6 doses per day. Loading dose levels I, II, and III provided TM at 10 mg, 15 mg, and 20 mg, 3 times daily between meals, respectively, in addition to the 3 doses of 20 mg each, given with meals, at all dose levels.

Baseline Cp was taken as the nearest Cp measurement to day 1 of treatment, including day 1, since the blood was drawn pre-TM, for all patients. The target Cp reduction was defined as 20% of baseline Cp. Due to Cp assay variability of approximately 2%, a change of Cp to 22% of baseline was considered as achieving the desired reduction of copper. In addition, if the absolute Cp was less than 5 mg/dl, then the patient was considered as having reached the target Cp. No patient reached the target due to an absolute Cp of less than 5 mg/dl, without also being at least 78% reduced from baseline. After reaching the target copper deficient state, TM doses were individually tailored to maintain Cp within a target window of 70-90% reduction from baseline.

Six patients were to be enrolled at each dose level. After 4 patients were enrolled at level I, if one patient experienced dose-limiting toxicity (DLT) (defined as Hct<80% of baseline), 2 more patients were enrolled at level I. If no DLT was observed, patients were enrolled at the next dose level. Treatment was allowed to continue beyond induction of target copper deficiency, if the patients experienced a partial or complete clinical response or achieved clinical stable disease by the following definitions. Complete response is defined as the disappearance of all clinical and laboratory signs and symptoms of active disease. Partial response is defined as a 50% or greater reduction in the size of measurable lesions defined by the sum of the products of the longest perpendicular diameters of the lesions, with no new lesions or lesions increasing in size. Minor response is defined as a 25-49% reduction in the sum of the products of the longest perpendicular diameters of one or more measurable lesions, no increase in size of any lesions and no new lesions; stable disease is any change in tumor measurements not represented by the criteria for response or progressive disease, which is defined as an increase of 25% or more in the sum of the products of the longest perpendicular diameters of any measurable indicator lesions, compared to the smallest previous measurement or appearance of a new lesion. Because copper deficiency is not a cytotoxic treatment modality, the patients who provide information about the efficacy of TM for long-term therapy, in this population of patients with advanced cancer, are primarily those who remained within the target Cp window of (20±10)% of baseline for over 90 days, without disease progression

3. Monitoring of Copper Status

A method was required to monitor copper status easily and reliably, so that TM dose could be adjusted appropriately during this trial. With TM administration, serum copper is not a useful measure of total-body copper, because the TM-copper-albumin complex is not rapidly cleared, and the total serum copper (including the fraction bound to the TM-protein complex) actually increases during TM therapy (Brewer et al., 1991a; 1994b; 1996). The serum ceruloplasmin level obtained weekly was used as a surrogate measure of total-body copper status. The serum Cp level is controlled by Cp synthesis by the liver, which, in turn, is determined by copper availability to the liver (Linder et al., 1979). Thus, as total-body copper is reduced, the serum Cp level is proportionately reduced. The serum Cp level is in the range of 20-35 mg/dl and 30-65 mg/dl for normal controls and cancer patients, respectively. The objective as this trial was to reduce Cp to or below 20% of baseline, and to maintain this level, within a window spanned by (20±10) % of the baseline Cp, with typical Cp values in the range of 7-12 mg/dl. Since there appears to be no untoward clinical effects from this degree of copper reduction, this level of copper deficiency has been termed "chemical copper deficiency". The first indication of true clinical copper deficiency is a reduction in blood cell counts, primarily anemia, as copper is required for heme synthesis as well as cellular proliferation (Brewer et al., 1996). Thus, the copper deficiency objective of this trial was to reduce the Cp to 20% of baseline or below, without decreasing the patient's hematocrit or WBC to below 80% of the baseline value at entry.

4. Toxicity, Follow-Up, and Disease Evaluation

Complete blood counts, liver and renal function tests, urinalyses, and Cp level (by the oxidase method) were performed weekly for 16 weeks, then bi-weekly. Physical examinations and evaluations of toxicity were carried out every 2 weeks for 8 weeks, then every 4 weeks for the duration of therapy. Toxicity was evaluated using the National Cancer Institute Common Toxicity Criteria (Table 3). As TM is not a cytotoxic drug at the doses employed, and it has already been given to humans without any other toxicities than the ones described in detail above, the majority of the toxicities listed in Table 3, should they arise, are not expected to be due to TM. Nevertheless, therapy will be discontinued and the patient removed from the study if grade 3 or higher toxicities of any type are observed, whatever the probable etiology. For grade 2 toxicities, an attempt will be made to establish their etiology. If routine support care measures do not alleviate the conditions, the drug will be discontinued and the patients removed from the study.

Extent of disease was evaluated at entry, at the point of achievement of copper deficiency, defined as Cp at or below 20% of baseline, and every 10-12 weeks thereafter. Computer-assisted tomography or magnetic resonance imaging were used as appropriate for conventional measurement of disease at all known sites and for evaluation of any potential new sites of disease. Angiogenesis-sensitive ultrasound with 3-dimensional Doppler analyses was employed in select cases, as adjunct to conventional imaging, to evaluate the blood flow to the tumors at different time points.

TABLE 3

Toxicity Criteria

| | Toxicity Grade | | | | |
|---|---|---|---|---|---|
| | 0 | 1 | 2 | 3 | 4 |
| Blood/Bone Marrow | | | | | |
| WBC | ≧4.0K | 3.0-3.9K | 2.0-2.9K | 1.0-1.9K | <1K |
| Platelets | WNL | 75.0 K-WNL | 50-74.9K | 25.0-49.9K | <25K |
| Hemoglobin | WNL | 10.0 g-WNL | 8.0-10.0 g | 6.5-7.9 g | <6.5 g |
| Neutrophils | ≧2.0K | 1.5-1.9K | 1.0-1.4K | 0.5-0.9K | <0.5K |
| Lymphocytes | ≧2.0K | 1.5-1.9K | 1.0-1.4K | 0.5-0.9K | <0.5K |
| Hemorrhage, Clinical | None | Mild, No Transfusions | Gross, 1-2 U PRBC | Gross, 3-4 U PRBC | Massive, >4 U PRBC |
| Infection | None | Mild | Moderate | Severe | Life-Threatening |
| Gastrointestinal | | | | | |
| Nausea | None | Able to Eat | Intake Decreased | No Significant Intake | |
| Vomiting | None | 1 × /24 h | 2-5 × /24 h | 6-10 × 24/h | >10 × /24 h |
| Diarrhea | None | Increase of 2-3 × /24 h | Increase of 4-6 × /24 h | Increase of 7-9 × /24 h | Increase of ≧10 × /24 h |
| Stomatitis | None | Painless Ulcers | Painful Ulcers, Can Eat | Painful Ulcers, Cannot Eat | Requires IV Nutrition |
| Hepatic | | | | | |
| Bilirubin | WNL | | <1.5 × WNL | 1.5-3.0 × WNL | >3 × WNL |
| SGOT/SGPT | WNL | ≦2.5 × WNL | 2.6-5.0 × WNL | 5.1-20 × WNL | >20 × WNL |
| Alk Phos | WNL | ≦2.5 × WNL | 2.6-5.0 × WNL | 5.1-20 × WNL | >20 × WNL |
| Liver/Clinical | No Change | | | Precoma | Hepatic Coma |
| Kidney/Bladder | | | | | |
| Creatinine | WNL | <1.5 × WNL | 1.5-3.0 × WNL | 3.1-6.0 × WNL | >6.0 × WNL |
| Proteinuria | No Change | 1 + <0.3 gm % | 2-3 + 0.3-1.0 gm % | 4 + >1.0 gm % | Nephrotic Syndrome |
| Hematuria | Negative | Microscopic | Gross | With Clots | Transfusion |
| Alopecia | No Loss | Mild | Total | | |
| Cardiovascular | | | | | |
| Dysrhythmia | None | Asymptomatic No Therapy | Persistent No Therapy | Requires Therapy | Hypotension, V-tach/V-fib |
| Cardiac | None | Decline of EF by <20% | Decline of EF by >20% | Mild CHF, Rx Responsive | Refractory CHF |
| Ischemia | None | Nonspecific ST-T Wave Δ | Asymptomatic Ischemic Δ | Angina, No Infarction | Acute MI |
| Pericardial | None | Asymptomatic Effusion | Pericarditis, rub, EKG Δ | Symptomatic Effusion | Tamponade |
| Hypertension | None or No Δ | Transient, >20 mm Hg | Persistent, >20 mm, No Rx | Requires Therapy | Hypertensive Crisis |
| Hypotension | None | Transient, No Therapy | Fluid Replacement | Hospitalized <48 h | Hospitalized >48 h |
| Pulmonary | No Change | Asymptomatic Abnormal PFT | Dyspnea on Exertion | Dyspnea, no exertion | Dyspnea at Rest |
| Neurologic | | | | | |
| Neuro-sensory | No Change | Mild Paresthesia | Moderate Sensory Loss | Severe Loss, Symptomatic | |
| Neuro-motor | No Change | Subjective Weakness | Mild Objective Weakness | Impairment of Function | Paralysis |
| Cortical | None | Mild Somnolence, Agitation | Moderate Somnolence, Agitation | Severe, with Confusion or Hallucination | Coma or Seizures |
| Cerebellar | None | Slight Change Coordination | Speach Slur Tremor, Nystagmus | Ataxia | Cerebellar Necrosis |
| Mood | No Change | Mild Anxiety or Depression | Moderate | Severe | Suicidal |
| Headache | None | Mild | Transient Mod-Severe | Unrelenting, Severe | |
| Constipation | None | Mild | Moderate | Severe | Ileus >96 h |
| Hearing | No Change | Asymptomatic Audiometry Δ | Tinnitus | Correctable Loss | Dear, not Correctable |
| Vision | No Change | | | Symptomatic Subtotal Loss | Blindness |
| Skin | No Change | Macular/Papular Rash, Asymptomatic | Rash with Pruritus | Generalized Eruption | Exfoliative or Ulcerative Rash |
| Allergy | None | Transient Rash, Temp <38° C. | Urticaria, Mild Bronchospasm, T >38° C. | Serum Sickness, Bronchospasm | Anaphylaxis |
| Fever | None | 37.1-38° C. | 38.1-40° C. | >40°, <24 h | <40°, >24 h |
| Local | None | Pain | Inflammation Phlebitis | Ulceration | Plastic Surgery Rx |

TABLE 3-continued

Toxicity Criteria

Toxicity Grade

| | 0 | 1 | 2 | 3 | 4 |
|---|---|---|---|---|---|
| Weight Change | <5% | 5-9.9% | 10-19.9% | ≧20% | |
| Metabolic | | | | | |
| Hyperglycemia | <116 | 116-160 | 161-250 | 251-500 | >500, Ketoacidosis |
| Hypoglycemia | >64 | 55-64 | 40-54 | 30-39 | <30 |
| Amylase | WNL | <1.5 × WNL | 1.5-2.0 × WNL | 2.1-5.0 × WNL | >5.1 × WNL |
| Hypercalcemia | <10.6 | 10.6-11.5 | 11.6-12.5 | 12.6-13.5 | ≧13.5 |
| Hypocalcemia | >8.4 | 8.4-7.8 | 7.7-7.0 | 6.9-6.1 | ≦6.0 |
| HypoMagnesemia | >1.4 | 1.4-1.2 | 1.1-0.9 | 0.8-0.6 | ≦5.0 |
| Coagulation | | | | | |
| Fibrinogen | WNL | .75-1 × WNL | .5-74 × WNL | .25-.49 × WNL | ≦>24 × WNL |
| PT | WNL | 1-1.25 × WNL | 1.26-1.5 × WNL | 1.51-2.0 × WNL | >2.0 × WNL |
| PTT | WNL | 1-1.25 × WNL | 1.26-1.5 × WNL | 1.51-2.0 × WNL | >2.0 × WNL |

5. TM Preparation and Storage

TM was purchased in bulk lots suitable for human administration (Aldrich Chemical Company, Milwaukee, Wis.). As TM is slowly degraded when exposed to air, with oxygen replacing the sulfur in the molecule, rendering it inactive (Brewer et al., 1991a; 1994b; 1996), it was stored in 100-gram lots under argon. At the time a prescription was written, the appropriate dose of TM was placed in gelatin capsules. Previously, it was shown by the inventors that TM dispensed in such capsules retained at least 90% of its potency for eight weeks (Brewer et al., 1991a). Thus, TM was dispensed to each patient in eight-week installments throughout the trial.

6. Measurement of Blood Flow

Blood flow was measured by ultrasound in select patients with accessible lesions, at the time they became copper deficient, and at variable intervals of 8-16 weeks thereafter. 3D scanning was performed on a GE Logiq 700 ultrasound system, with the 739L, 7.5 MHz linear array scanhead. The scanning and vascularity quantification techniques were as previously described (Carson et al., 1998; LeCarpentier et al., 1999).

B. Results

1. Patient Characteristics

Eighteen eligible patients, 10 males and 8 females, with 11 different types of metastatic cancer who had progressed through or (in one case) declined other treatment options were enrolled in the trial, in the order in which they were referred. Six, 5, and 7 patients were enrolled at the 90, 105, and 120 mg/day drug levels, respectively, following the protocol dose escalation schema. One patient originally assigned to the 105 mg level was removed early to pursue cytotoxic chemotherapy, due to rapid progression of disease. This same patient was later retreated at the 120 mg level for a longer duration, and thus is counted only at the 120 mg drug level for the analyses. The average age was 59; the average baseline Cp was 47.8 mg/dl, which is elevated with respect to normal reflecting the patients' disease status. Table 4 summarizes the patients' characteristics for each dose level.

TABLE 4

Patient Characteristics

| | Assigned TM Dose (mg) | | | |
|---|---|---|---|---|
| | 90 | 105 | 120 | Total |
| Characteristic | | | | |
| No. of Patients | 6 | 5 | 7 | 18 |
| Sex (M/F) | 3/3 | 1/4 | 6/1 | 10/8 |
| Age [Mean (SD)] | 64 (12) | 60 (12) | 53 (17) | 59 (14) |
| Primary Tumor: | | | | |
| Breast | 2 | 2 | 0 | 4 |
| Colon | 0 | 1 | 0 | 1 |
| Lung | 1 | 0 | 0 | 1 |
| Melanoma | 0 | 0 | 1 | 1 |
| Pancreas | 0 | 1 | 0 | 1 |
| Prostate | 2 | 0 | 0 | 2 |
| Angiosarcoma | 0 | 0 | 2 | 2 |
| Chondrosarcoma | 0 | 1 | 0 | 1 |
| Nasopharyngeal | 0 | 0 | 1 | 1 |
| Hemangioendothelioma | 0 | 0 | 1 | 1 |
| Renal | 1 | 0 | 2 | 3 |
| Baseline: | | | | |
| Baseline Cp mean | 52.6 | 49.3 | 42.7 | 47.8 |
| Baseline Cp range | 36.6-74.1 | 38.1-65.0 | 31.9-52.7 | 31.9-74.1 |
| Baseline Hct mean | 31.9 | 37.2 | 41.9 | 37.3 |
| Baseline Hct range | 26.6-35.6 | 33.8-42.5 | 35.4-45.7 | 26.6-45.7 |

2. Toxicity

There were no cardiac, pulmonary, GI, renal, hepatic, hematologic, infectious, skin, mucosal, or neurologic toxicities observed for Cp levels at or above 20% of baseline. Mild (greater than 80% of baseline Hct) reversible anemia was observed in 4 patients for Cp levels between 10-20% of baseline. Two of these patients had been treated with cytotoxic chemotherapy and two patients had evidence of extensive bone marrow involvement with their disease at the time of entry into the trial. Although in the latter two of these cases, the anemia was most likely due to causes other than treatment, TM was discontinued temporarily until Hct was restored to acceptable levels with transfusion of 2 units of packed RBCs. In one patient, it is very likely that the copper deficiency caused by TM produced the anemia. Stopping the drug allowed the hematocrit to recover within 5-7 days without the need for transfusion; at the patient's request, TM was restarted at a lower dose, without further complications of anemia. Several patients experienced transient, occasional sulphur-smelling burping, within 30 minutes of TM ingestion. No additional toxicities of any type were observed with long-term maintenance of mild clinical copper deficiency over 8-15 months. Of note, no evidence of GI or other mucosal bleeding or impaired healing of minor trauma were observed with long-term therapy. One pre-menopausal patient with extensive metastatic renal cancer experienced normal menstrual periods during TM therapy, including 2.5 months of observation while copper deficient with Cp<20% of baseline.

3. Ceruloplasmin as a Surrogate Measure of Copper Status

Figure 4A:
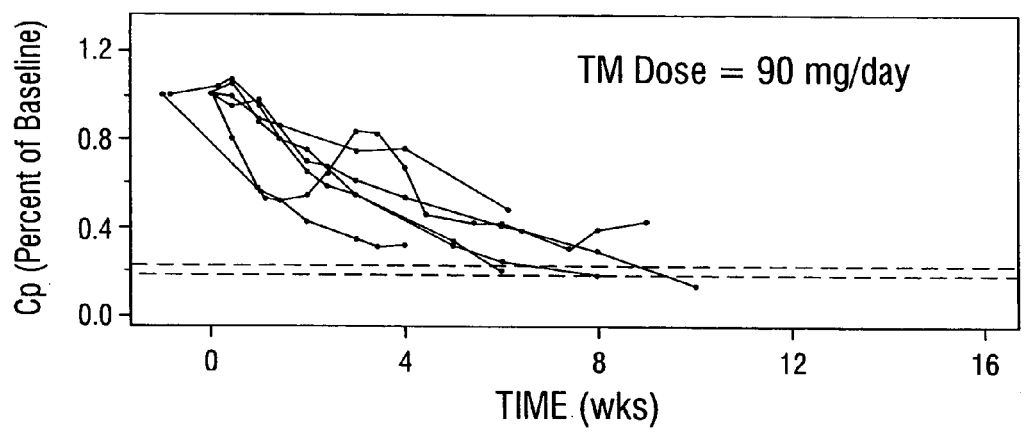
FIG. 4A, FIG. 4B and FIG. 4C. Ceruloplasmin as a surrogate marker of total-body copper status. Rates of decrease of the ratio of Cp at time t to baseline Cp, as a function of days on TM therapy, are depicted for dose levels I (FIG. 4A), II (FIG. 4B), and III (FIG. 4C). The average time to 50% reduction of Cp is 30 days.
Figure 4B:
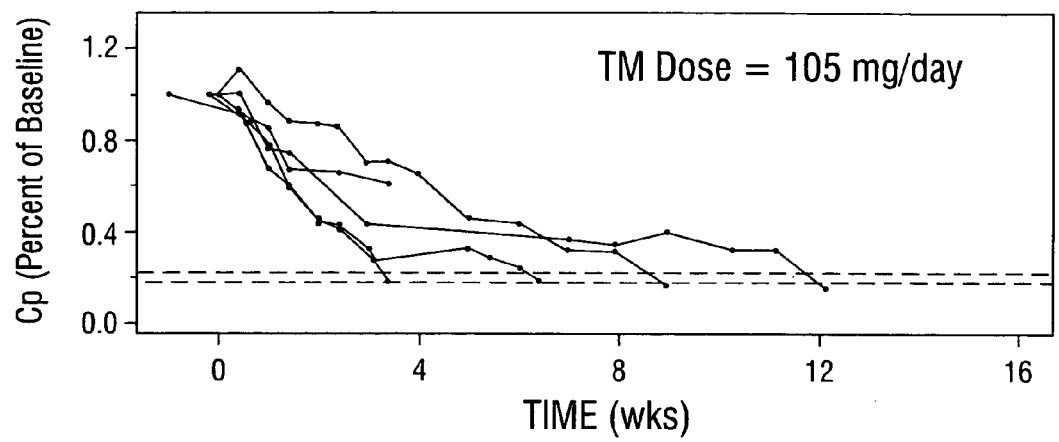
Figure 4C:
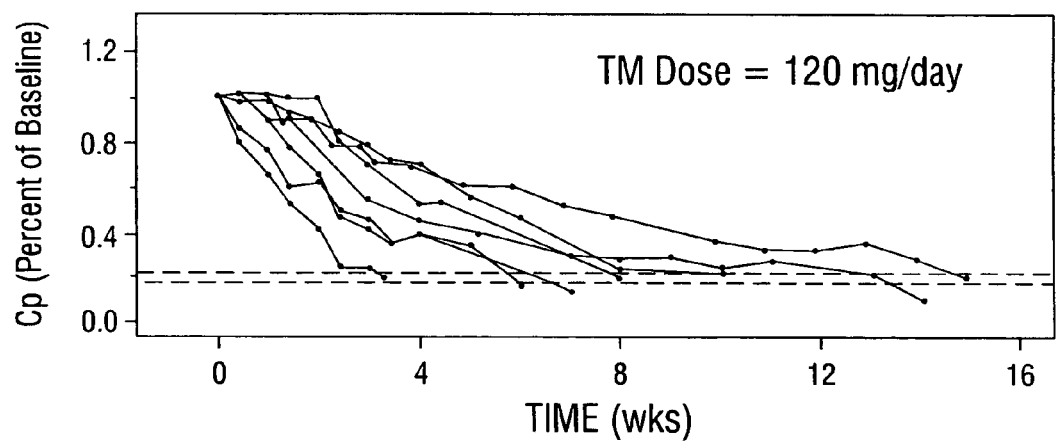

FIG. 4A, FIG. 4B and FIG. 4C shows the response of Cp as a function of time on TM therapy, expressed as the ratio of Cp at time t to the baseline Cp level for each patient enrolled at the 90 mg/day (FIG. 4A), 105 mg/day (FIG. 4B), and 120 mg/day (FIG. 4C) dose levels. Increasing the in-between meals dose from 10 mg 3× daily to 15 mg or 20 mg 3× daily had no significant effect on the rate of decrease of the Cp level, reaching a level of 50% baseline at a mean of 30 days (median=28 days). The response of Cp to TM therapy as a function of time exhibited only minor fluctuations; when TM was discontinued, a rapid rise in Cp, within 48 hours, was observed.

Four patients were removed from study due to progression of disease prior to achieving target Cp of 20% of baseline, while the remaining 14 patients achieved the target Cp level. Since all 14 patients who achieved the target Cp level wished to remain on study, they were allowed to do so, according to the protocol, as long as they did not exhibit disease progression or toxicity. The TM doses were adjusted in these patients to maintain the Cp between 10-20% of baseline. These patients provide the preliminary evidence of efficacy and of long-term tolerance of this approach.

4. Dose Adjustments to Maintain Target Cp

In order to maintain a Cp target of 20% of baseline and to prevent absolute Cp values less than 5 mg/dl, TM doses were adjusted. Due to a routine 7-day turn-around for the Cp test, these dose changes were made approximately 7-10 days after the blood for the Cp measurement was taken. After achieving the target Cp, the in-between meals dose was typically decreased by 20 mg. Further decreases of 15-30 mg were necessary during long-term therapy. A patient with metastatic chondrosarcoma secondary to radiation treatment for breast cancer on long-term therapy has stable disease after 12 months of copper deficiency, with stable quality of life. One biopsy-proven metastatic nodule on the third digit is easily measurable and has been stable. Interestingly, this patient has required only a minor adjustment to the TM dose from the initial loading dose level to maintain the target Cp throughout this relatively long period.

Figure 5A:
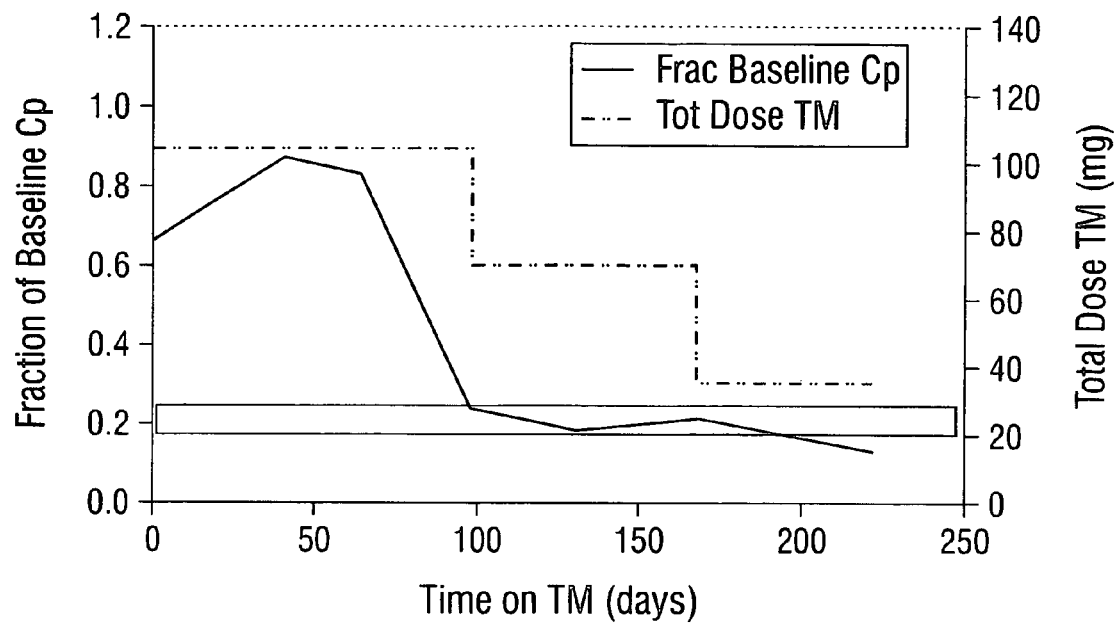
FIG. 5A and FIG. 5B. Management of long-term therapy with TM to maintain a Cp target of 20% of baseline in two patients.
Figure 5B:
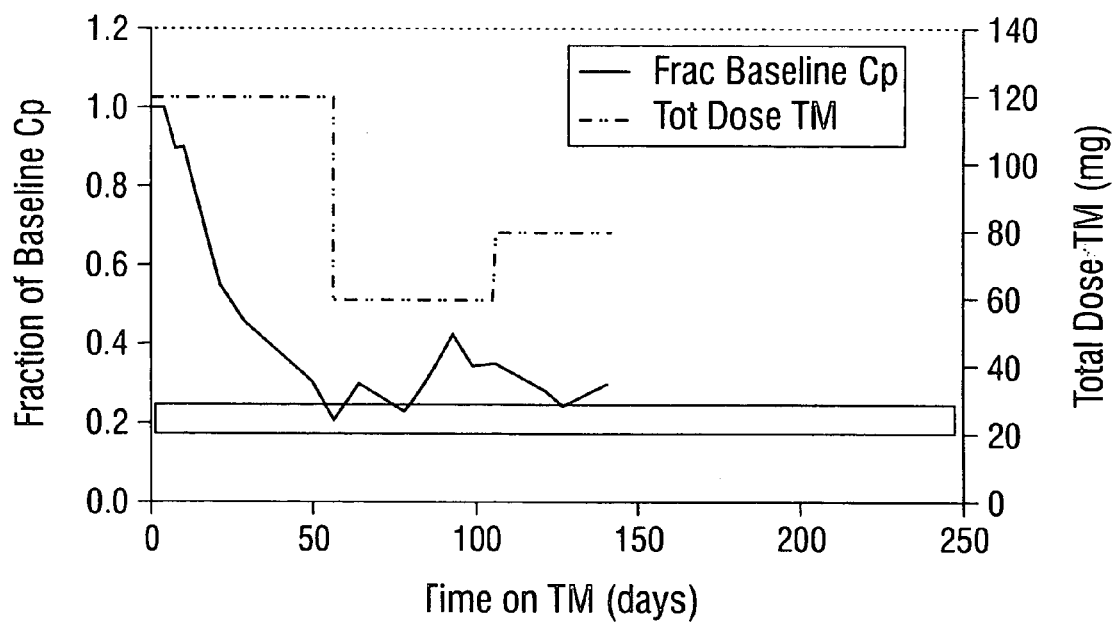

FIG. 5A and FIG. 5B illustrate the Cp response to dose adjustments required for two more representative patients over approximately 100 days of therapy. The patient in FIG. 5A has so far required only decreases in dose 60 days apart. Most patients have required both increase and decrease in dose, during long-term therapy. For example, as shown in FIG. 5B, the TM dose was increased after day 100 to respond to an increase in Cp outside the target range. Overall, there was considerable individual variability in the dose adjustments required. Other sites of suspected disease in the chest also remain stable. In conclusion, the Cp response to TM therapy evaluated weekly is not brittle or subject to wide fluctuations.

5. Measurement of Response of Metastatic Cancer to TM a. Clinical Evaluation

Although the patients received different initial loading doses of TM, the Cp maintenance window of (20±10)% of baseline was used in all groups, regardless of the loading dose. Patients who maintained this degree of copper deficiency through tailored adjustments of the TM dose for over 90 days, are likely to reflect the anti-angiogenic activity of TM against their tumors. The period of 90 days is selected for 2 main reasons. First, TM is not cytotoxic to either cancer or endothelial cells and mainly impairs endothelial cell function and pro-angiogenic factor production. This mechanism of action is expected to have a very slow effect on the size of tumor masses. Second, as tumors sequester copper, the microenvironment of the tumor is expected to take a longer time to be rendered copper deficient. Table 5 summarizes the clinical course of the 18 patients.

TABLE 5

Summary of Type and Length of Response to TM Therapy

| Type of Response | No. of Patients | Duration of Cu Deficiency, days (Average) |
|---|---|---|
| Did Not Achieve Target Cp | 4 | |
| Achieved Target Cp | 14 | |
| Target Cp <90 days | 8/14 | |
| Disease progression | 7 | |
| Stable disease with partial regression of lung lesions | 1 | 49+ |
| Target Cp >90 days | 6/14 | |
| Stable disease with partial regression of lung lesions | 1/6 | 120+ |
| Stable disease | 4/6 | 159*, 329+, 351+, 413+ (313+) |
| Disease progression at one site, stable elsewhere | 1/6 | 120+ |

*Patient discontinued therapy;
+On therapy

Fourteen patients achieved the target copper deficiency prior to disease progression or other disease complications. Of these, 8 patients either progressed within 30 days of achieving copper deficiency or have had stable disease for fewer than 90 days; it is unlikely that most of these tumors experienced an anti-angiogenic environment long enough to evaluate clinical response to this type of therapy. In all patients who were removed from protocol due to disease progression or choice, and in one patient due to the need for abdominal surgery to relieve a small bowel obstruction, much more rapid rates of progression of disease were noted clinically, after discontinuation of TM therapy.

The remaining 6 patients experienced stable disease (5/6) or progression of disease at one site, with stable disease elsewhere (1/6). Two patients who have stable disease by standard criteria also experienced complete disappearance of some lung lesions and decrease in size of other lung lesions during observation periods at target Cp of 120 and 49 days. The 5 patients on long-term (over 90 days) maintenance therapy with stable disease have been copper deficient between 120 and 413 days at the time of this analysis.

b. Radiologic Evaluation

Serial evaluations of tumor masses by conventional imaging with CAT scan or MRI revealed that the radiographic appearance of the certain masses changed significantly over time. In particular, areas of presumed central necrosis (corresponding to lower attenuation of the X-ray signal) were observed in a variety of tumor types, most notably renal cell cancer, angiosarcoma, and breast cancer. Seeking to evaluate the blood flow to the tumors as a function of time during copper deficiency on long-term TM therapy, lesions accessible to ultrasound were imaged with color flow 3-dimensional ultrasound at the onset of copper deficiency, and at intervals of 2-4 months thereafter.

Conventional CAT scan images and blood-flow sensitive 3D-ultrasound were compared in a rib metastasis from a renal cell carcinoma upon reaching target copper deficiency and 8 weeks later. A CAT scan showed this lesion to be of a stable size over time, although a more distinct region of (probable) central necrosis is observed 8 weeks after reaching target copper deficiency. In comparison, a decrease in blood flow to this mass by 4.4-fold in this period of approximately 8 weeks was detected by the 3D-ultrasound. In addition to the mass studied by these two techniques, this patient had extensive disease in the chest, pelvis, and femurs.

c. TM in Combination with Other Treatment Modalities

During the long-term maintenance of copper deficiency, additional treatment modalities were added to TM, as deemed appropriate for the optimal management of the patients. A patient with previously untreated metastatic breast cancer is doing well with a good to excellent quality of life after 12 months of treatment. This patient had metastases in the paratracheal, posterior cervical, and retroperitoneal lymph node chains, but had declined all cytotoxic therapy. The patient had stable disease for over 6 months on TM treatment, when, due to slight increase (less than 25% of baseline) in the bidimensional size of the paratracheal and retroperitoneal nodes, was begun on concurrent trastuzumab therapy, after this drug became commercially available. This patient showed a rapid response to trastuzumab at all sites of disease: after 1 cycle, there was a clinical complete response in the neck, and after 3 cycles of trastuzumab, there was radiologic confirmation of complete response at all previous sites of disease. The patient remains on TM, but the trastuzumab was discontinued after 6 doses. The patient continues to maintain status as a complete responder on TM alone for 3 months after discontinuation of trastuzumab therapy. Because the complete response was achieved after addition of trastuzumab therapy, this patient is classified as having only stable disease on TM in Table 5.

Two patients with extensive angiosarcoma of the face and scalp achieved stable disease on TM. In one patient with severe chronic bleeding from an ocular lesion which threatened the orbit, interferon-alpha 2 (IFN-α) was added to TM to attempt to enhance tumor response. Given the suggestion that, based on studies of progressing hemangiomas, the use of low-dose interferon may be efficacious for the treatment of hemangioma (Takahashi et al., 1994), IFN-α was administered to both of these patients at a dose of 500,000 units subcutaneously twice a day. Radiotherapy was also given to these 2 patients while on TM, to attempt to control actively bleeding (but not progressing) lesions. Both patients had disease stabilization for over 60 days, with one of them remaining with stable disease for over 5 months, prior to discontinuation of therapy due to patient choice. No exacerbation of toxicity was observed by addition of any of these treatment modalities to TM.

This is the first human trial of induction and maintenance of copper deficiency with tetrathiomolybdate as an anti-angiogenic therapy for cancer. In a group of patients with advanced cancer, it was demonstrated that TM is remarkably non-toxic when Cp is lowered to 10-20% of baseline levels for up to 17 months of treatment. The only drug-related toxicity observed was mild anemia in one patient, which was easily reversible with adjustment in the TM dose to bring the Cp level to the desired target. In spite of the diverse roles that copper plays in diverse essential biological processes including heme synthesis, superoxide dismutase and cytochrome function, no lasting significant adverse effects were observed upon reduction of Cp to approximately 20% of baseline. This level of copper reduction constitutes the lower limit of chemical copper deficiency and the beginning of mild clinical copper deficiency, the first manifestation of which is mild anemia.

The use of serum Cp level obtained by the oxidase method, an inexpensive and widely available test, was validated as a sensitive and reliable surrogate marker of total-body copper status during TM therapy. Using the six times per day dose regimen, and initial TM doses ranging from 90 to 120 mg per day, the serum Cp was reliably lowered to 50% of baseline in 17 out of 18 patients treated and to 20% of baseline in 14 out of 18 patients. Reduction to 50% of baseline was achieved on the average in 30 days, with further reduction to Cp levels of 5-10 mg/dl taking 20-30 days. Although this rate of decrease in Cp is reasonable for the initial treatment of early malignant lesions or in the adjuvant setting, in widely metastatic advanced cancer, this rate of decrease will be accelerated to prevent some disease progression during induction of copper deficiency in a significant number of patients. Since loading dose variations of 90 to 120 mg per day do not appear to affect the rate of Cp reduction, and given the typical daily intake of copper with food, higher doses in-between meals will be required to accelerate the rate of induction of copper deficiency.

As the Cp response to TM-induced copper deficiency is monotonic and exhibits little inter-subject variability, there is essentially no risk of sudden changes or unpredictable fluctuations that might make dose management difficult. Following Cp levels once every one to two weeks is adequate to monitor copper status. As a corollary, overtreatment is easily detectable and correctable.

As a result of this study it is apparent that, with the present TM dose regimens, there is considerable lag between initiation of TM therapy and reduction of copper levels in tumors to a likely anti-angiogenic level. Further retarding the ability to reach anti-angiogenic levels of copper deficiency is the likelihood that most tumors sequester copper (Arnold and Sasse, 1961; Apelgot et al., 1986; Gullino et al., 1990; Fuchs and Sacerdote de Lustig, 1989). Thus, additional time may be required to deplete the tumor micro-environment to an effectively low level of copper, defined as a level low enough to inhibit angiogenesis. Patients with very rapidly progressive large tumors may therefore require additional treatment modalities, as described herein, in addition to anti-angiogenesis therapy.

Furthermore, initially effective anti-angiogenesis may cause brisk tumor necrosis, resulting in the release of additional copper from the dying cells. In the case of one patient, a transient rise in Cp was observed at approximately the same time as the ultrasound suggested that the large tumor mass might be undergoing central necrosis due to a significant decrease in blood flow. Thus, a period of 60-90 days of Cp at the target level of 20% of baseline is a reasonable starting point for evaluation of response to anti-copper therapy. In the two patients who exhibited partial regression of lung lesions, tumor control may have begun earlier. It is also interesting to note that, in both of these patients, the lung parenchymal metastases were the sites of tumor regression. It is possible that mild clinical copper deficiency impairs superoxide dismutase function (Culotta et al., 1997) so that under conditions of high oxidant stress, such as those present in the lung, the metastatic foci are more susceptible to oxidative damage.

In spite of individual differences, the use of 3D-ultrasound to determine the total blood flow to a given mass demonstrates that maintenance of mild copper reduction to 20% of baseline induced for at least 8 weeks appears sufficient to alter tumor blood flow. Due to the relative insensitivity of computer-assisted tomography to the blood flow or metabolic status of the lesions, parallel imaging modalities, as demonstrated here for 3-D ultrasound, are preferred to assess functional response in addition to tumor size.

These studies show that that the size of solid tumors of a variety of types may be stabilized or decreased by TM, given sufficient time in a state of mild clinical copper deficiency represented by a decrease in Cp to or below 20% of baseline, as defined by this study. Among the patients who were maintained at the target Cp level for more than 90 days, a significant proportion of cases (5/6) were stabilized, with no detriment to their quality of life. In this population of patients with advanced disease, 39% of those treated were able to be maintained at the target Cp for this duration.

The pattern and speed of progression observed in these patients have also provided useful information. One patient achieved stable disease at all sites but one, and has chosen to remain on TM therapy due to disease stabilization at the more life-threatening sites of disease (bowel and paratracheal lymph nodes). Interestingly, the site of progression in this patient with melanoma is a large adrenal metastasis, which is at present being irradiated. This and other observations in this trial suggest that, whereas copper deficiency may be generally inhibitory of angiogenesis, heterogeneity of tumor type and the specific location of metastases may modulate the response to this therapeutic modality. Since it appears that lesions progress at a much faster rate upon copper repletion than while on TM therapy, adjunct modalities, either systemically or local-regionally, may be used to address the specific sites of progression, while allowing the patients to remain in a copper deficient state.

These studies also show that combination therapies of TM with radiotherapy, trastuzumab, and interferon-alpha, occur without apparent exacerbation of toxicity of the added modality. Taken as a whole, the safety and preliminary efficacy data derived from this trial supports the use of TM alone, or in combination, for the treatment of early metastatic disease, minimal disease, and in adjuvant high-risk clinical settings, including chemoprevention.

EXAMPLE 4

Phase II/III Clinical Trial of TM as Anti-Cancer Therapy

A. Introduction

Four considerations enter into designing the drug dose and schedule for this trial. The first is that the dose regimens previously used, although effective in reducing copper, take too long to get to the Cp endpoint in order to properly evaluate efficacy. As it is known that tumors sequester copper (Apelgot et al., 1986; Arnold and Sasse, 1961), anti-angiogenic effects will not likely be detected until systemic copper deficiency has been maintained perhaps for at least a few weeks to months. Thus, it is important to get to the endpoint of systemic copper deficiency (0-20% Cp level) as quickly as possible to maximize the potential for efficacy. Thus, the present trial utilizes a "loading" dose, to be used for two weeks, to achieve Cp criteria, followed by a lower maintenance dose, to remain at the target Cp of 0-20% baseline. This design utilizes the knowledge gained in the Phase I trial and will determine the efficacy of TM to provide stable disease or tumor decrease.

Second, the trial will evaluate whether an efficacious response depends on how rigorously Cp levels are controlled. Thus, in the first group of patients, Cp levels are maintained between 10 and 20%, and in the second group Cp levels are maintained between 0 and 10%.

Third, this trial will determine whether maintenance of a low copper status is more easily maintained with zinc therapy. The inventors have developed zinc as an FDA approved therapy for Wilson's disease. It acts by inducing intestinal metallothionein and blocking the absorption of copper. Thus in 6 patients, the low copper status will be maintained by using 25 mg of zinc tid, with dose adjustments as necessary to maintain Cp criteria.

B. Phase II Study

1. Loading Dose

The inventors have found that a dosing schedule of 20 mg tid with meals, and a single dose of 60 mg between meals reduces the Cp level to <20% more rapidly than 20 mg tid with meals and 20 mg tid between meals. Therefore, this dosing schedule will be studied in a Phase II study. Three other loading doses of TM will also be studied: Level 1: 20 mg tid between meals and 20 mg tid with meals until Cp<20% (10 patients); Level 2: 25 mg tid between meals and 25 mg tid with meals until Cp<20% (10 patients); and Level 3: 30 mg tid between meals and 30 mg tid with meals until Cp<20% (10 patients).

The objective of the loading dose study is to arrive at the desired Cp level (<20% of baseline) within 2-3 weeks. The trial will begin with Level 1. If Level 1 achieves the desired Cp level, all 30 patients will be loaded at dose Level 1. If Level 1 does not achieve the desired Cp level, the trial will move to loading dose Level 2, and on to dose Level 3 if necessary. Each of these doses are safe for weeks to a few months.

2. Maintenance Dose of TM

Two levels of maintenance dose will be studied: Level 1: TM doses adjusted as necessary to maintain Cp at 10-20% of baseline (12 patients); and Level 2: TM doses adjusted as necessary to maintain Cp at 0-10% of baseline (12 patients).

The objective of comparing two maintenance dose levels is to get a general picture of whether more stringent copper control tends to enhance efficacy. In general, the tumor types will be randomized between the two levels.

3. Maintenance Dose of Zinc

Two patients from each loading dose group, for a total of six patients, will be treated with zinc therapy for maintenance control. The trial will begin with 25 mg of zinc 3 times per day (away from food) and adjust the dose to maintain Cp below 20% of baseline.

The objective of the zinc study is to see if it is easier to control copper status during maintenance with zinc than with TM, and to get a general picture of whether efficacy with zinc is generally comparable to efficacy with TM.

4. Patient Selection Criteria

The patient selection criteria will include: a) metastatic adenocarcinoma, squamous carcinoma, or sarcoma of any organ of origin; b) measurable disease by chest X-ray, CAT Scan, or plain bone films; c) progressive disease documented at least once within 3 months of entry; d) ability to provide informed consent; e) performance status ECOG 0-1; and f) life expectancy $\geqq 6$ months.

Exclusion criteria include hematocrit less than 29, LFT's more than four times normal, or severe concurrent medical disease requiring intensive management.

5. Parameters

The parameters that will be followed in the patients are: 1) CBC platelets, weekly; 2) electrolytes, BUN, creatinine, LFT's weekly; 3) blood for serum copper, molybdenum, ceruloplasmin weekly; 4) urinalysis weekly; 5) clinical status every 2 weeks; 6) tumor measurement every 4 weeks; and 7) research angiogenesis—sensitive ultrasound every 8 weeks.

6. Toxicity Endpoints

As before, the drug will be stopped when either hematocrit or WBC drops below 80% of baseline. The drug will also be stopped if there is evidence of possible systemic toxicity, such as abnormal liver or renal function tests, or any other grade 3 or higher toxicity by NCI criteria.

7. Length of Study

If there is not evidence of disease stabilization or reduction in a patient by 6 months, the study in that patient will be terminated. Otherwise, therapy will continue as long as the disease is controlled within 25% of the initial size at all sites, there is not significant toxicity, and the patient desires to continue.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,399,586, issued Mar. 21, 1995.
U.S. Pat. No. 5,464,833, issued Nov. 7, 1995.
U.S. Pat. No. 5,504,074, issued Apr. 2, 1996.
U.S. Pat. No. 5,539,094, issued Jul. 23, 1996.
U.S. Pat. No. 5,565,491, issued Oct. 15, 1996.
U.S. Pat. No. 5,571,523, issued Nov. 5, 1996.
U.S. Pat. No. 5,576,330, issued Nov. 19, 1996.
U.S. Pat. No. 5,583,034, issued Dec. 10, 1996.
U.S. Pat. No. 5,587,459, issued Dec. 24, 1996.
U.S. Pat. No. 5,591,717, issued Jan. 7, 1997.
U.S. Pat. No. 5,593,664, issued Jan. 14, 1997.
U.S. Pat. No. 5,599,813, issued Feb. 4, 1997.
U.S. Pat. No. 5,605,826, issued Feb. 25, 1997.
U.S. Pat. No. 5,618,925, issued Apr. 8, 1997.
U.S. Pat. No. 5,622,829, issued Apr. 22, 1997.
U.S. Pat. No. 5,639,725, issued Jun. 17, 1997.
U.S. Pat. No. 5,650,491, issued Jul. 22, 1997.
U.S. Pat. No. 5,654,155, issued Aug. 5, 1997.
U.S. Pat. No. 5,672,603, issued Sep. 30, 1997.
U.S. Pat. No. 5,677,178, issued Oct. 14, 1997.
U.S. Pat. No. 5,693,473, issued Dec. 2, 1997.
U.S. Pat. No. 5,693,627, issued Dec. 2, 1997.
U.S. Pat. No. 5,709,999, issued Jan. 20, 1998.
U.S. Pat. No. 5,710,001, issued Jan. 20, 1998.
U.S. Pat. No. 5,716,981, issued Feb. 10, 1998.
U.S. Pat. No. 5,733,876, issued Mar. 31, 1998.
U.S. Pat. No. 5,747,282, issued May 5, 1998.
U.S. Pat. No. 5,747,469, issued May 5, 1998.
U.S. Pat. No. 5,750,400, issued May 12, 1998.
U.S. Pat. No. 5,750,653, issued May 12, 1998.
U.S. Pat. No. 5,753,441, issued May 19, 1998.
U.S. Pat. No. 5,756,294, issued May 26, 1998.
U.S. Pat. No. 5,756,455, issued May 26, 1998.
U.S. Pat. No. 5,763,223, issued Jun. 9, 1998.
U.S. Pat. No. 5,776,704, issued Jul. 7, 1998.
U.S. Pat. No. 5,776,743, issued Jul. 7, 1998.

Abrams and Oldham, *Monoclonal Antibody Therapy of Human Cancer*, Foon and Morgan (eds.), Martinus Nijhoff Publishing, Boston, pp. 103-120, 1985.

Allen and Solomons, "Normal Intestinal Mechanisms in the Absorption of Copper," In: Absorption and Malabsorption of Mineral Nutrients, Solomons and Rosenberg (Eds), Alan R. Liss, Inc., New York, 12:206, 1984.

Apelgot, Coppey, Fromentin, Guille, Poupon, Roussel, "Altered Distribution of Copper ($^{64}$Cu) in Tumor-Bearing Mice and Rats," *Anticancer Research* 6:159-164, 1986.

Arnold and Sasse, "Quantitative and Histochemical Analysis of Cu, Zn, and Fe in Spontaneous and Induced Primary Tumors of Rats," *Cancer Res.* 21:761-766, 1961.

Badet, Soncin, Guitton, Lamare, Cartwright and Barritault, "Specific binding of angiogenin to calf pulmonary artery endothelial cells," *Proc. Natl. Acad. Sci. USA* 86:8427-8431, 1989.

Baxter, et al., "Transport of fluid and macromolecules in tumors. III. Role of binding and metabolism," *Microvasc. Res.* 41:5-23, 1991.

Benjamin, Golijanin, Itin, Pode and Keshet, "Selective ablation of immature blood vessels in established human tumors follows vascular endothelial growth factor withdrawal," *J. Clin. Invest.* 103:159-165, 1999.

Bickel, Neale, Hall, "A Clinical and Biochemical Study of Hepatolenticular Degeneration (Wilson's Disease)," *Quart. J. Med.* 50:527, 1957.

Borgstom, Bourdon, Hillan, Sriramarao and Ferrara, "Neutralizing anti-vascular endothelial growth factor antibody completely inhibits angiogenesis and growth of human prostate carcinoma micro tumors in vivo," *Prostate* 35:1-10, 1998.

Borgstom, Hillan, Sriramarao and Ferrara, "Complete inhibition of angiogenesis and growth of microtumors by anti-vascular endothelial growth factor neutralizing antibody: Novel concepts of angiostatic therapy for intravital videomicroscopy," *Cancer Res.* 56:4032-4039, 1996.

Brem, Tsanaclis, Zagzag, "Anticopper Treatment Inhibits Pseudopodial Protrusion and the Invasive Spread of 9L Gliosarcoma Cells in the Rat Brain," *Neurosurgery* 26:391-396, 1990a.

Brem, Zagzag, Tsanaclis, Gately, Elkouby, Brien, "Inhibition of angiogenesis and tumor growth in the brain. Suppression of endothelial cell turnover by penicillamine and the depletion of copper, an angiogenic colactor," *Am. J. Pathol.,* 137(5):1121-1142, 1990b.

Bremner and Young, "Effects of Dietary Molybdenum and Sulphur on the Distribution of Copper in Plasma and Kidneys of Sheep," *Br. J. Nutr.* 39:325, 1978.

Bremner, Mills, Young, "Copper metabolism in rats given di- or trithiomolybdates," *J. Inorg. Biochem.,* 16: 109, 1982.

Brewer and Yuzbasiyan-Gurkan, "Wilson Disease," *Medicine,* 71(3):139-164, 1992a.

Brewer and Yuzbasiyan-Gurkan, "Wilson's Disease," In: Textbook of Clinical Neuropharmocology and Therapeutics, 2nd Edition, Klawans, Goetz, Tanner (Eds.), Raven Press, New York, pp. 191-205, 1992b.

Brewer and Yuzbasiyan-Gurkan, "Wilson's disease: an update, with emphasis on new approaches to treatment," *Dig. Dis.,* 7(4):178-193, 1989.

Brewer, "Interactions of zinc and molybdenum with copper in therapy of Wilson's disease," *Nutr.*, 11(1 Suppl):114-116, 1995b.

Brewer, "Practical recommendations and new therapies for Wilson's disease," *Drugs,* 50(2):240-249, 1995a.

Brewer, "Thiomolybdates in the treatment of Wilson's disease," Letter to the Editor. *Arch. Neurol.*, 49: 132-133, 1992.

Brewer, "Zinc in the Treatment of Wilson's Disease," *Nutrition and the MD.* 19(12): 1993.

Brewer, Dick, Johnson, Wang, Yuzbasiyan-Gurkan, Kluin, Fink, Aisen, "Treatment of Wilson's disease with ammonium tetrathiomolybdate. I Initial therapy in 17 neurologically affected patients," *Arch. Neurol.*, 51(6):545-554, 1994b.

Brewer, Dick, Schall, Yuzbasiyan-Gurkan, Mullaney, Pace, Lindgren, Thomas, Padgett, "Use of Zinc Acetate to Treat Copper Toxicosis in Dogs," *JAVMA* 201:564-568, 1992a.

Brewer, Dick, Yuzbasiyan-Gurkan, Johnson, Wang, "Treatment of Wilson's Disease with Zinc XIII: Therapy with Zinc in Presymptomatic Patients from the Time of Diagnosis," *J. Lab. Clin. Med.* 123:849-858, 1993d.

Brewer, Dick, Yuzbasiyan-Gurkan, Tankanow, Young, Kluin, "Initial Therapy of Wilson's Disease Patients with Tetrathiomolybdate," *Arch. Neurol.* 48(1):42-47, 1991a.

Brewer, Hill, Dick, Nostrant, Sams, Wells, Prasad, "Treatment of Wilson's Disease with Zinc III. Prevention of Reaccumulation of Hepatic Copper," *J. Lab. Clin. Med.* 109:526-531, 1987b.

Brewer, Hill, Prasad, Cossak, Rabbini, "Oral zinc therapy for Wilson's disease," *Annals Int. Med.,* 99:314-320, 1983.

Brewer, Hill, Prasad, Dick, "Treatment of Wilson's Disease with Zinc: IV. Efficacy Monitoring using Urine and Plasma Copper," *Proc. Soc. Exper. Biol. Med.* 7:446-455, 1987c.

Brewer, Johnson, Dick, Kluin, Fink, Brunberg, "Treatment of Wilson's disease with ammonium tetrathiomolybdate II. Initial therapy in 33 neurologically affected patients and follow-up on zinc therapy," *Arch. Neurol.* 53:1017-1025, 1996.

Brewer, Schall, Dick, Yuzbasiyan-Gurkan, Thomas, Padgett, "The Use of [64]Copper Measurements to Diagnose Canine Copper Toxicosis," *J. Vet. Int. Med.* 6:41-43, 1992b.

Brewer, Terry, Aisen, Hill, "Worsening of Neurological Syndrome upon Initial Treatment of Wilson's Disease Patients with Penicillamine," *Arch. Neurol.* 44:490-494, 1987a.

Brewer, Turkay, Yuzbasiyan-Gurkan, "Development of neurologic symptoms in a patient with asymptomatic Wilson's disease treated with penicillamine," *Arch. Neurol.* 51:304-305, 1994a.

Brewer, Yuzbasiyan-Gurkan, Dick, "Zinc Therapy of Wilson's Disease VIII. Dose Response Studies," *J. Trace Elem. Exp. Med.* 3:227-234, 1990.

Brewer, Yuzbasiyan-Gurkan, Johnson, "Treatment of Wilson's Disease with Zinc: IX. Response of Serum Lipids," *J. Lab. Clin. Med.* 118:466-470, 1991b.

Brewer, Yuzbasiyan-Gurkan, Johnson, Dick, Wang, "Treatment of Wilson's Disease with Zinc XI. Interaction with other Anticopper Agents," *J. Amer. Coll. Nut.* 12(1), 26-30, 1993a.

Brewer, Yuzbasiyan-Gurkan, Johnson, Dick, Wang, "Treatment of Wilson's Disease with Zinc XII. Dose Regimen Requirements," *Amer. J. Med. Sci.* 305: (4),199-202; 1993b.

Brewer, Yuzbasiyan-Gurkan, Lee, "Regulation of Copper Balance and Its Impairment in Man and Dog," In: Essential and Toxic Trace Elements in Human Health and Disease: An Update, Prasad (Ed.), Allan R. Liss, New York, PCBR 380:129-145, 1993c.

Brewer, Yuzbasiyan-Gurkan, Lee, Appelman, "Treatment of Wilson's Disease with Zinc VI. Initial Treatment Studies," *J. Lab. Clin. Med.* 114: 33-638, 1989.

Brewer, Yuzbasiyan-Gurkan, Young, "Treatment of Wilson's Disease," *Sem. Neurol.* 7:209-220, 1987d.

Byers and Baldwin, "Therapeutic strategies with monoclonal antibodies and immunoconjugates," *Immunology* 65:329-335, 1988.

Carson, Fowlkes, Roubidoux, Moskalik, Govil, Normolle, LeCarpentier, Nattakom and Helvie, "3-D Color Doppler image quantification of breast masses," *Ultrasound Med. Biol.* 24:945-952, 1998.

Coucouvanis et al., "An inorganic functional group approach to the systematic synthesis and reactivity studies of binuclear Mo/S and Mo/S/O complexes," *Polyhedron* 8:1705-1716, 1989.

Coucouvanis et al., "Dinuclear Fe—Mo—S complexes containing the FeS2Mo core. Syntheses, ground-state electronic structures, and crystal and molecular structures of the $[(C_6H_5)_4P]_2[(C_6H_5S)_2FeS_2MoS_2]$, $[(C_2H_5)_4N]_2[(C_6H_5S)_2FeS_2WS_2]$, and $[(C_6H_5)_4P]_2[(S)_5FeS_2MS_2]$ (M=Mo, W) complexes," *Inorg. Chem.* 22:293-308, 1983.

Coucouvanis et al., "Heterodinuclear Di-μ-sulfido bridged dimers containing iron and molybdenum or tungsten. Structures of $(PhP)_2(FeMS_9)$ complexes (M=Mo, W)," *J. Am. Chem. Soc.* 102:1730-1732, 1980a.

Coucouvanis et al., "Successful isolation of a reduced tetrathiometallate complex. Synthesis and structural characterization of the $[(MoS_4)_2Fe]^{3-}$ trianion," *J. Am. Chem. Soc.* 102:6644-6646, 1980b.

Coucouvanis et al., "Synthesis and structural characterization of $[(No)_2FeS_2MoS_2]^{2-}$ a dinitrosyl complex containing the $FeS_2MoS_2$ core," *Inorg. Chim. Acta* 53:L135-L137, 1981.

Coucouvanis et al., "Synthesis of thiomolybdenyl complexes with $[Mo_2(S)_2(O)_2]^{2+}$ cores and substitutionally labile ligands. Crystal and molecular structure of the $[Mo_2O_2S_4(DMF)_3]$ complex," *Inorg. Chem.* 27:3272-3273, 1988.

Coucouvanis et al., "Trinuclear Fe-M-S complexes containing a linear Fe-M-Fe array and a bridging S2MS2 unit. Electronic structures and crystal and molecular structures of the $[(C_6H_5)_4P]_2[Cl_2FeS_2MS_2FeCl_2]$ (M=Mo, W) complexes," *Inorg. Chem.* 23:741-749, 1984.

Coucouvanis, "Fe-M-S complexes derived from $MS_4^{2-}$ anions (M=Mo, W) and their possible relevance as analogues for structural features in the Mo site of nitrogenase," *Acc. Chem. Res.* 14:210-209, 1981.

Coucouvanis, "Syntheses, structures, and reactions of binary and tertiary thiomolybdate complexes containing the $(O)Mo(S_x)$ and $(S)Mo(S_x)$ functional groups (x=1, 2, 4)," *Adv. Inrog. Chem.* 45:1-73, 1998.

Cox, Davis, Shirley, Jack, "Influence of excess dietary molybdenum on rat and calf liver and heart enzymes," *J. Nutr.,* 70:63, 1960.

Culotta, Klomp, Strain, Casareno, Krems and Gitlin, "The copper chaperone for superoxide dismutase," *J. Biol. Chem.* 272:23469-23472, 1997.

Danks, "Disorders of Copper Transport," In: Metabolic Basis of Inherited Diseases, Vol. I, Sixth Ed., Scriver, Beaudet, Sly, Valle (Eds.), McGraw Hill, New York, pp. 1411-1431, 1989.

Dick and Bull, "Some preliminary observations of the effect of molybdenum on copper metabolism in herbivorous animals," *Aust. Vet. J.,* 21:70, 1945.

Dick, Dewey, Gawthome, "Thiomolybdates and the copper-molybdenum-sulphur interaction in ruminant nutrition," *J. Agri. Sci.,* 85:567, 1975.

Dvorak et al., "Distribution of vascular permeability factor (vascular endothelial growth factor) in tumors: concentration in tumor blood vessels," *J. Exp. Med.,* 174:1275-1278, 1991.

Engleka and Maciag, "Inactivation of human fibroblast growth factor-1 (FGF-1) activity by interaction with copper ions involves FGF-1 dimer formation induced by copper-catalyzed oxidation," *J. Biol. Chem.* 267:11307-11315, 1994.

Epenetos et al., "Limitations of radiolabeled monoclonal antibodies for localization of human neoplasms," *Cancer Res.,* 46:3183-3191, 1986.

Fell, Dinsdale, El-Gallad, "Gut Pathology of Rats Dosed with Tetrathiomolybdate," *J. Com. Pathol.* 89:495, 1979.

Ferguson, Lewis, Waterson, "The Teart Pastures of Somerset I. The Cause and Cure of Teartness," *J. Agr. Sci.* 33:44, 1943.

Folkman, "Angiogenesis in cancer, vascular, rheumatoid and other disease," *Nature Med.* 1:27-31, 1995c.

Folkman, "Angiogenesis inhibitors generated by tumors," *Mol. Med.,* 1(2):120-122, 1995a.

Folkman, "Anti-angiogenesis: new concept for therapy of solid tumors," *Ann. Surg.* 175:409-416, 1972.

Folkman, "The influence of angiogenesis research on management of patients with breast cancer," *Breast Cancer Res. Treat.,* 36(2):109-118, 1995b.

Folkman, In: *Cancer: Principles and Practice of Oncology,* Lippincott-Raven Publishers, pp. 3075-3085, 1997.

Fuchs and Sacerdote de Lustig, "Localization of tissue copper in mouse mammary tumors," *Oncol.* 46:183-187, 1989.

Glass, Reich, DeLong, "Wilson's Disease: Development of Neurological Disease After Beginning Penicillamine Therapy," *Arch. Neurol.* 47:595-596, 1990.

Gooneratne, Howell, Gawthorne, "An investigation of the effects of innvenous administration of thiomolybdate on copper metabolism in chronic Cu-poisoned sheep," *Br. J. Nutr.,* 46:469, 1981b.

Gooneratne, Howell, Gawthome, "Intravenous Administration of Thiomolybdate for the Prevention and Treatment of Chronic Copper Poisoning in Sheep," *Br. J. Nutr.* 46:457, 1981a.

Gullino, "Considerations on the mechanism of the angiogenic response," *Anticancer Res.,* 6(2):153-158, 1986.

Gullino, Ziche and Alessandri, "Gangliosides, Copper ions and angiogenic capacity of adult tissues," *Cancer Metastasis Rev.* 9:239-251, 1990.

Guo, Krutzch, Inman and Roberts, "Thrombospondin 1 and type I repeat peptides of thrombospondin 1 specifically induce apoptosis of endothelial cells," *Cancer Res.* 57:1735-1742, 1997.

Guy, Webster, Schaller, Parsons, Cardiff, Muller, "Expression of the neu protooncogene in the mammary epithelium of transgenic mice induces metastatic disease," *Proc. Natl. Acad. Sci. USA,* 89:10578-10582, 1992.

Hadjikyriacou and Coucouvanis, "New members of the $[MO_2(S)_n(S_2)_{6-n}]^{2-}$ series. Synthesis, structural characterization, and properties of the $[Mo_2S_9]^{2-}$, $[Mo_2S_7]^{2-}$ and $[Mo_2S_6]^{2-}$ thioanions," *Inorg. Chem.* 26:2400-2408, 1987.

Hanahan and Folkman, "Patterns and emerging mechanisms of the angiogenic switch during tumorigenesis," *Cell,* 86(3):353-364, 1996.

Harper and Walshe, "Reversible Pancytopenia Secondary to Treatment with Tetrathiomolybdate," *Br. J. Haematol.* 64:851-853, 1986.

Hayes, "Angiogenesis and breast cancer," *Hematol. Oncol. Clin. North Am.,* 8(1):51-71, 1994.

Hill, Brewer, Juni, Prasad, Dick, "Treatment of Wilson's Disease with Zinc II. Validation of Oral $^{64}$Copper Uptake with Copper Balance," *Am. J. Med. Sci.* 12:344, 1986.

Hill, Brewer, Prasad, Hydrick, Hartmann, "Treatment of Wilson's disease with zinc, I: oral zinc therapy regimens," *Hepatology,* 7:522-528, 1987.

Hoogenraad, Koevoet, De Ruyter Korver, "Oral zinc sulfate as long-term treatment in Wilson's disease (hepatolenticular degeneration)," *Eur. Neurol.* 18:205-211, 1979.

Hoogenraad, Van den Hamer, Koevoet, De Ruyter Korver, "Oral zinc in Wilson's disease," *Lancet* 2:1262-1263, 1978.

Hoogenraad, Van Hattum, Van den Hamer, "Management of Wilson's disease with zinc sulfate: Experience in a series of 27 patients," *J. Neurol. Sci.* 77:137-146, 1987.

Horak, Harris, Stuart, Bicknell, "Angiogenesis in breast cancer. Regulation, prognostic aspects, and implications for novel treatment strategies," *Ann. NY Acad. Sci.,* 698:71-84, 1993.

Humphries, Mills, Greig, Roberts, Inglis, Halliday, "Use of Ammonium Tetrathiomolybdate in the Treatment of Copper Poisoning in Sheep," *Vet. Record* 119:596-598, 1986.

Humphries, Morrice, Bremner, "A Convenient Method for the Treatment of Chronic Copper Poisoning in Sheep using Subcutaneous Ammonium Tetrathiomolybdate," *Vet. Record* 123:51-53, 1988.

Hynes, Lamand, Montel, Mason, "Some Studies on the Metabolism and the Effects of $^{99}$Mo- and $^{35}$S-Labelled Thiomolybdates After Intravenous Infusion in Sheep," *Br. J. Nutr.* 52:149, 1984.

Ingber et al., "Angioinhibins: Synthetic analogues of fumagillin which inhibit angiogenesis and suppress tumor growth," *Nature,* 48:555-557, 1990.

Iruela-Arispe and Dvorak, "Angiogenesis: A dynamic balance of stimulators and inhibitors," *Thromb. Haemost.* 78:672-677, 1997.

Jacob, Sanstead, Munoz, Klevay, Milne, "Whole body surface loss of trace metals in normal males," *Am. J. Clin. Nutr.,* 34:1379-1383, 1981.

Jain, "Vascular and interstitial barriers to delivery of therapeutic agents in tumors," *Cancer Metastasis Rev.,* 9:253-266, 1990.

Jones, Gooneratne, Howell, "X-ray Microanalysis of Liver and Kidney in Copper Loaded Sheep with and without Thiomolybdate Administration," *Res. Vet. Sci.* 37-273, 1984.

Juweid et al., "Micropharmacology of monoclonal antibodies in solid tumors: direct experimental evidence for a binding site barrier," *Cancer Res.,* 52:5144-5153, 1992.

Kanatzidis and Coucouvanis, "Structure of Bis(tetraethylammonium) tetrathiomolybdate(VI), $2C_8H_{20}N^+MoS_4^{2-}$," *Acta Cryst.* C39:835-838, 1983.1983.

Lannutti, Gately, Quevedo, Soff and Paller, "Human angiostatin inhibits murine hemangioendothelioma tumor growth in vivo," *Cancer Res.* 57:5277-5280, 1997.

LeCarpentier, Tridandapani, Fowlkes, Roubidoux, Moskalik and Carson, "Utility of 3D ultrasound in the discrimination and detection of breast cancer," *Rad. Soc, North Amer. EJ,* 1999.

Lee, Brewer, Wang, "The Treatment of Wilson's Disease with Zinc VII. Protection of the Liver for Copper Toxicity by Zinc Induced Metallothionein in a Rat Model," *J. Lab. Clin. Med.* 114:639-645, 1989.

Linder, Houle, Isaacs, Moor and Scott, "Copper regulation of ceruloplasmin in copper-deficient rats," *Enzyme* 24:23-35, 1979.

Lowder et al., "Studies on B lymphoid tumors treated with monoclonal anti-idiotype antibodies: correlation with clinical responses," *Blood,* 69:199-210, 1987.

Macilese Ammerman, Valsecchi, Dunavant, Davis, "Effect of dietary molybdenum and sulfate upon copper metabolism in sheep," *J. Nutr.,* 99:177, 1969.

Marshall, Wellstein, Rae, DeLap, Phipps, Hanfelt, Yunmbam, Sun, Duchin and Hawkins, "Phase I trial of orally administered pentosan polysulfate in patients with advanced cancer," *Clin. Cancer Res.* 3:2347-2354, 1997.

Mason, "The biochemical pathogenesis of molybdenum-induced copper deficiency syndromes in ruminants: Towards the final chapter," *Irish Veter. J.,* 43:18-21, 1990.

Mason, Lamand, Hynes, "$^{99}$Mo Metabolism in Sheep After the Intravenous Injection of $^{99}$Mo Thiomolybdates," *J. Inorg. Biochem.* 19:153, 1983.

McQuaid and Mason, "A comparison of the effects of penicillamine, trientine, and trithiomolybdate on [$^{35}$S]-labeled metallothionein in vitro; the implications for Wilson's disease therapy," *J. Inorg. Biochem.,* 41:87-92, 1991.

Merajver, Irani, van Golen and Brewer, "Copper depletion as an anti-angiogenic strategy in HER2-neu transgenic mice," *Proceedings of Special AACR Conference on Angiogenesis and Cancer,* Abstract #B-11, Jan. 22-24, 1998.

Millauer, Longhi, Plate, Shawver, Risau, Ullrich and Strawn, "Dominant-negative inhibition of Flk-1 suppresses the growth of many tumor types in vivo," *Cancer Res.* 56:1615-1620, 1996.

Miller and Engel, "Interrelations of copper, molybdenum; and sulfate sulfur in nutrition," *Fed. Proc.,* 19:666, 1960.

Mills, El-Gallad, Bremner, "Effects of molybdate, sulfide, and tetrathiomolybdate on copper metabolism in rats," *J. Inorg. Biochem.,* 14:189, 1981a.

Mills, El-Gallad, Bremner, Wenham, "Copper and molybdenum absorption by rats given ammonium tetrathiomolybdate," *J. Inorg. Biochem.,* 14: 163, 1981b.

Mills, Monty, Ichihara, Pearson, "Metabolic effects of molybdenum toxicity in the rat," *J. Nutr.,* 65:129, 1958.

Muller and Krickemeyer, *Inorg. Synth.* 27:47, 1990.

Muller, Nolte and Krebs, *Inorg. Chem.* 19:2835, 1980.

Muller, Sinn, Pattengale, Wallace, Leder, "Single-step induction of mammary adenocarcinoma in transgenic mice bearing the activated c-neu oncogene," *Cell,* 54:105-115, 1988.

O'Reilly, Boehm, Shing, Fukai, Vasios, Lane, Flynn, Birkhead, Olsen and Folkman, "Endostatin: An endogenous inhibitor of angiogenesis and tumor growth," *Cell* 88:277-285, 1997.

O'Reilly, Holmgren, Shing, Chen, Rosenthal, Moses, Lane, Cao, Sage and Folkman, "Angiostatin: A novel angiogenesis inhibitor that mediates the suppression of metastases by a Lewis lung carcinoma," *Cell* 79:315-328, 1994.

Parangi, O'Reilly, Christofori, Holmgren, Grosfeld, Folkman, Hanahan, "Antiangiogenic therapy of transgenic mice impairs de novo tumor growth," *Proc. Natl. Acad. Sci. USA,* 93(5):2002-2007, 1996.

Parke, Bhattacherjee, Palmer, Lazarus, "Characterization and quantification of copper sulfate-induced vascularization of the robbit cornea," *Am. J. Pathol.,* 137:173-178, 1988.

Patstone and Maher, "Copper and calcium binding motifs in the extracellular domains of fibroblast growth factor receptors," *J. Biol. Chem.* 271:3343-3346, 1996.

Qian, Wang, Rothman, Nicosia and Tuszynski, "Thrombospondin-1 modulates angiogenesis in vitro by up-regulation of matrix metalloproteinase-9 endothelial cells," *Exp. Cell Res.* 235:403-412, 1997.

Raju, Alessandri, Ziche, Gullino, "Ceruloplasmin, Copper Ions, and Angiogenesis," *J. Natl. Cancer Inst.* 69:1183-1188, 1982.

*Remington's Pharmaceutical Sciences,* 15th Ed., Mack Publishing Company, 1975.

*Remington's Pharmaceutical Sciences,* 16th Ed., Mack Publishing Company, 1980.

Salnikow, Wang and Costa, "Induction of activating transcription factor 1 by Nickel and its role as a negative regulator of thrombospondin I gene expression," *Cancer Res.* 57:5060-5066, 1997.

Sands, *Immunoconjugates and Radiopharmaceuticals,* 1:213-226, 1988.

Schapira and Schapira, "Use of ceruloplasmin levels to monitor response to therapy and predict recurrence of breast cancer," *Breast Cancer Res Treat.* 3:223-224, 1983.

Scheinberg and Sternlieb, "Wilson's Disease," In: Major Problems in Internal Medicine, Vol. XXIII, W.B. Saunders Company, Philadelphia, 1984.

Seelig, "Review: Relationships of Copper and Molybdenum to Iron Metabolism," *Am. J. Clin. Nutr.* 25:1022, 1972.

Shing, "Heparin-copper biaffinity chromatography of fibroblast growth factors," *J. Biol. Chem.* 263:9059-9062, 1988.

Shockley et al., "Penetration of tumor tissue by antibodies and other immunoproteins," *Ann. N.Y. Acad. Sci.,* 617:367-382, 1991.

Sim, O'Reilly, Liang, Fortier, He, Madsen, Lapcevich and Nacy, "A recombinant human angiostatin protein inhibits experimental primary and metastatic cancer," *Cancer Res.* 57:1329-1334, 1997.

Suzuki, Yamamoto, Aoki, Takeichi, "Selective removal of copper bound to metalliothionein in the liver of LEC rats by tetrathiomolybdate," *TOXIC* 83:149, 1993.

Takahashi, Mulliken, Kozakewich, Rogers, Folkman and Ezekowitz, "Cellular markers that distinguish the phases of hemangioma during infancy and childhood," *J. Clin. Invest.* 93:2357-2364, 1994.

Teo et al., "Mo, W, and Fe EXAFS of the $[Cl_2FeS_2MS_2FeCl_2]^{2-}$ (M=Mo, W) dianions. A comparison with the Mo EXAFS of nitrogenase," *J. Am. Chem. Soc.* 105:5767-5770, 1983.

Vitetta et al., "Phase I immunotoxin trial in patients with B-cell lymphoma," *Cancer Res.,* 15:4052-4058, 1991.

Volpert, Stellmach and Bouck, "The modulation of thrombospondin and other naturally occurring inhibitors of angiogenesis during tumor progression," *Breast Cancer Res. Treat.,* 36:119-126, 1995.

Volpert, Ward, Lingen, Chesler, Solt, Johnson, Molteni, Polverini and Bouck, "Captopril inhibits angiogenesis and slows the growth of experimental tumors in rats," *J. Clin. Invest.* 98:671-679, 1996.

Walshe, "Penicillamine: A New Oral Therapy for Wilson's Disease," *Am. J. Med.* 21:487, 1956.

Walshe, "Treatment of Wilson's disease with trientine (triethylene tetramine) dihydrochloride," *Lancet,* 1:643-647, 1982.

Warren, Yuan, Malti, Gillett and Ferrara, "Regulation by vascular endothelial growth factor of human colon cancer tumorigenesis in a mouse model of experimental liver metastasis," *J. Clin. Invest.* 95:1789-1797, 1995.

Watanabe, Seno, Sasada and Igarashi, "Molecular characterization of recombinant human acidic fibroblast growth factor produced in *E. coli*: Comparative studies with human basic fibroblast growth factor," *Mol. Endo.* 4:869-879, 1990.

Wu, Forbes, Chen, Cox, "The LEC rat has a deletion in the copper transporting ATPase gene homologous to the Wilson disease gene," *Nat. Genet.* 7:541, 1994.

Yoshida, Ikeda, Nakazawa, "Copper chelation inhibits tumor angiogenesis in the experimental 9L gliosarcoma model," *Neurosurgery*, 37(2):287-292, 1995.

Young, Shoulson, Penney et al., "Huntington's Disease in Venezuela: Neurologic Features and Functional Decline," *Neurol.* 36:244-249, 1986.

Yuan, Chen, Dellian, Safabakhsh, Ferrara and Jain, "Time-dependent vascular regression and permeability changes in established human tumor xenografts induced by an anti-vascular endothelial growth factor/vascular permeability factor antibody," *Proc. Natl. Acad. Sci. USA* 93:14765-14770, 1996.

Yuzbasiyan-Gurkan, Brewer, Abrams, Main, Giacherio, "Treatment of Wilson's Disease with Zinc V. Changes in Serum Levels of Lipase, Amylase and Alkaline Phosphatase in Wilson's Disease Patients," *J. Lab. Clin. Med.* 114:520-526, 1989.

Yuzbasiyan-Gurkan, Grider, Nostrant, Cousins, Brewer, "The Treatment of Wilson's Disease with Zinc X. Intestinal Metallothionein Induction," *J. Lab. Clin. Med.* 120: 380-386, 1992.

Ziche, Jones, Gullino, "Role of Prostaglandin $E_1$ and Copper in Angiogenesis," *J. Natl. Cancer Inst.* 69:475-482, 1982.

What is claimed is:

1. A method of treating a disease characterized by ocular neovascularization in an animal, comprising orally administering to an animal having a disease characterized by ocular neovascularization a loading dose of greater than 200 mg daily up to 410 mg daily of a thiomolybdate compound that binds copper and forms thiomolybdate compound-copper-protein complex.

2. The method of claim 1, wherein said thiomolybdate compound comprises at least a first iron atom.

3. The method of claim 1, wherein said thiomolybdate compound comprises at least a first oxygen atom.

4. The method of claim 1, wherein said thiomolybdate compound is associated with at least a first carbohydrate molecule.

5. The method of claim 4, wherein said carbohydrate molecule is a disaccharide molecule.

6. The method of claim 4, wherein said carbohydrate molecule is a sucrose molecule.

7. The method of claim 6, wherein said thiomolybdate compound is associated with about 30 sucrose molecules.

8. The method of claim 1, wherein said thiomolybdate compound is dodecathiodimolybdate, tetrathiomolybdate, iron octathiodimolybdate, trithiomolybdate, dithiomolybdate or monothiomolybdate.

9. The method of claim 8, wherein said thiomolybdate compound is dodecathiodimolybdate.

10. The method of claim 8, wherein said thiomolybdate compound is iron octathiodimolybdate.

11. The method of claim 8, wherein said thiomolybdate compound is tetrathiomolybdate.

12. The method of claim 1, further comprising administering to said animal a therapeutically effective amount of a zinc compound.

13. The method of any one of claims 2 through 11, wherein said animal is a human subject.

14. The method of claim 13, wherein said thiomolybdate compound is administered to said human subject in an amount and for a time effective to reduce the level of copper in said human subject to between about 40% and about 10% of the level of copper in said human subject prior to administration of said thiomolybdate compound.

15. The method of claim 14, wherein said thiomolybdate compound is administered to said human subject in an amount and for a time effective to reduce the level of copper in said human subject to about 20% of the level of copper in said human subject prior to administration of said thiomolybdate compound.

16. The method of claim 14, comprising:
  a) administering said thiomolybdate compound to said human subject in an amount and for a time effective to reduce the level of copper in said human subject to about 20% of the level of copper in said human subject prior to administration of said thiomolybdate compound; and
  b) administering to said human subject a therapeutically effective amount of a zinc compound.

17. The method of claim 16, wherein said therapeutically effective amount of a zinc compound is administered to said human subject for a period of time effective to maintain the level of copper in said human subject at about 20% of the level of copper in said human subject prior to administration of said thiomolybdate compound.

18. The method of claim 14, wherein the level of copper in said human subject is indicated by the level of serum ceruloplasmin.

19. The method of claim 1, wherein said disease is associated with corneal neovascularization.

20. The method of claim 19, wherein said disease is epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, trauma, Scleritis, Steven's Johnson disease, periphigoid radial keratotomy or corneal graft rejection.

21. The method of claim 1, wherein said disease is associated with retinal/choroidal neovascularization.

22. The method of claim 21, wherein said disease is diabetic retinopathy, sickle cell anemia, pseudoxanthoma elasticum, Pagets disease, vein occlusion, artery occlusion, carotid obstructive disease, chronic uveitis/vitritis, Lyme's disease, pars planitis, chronic retinal detachment, hyperviscosity syndromes, toxoplasmosis, trauma or post-laser complication.

23. The method of claim 21, wherein said disease is associated with choroidal neovascularization.

24. The method of claim 23, wherein said disease is age-related macular degeneration, dry type macular degeneration, ocular histoplasmosis syndrome, pathologic myopia or angioid streaks.

25. The method of any one of claims 19 through 24, wherein said animal is a human subject.

* * * * *

UNITED STATES PATENT AND TRADEMARK OFFICE
CERTIFICATE OF CORRECTION

PATENT NO. : 7,438,931 B2 Page 1 of 1
APPLICATION NO. : 10/796782
DATED : October 21, 2008
INVENTOR(S) : George J. Bremer et al.

It is certified that error appears in the above-identified patent and that said Letters Patent is hereby corrected as shown below:

On the Cover Page:

Item (*), add -- This patent is subject to a terminal disclaimer. --.

Signed and Sealed this

Seventeenth Day of February, 2009

JOHN DOLL
*Acting Director of the United States Patent and Trademark Office*